United States Patent
Dailey et al.

(10) Patent No.: US 7,503,333 B2
(45) Date of Patent: Mar. 17, 2009

(54) METHOD OF WASHING A SURFACE WITH A SURFACTANT COMPOSITION

(75) Inventors: James S. Dailey, Grosse Ile, MI (US); Ernesto Lippert, Oak Ridge, NJ (US); Sridhar Iyer, Matthews, NC (US); Richard Baur, Mutterstadt (DE); Frank Rittig, Gontardstrasse (DE)

(73) Assignee: BASF Corporation, Florham Park, NJ (US)

( * ) Notice: Subject to any disclaimer, the term of this patent is extended or adjusted under 35 U.S.C. 154(b) by 0 days.

(21) Appl. No.: 11/932,420

(22) Filed: Oct. 31, 2007

(65) Prior Publication Data

US 2008/0103083 A1    May 1, 2008

Related U.S. Application Data

(63) Continuation-in-part of application No. 11/677,824, filed on Feb. 22, 2007.

(30) Foreign Application Priority Data

Feb. 22, 2006    (EP)    .................... 06110269

(51) Int. Cl.
  *B08B 3/04* (2006.01)
  *C11D 1/72* (2006.01)
  *C11D 1/825* (2006.01)

(52) U.S. Cl. .............. 134/25.2; 134/25.3; 134/39; 134/42; 8/137; 510/342; 510/360; 510/365; 510/421; 510/475; 510/505; 510/524; 510/525

(58) Field of Classification Search ............ 510/342, 510/360, 365, 421, 475, 505, 524, 525; 8/137; 134/25.2, 39, 25.3, 42
See application file for complete search history.

(56) References Cited

U.S. PATENT DOCUMENTS 3,953,352 A    4/1976    Mizutani et al.

(Continued)

FOREIGN PATENT DOCUMENTS

EP    0669906    5/1997

(Continued)

OTHER PUBLICATIONS

English language translation and abstract for JP 2004035755 extracted from Japanese Patent Office, 17 pages, Feb. 5, 2005.

(Continued)

*Primary Examiner*—Brian P Mruk

(57) ABSTRACT

A method of washing a surface includes the step of providing a cleaning formulation including a surfactant composition including a first surfactant, a second surfactant, and a polyalkylene glycol. The first surfactant has the general formula: $R^1$—O-$(A)_m$H. $R^1$ is an aliphatic hydrocarbon having from 8 to 11 carbon atoms, A is an alkyleneoxy group having from 2 to 5 carbon atoms, and m is a positive number. The second surfactant has the general formula: $R^2$—O-$(B)_n$H. $R^2$ is an aliphatic hydrocarbon having from 12 to 14 carbon atoms, B is an alkyleneoxy group having from 2 to 5 carbon atoms, and n is a positive number. The polyalkylene glycol is present in an amount of from 3 to 20 parts by weight. The method also includes providing a rinse formulation, applying the cleaning formulation to the surface, and applying the rinse formulation to the surface.

25 Claims, 18 Drawing Sheets

U.S. PATENT DOCUMENTS

| | | | |
|---|---|---|---|
| 4,013,579 A | 3/1977 | Nakasone et al. |
| 4,043,931 A | 8/1977 | Jeffrey et al. |
| 4,269,723 A | 5/1981 | Barford et al. |
| 4,501,680 A | 2/1985 | Aszman et al. |
| 4,587,030 A | 5/1986 | Casey |
| 4,722,802 A | 2/1988 | Hutchings et al. |
| 4,820,449 A | 4/1989 | Menke et al. |
| 4,911,858 A | 3/1990 | Bunczk et al. |
| 4,911,859 A | 3/1990 | Bunczk et al. |
| 4,999,869 A | 3/1991 | Holland et al. |
| 5,049,302 A | 9/1991 | Holland et al. |
| 5,340,495 A | 8/1994 | Mulcahy et al. |
| 5,342,550 A | 8/1994 | Burke et al. |
| 5,514,288 A | 5/1996 | Holland et al. |
| 5,562,850 A | 10/1996 | Woo et al. |
| 5,608,118 A | 3/1997 | Dahlgren et al. |
| 5,661,121 A | 8/1997 | Dahlgren et al. |
| 5,733,856 A | 3/1998 | Gopalkrishnan et al. |
| 5,789,369 A | 8/1998 | Gopalkrishnan et al. |
| 6,159,916 A | 12/2000 | Robbins et al. |
| 6,187,738 B1 | 2/2001 | Micciche et al. |
| 6,221,823 B1 | 4/2001 | Crisanti et al. |
| 6,242,402 B1 | 6/2001 | Robbins et al. |
| 6,315,835 B1 | 11/2001 | Kerobo et al. |
| 6,420,329 B1 | 7/2002 | Callaghan et al. |
| 6,455,486 B1 | 9/2002 | Kerobo et al. |
| 6,559,112 B2 | 5/2003 | Fox et al. |
| 6,627,590 B1 | 9/2003 | Sherry et al. |
| 6,897,188 B2 | 5/2005 | Gohl et al. |
| 7,189,685 B2 | 3/2007 | Hubig et al. |
| 2005/0170991 A1* | 8/2005 | Ruland et al. ............... 510/421 |
| 2005/0181967 A1 | 8/2005 | Ruland et al. |
| 2007/0225189 A1 | 9/2007 | Dailey et al. |

FOREIGN PATENT DOCUMENTS

| | | |
|---|---|---|
| EP | 0669907 | 5/1997 |
| JP | 2003336092 | 11/2003 |
| JP | 2004035755 | 2/2004 |
| JP | 2004091686 | 3/2004 |
| WO | WO 03/091190 | * 11/2003 |

OTHER PUBLICATIONS

English language translation and abstract for JP 2003336092 extracted from Japanese Patent Office, 15 pages, Nov. 28, 2003.

English language translation and abstract for JP 2004091686 extracted from Japanese Patent Office, 31 pages, Mar. 25, 2004.

English language translation of European Patent Application No. EP 0611269.5, filed Feb. 22, 2006, 37 pages.

* cited by examiner

US 7,503,333 B2

METHOD OF WASHING A SURFACE WITH A SURFACTANT COMPOSITION

RELATED APPLICATIONS

This application is a continuation-in-part of, and claims priority to U.S. Ser. No. 11/677,824, filed on Feb. 22, 2007, and entitled "Surfactant Composition and Method of Forming", which claims priority to European Patent Application Number EP 06110269.5, filed on Feb. 22, 2006.

FIELD OF THE INVENTION

The present invention generally relates to a method of washing a surface. More specifically, the present invention relates to a method of washing including the step of applying a cleaning formulation to the surface. The cleaning formulation includes a surfactant composition including a particular first surfactant, second surfactant, and polyalkylene glycol.

DESCRIPTION OF THE RELATED ART

Cleaning formulations are well known in the art, especially those used in industrial and institutional (I&I) applications. I&I cleaning formulations are typically used to remove dirt, oil, grease, food, and the like, from surfaces such as hard surfaces and textiles soiled with a variety of stains. A particularly problematic stain to remove from textiles is used motor oil, i.e., a stain from motor oil used in both diesel and gas engines. Typically, the I&I cleaning formulations that are the most efficacious in removing these types of stains include alkoxylated alkyl phenols, a chemical family that, together with their degradation products such as nonylphenol (NP), are potentially hazardous, non-biodegradable, and may be toxic to certain types of aquatic life. These particular I&I cleaning formulations also have a tendency to display erratic foaming tendencies and gel upon addition of water. This requires use of solvents to decrease viscosity and control foaming, thereby raising production and shipping costs. This also requires use of increased amounts of the I&I cleaning formulations, which increases purchasing costs to the end user.

One particular cleaning formulation, disclosed in Japanese Patent Publication Number 2004035755A, includes alkylene oxide adducts of aliphatic alcohols and also includes an organic diluent such an alkyl alcohol and/or a glycol, which is used to dilute the composition in amounts of from 5 to 95% by weight. Dilution of the cleaning formulation in such varied amounts greatly decreases the efficacy of the cleaning formulation in reducing surface tension of water, in controlling an amount of foaming, and in forming micelles at low concentrations. As a result, these varied amounts of dilution minimize any benefits to cleaning provided by this cleaning formulation.

Although the known I&I cleaning formulations are widely used, there remains an opportunity to develop a method of washing a surface using a biodegradable cleaning formulation thereby reducing amounts of alkoxylated alkyl phenols used in I&I cleaning formulations and released into the environment. There also remains an opportunity to develop a method of washing a surface using a cleaning composition that includes a surfactant composition that reduces the surface tension of water under both static and dynamic conditions at low concentrations and that has improved physical properties, e.g., controlled levels of foaming, decreased gelling upon dilution with water, decreased critical micelle concentrations, and increased solubility in alkaline compositions.

There further remains an opportunity to develop a method for treating particularly resilient stains, such as used motor oil stains, on surfaces using the cleaning formulation.

BRIEF DESCRIPTION OF THE DRAWINGS

Other advantages of the present invention will be readily appreciated, as the same becomes better understood by reference to the following detailed description when considered in connection with the accompanying drawings. In each of the block diagrams of FIGS. 1-4, various embodiments of the instant method are set forth including steps that occur in order in those embodiments. In each of the diamond error graphs of FIGS. 5-18, the diamonds represent standard deviations surrounding mean percent clean values. Overlapping circles represent statistically insignificant differences in mean data determined using a matched-pair student T test at a confidence interval of 95%. Circles that do not overlap represent statistically significant differences in mean data determined using the matched-pair student T test at the confidence interval of 95%.

FIG. 5 represents the data set forth in Table 2.

FIG. 6 represents the data set forth in Table 3.

FIG. 7 represents the data set forth in Table 4.

FIG. 8 represents the data set forth in Table 5.

FIG. 9 represents the data set forth in Table 6.

FIG. 10 represents the data set forth in Table 7.

The Cleaning Formulations are diluted in a first cleaning solution and applied to polyester (65%)/cotton (35%) blend swatches stained with EMPA 104 (carbon black/olive oil) which are washed at 120° F. FIG. 11 represents the data set forth in Table 8.

FIG. 12 represents the data set forth in Table 9.

FIG. 13 represents the data set forth in Table 10.

FIG. 14 represents the data set forth in Table 11.

FIG. 15 represents the data set forth in Table 15, Cleaning Formulations 33-55 and Comparative Cleaning Formulations 17-24.

FIG. 16 represents the data set forth in Table 15, Cleaning Formulations 56-76 and Comparative Cleaning Formulations 25-32.

FIG. 17 represents the data set forth in Table 17, Cleaning Formulations 77-97 and Comparative Cleaning Formulations 33-39.

FIG. 18 represents the data set forth in Table 17, Cleaning Formulations 98-119 and Comparative Cleaning Formulations 40-45.

SUMMARY OF THE INVENTION AND ADVANTAGES

The present composition provides a method of washing a surface. The method includes the step of providing a cleaning formulation. The cleaning formulation includes a surfactant composition. The surfactant composition includes a first surfactant, a second surfactant, and a polyalkylene glycol. The first surfactant has the general formula: $R^1$—O-(A)$_m$H, wherein $R^1$ is an aliphatic hydrocarbon having from 8 to 11 carbon atoms, A is an alkyleneoxy group having from 2 to 5 carbon atoms, and m is a positive number. The second surfactant has the general formula: $R^2$—O-(B)$_n$H, wherein $R^2$ is an aliphatic hydrocarbon having from 12 to 14 carbon atoms, B is an alkyleneoxy group having from 2 to 5 carbon atoms, and n is a positive number. The polyalkylene glycol is present in an amount of from 3 to 20 parts by weight per 100 parts by weight of the cleaning formulation. The method also includes the steps of providing a rinse formulation, applying the cleaning formulation to the surface, and applying the rinse formulation to the surface.

The cleaning formulation can be used to effectively wash surfaces due to a solubility of the surfactant composition in alkaline compositions and a decreased critical micelle concentration such that a minimized amount of the cleaning formulation can be used, thereby reducing costs. The surfactant composition of the cleaning formulation also resists gelling upon addition to water and has increased dispersibility/solubility/miscibility in water. This alleviates a need for addition of solvents or water to reduce viscosity. This directly reduces production and shipping costs and also reduces purchasing costs for an end user. Further, the surfactant composition reduces the surface tension of water under both static and dynamic conditions at low concentrations thereby optimizing performance in both low mechanical action applications and high mechanical action (spray) applications by increasing surface wetting.

DETAILED DESCRIPTION OF THE INVENTION

Figure 1:
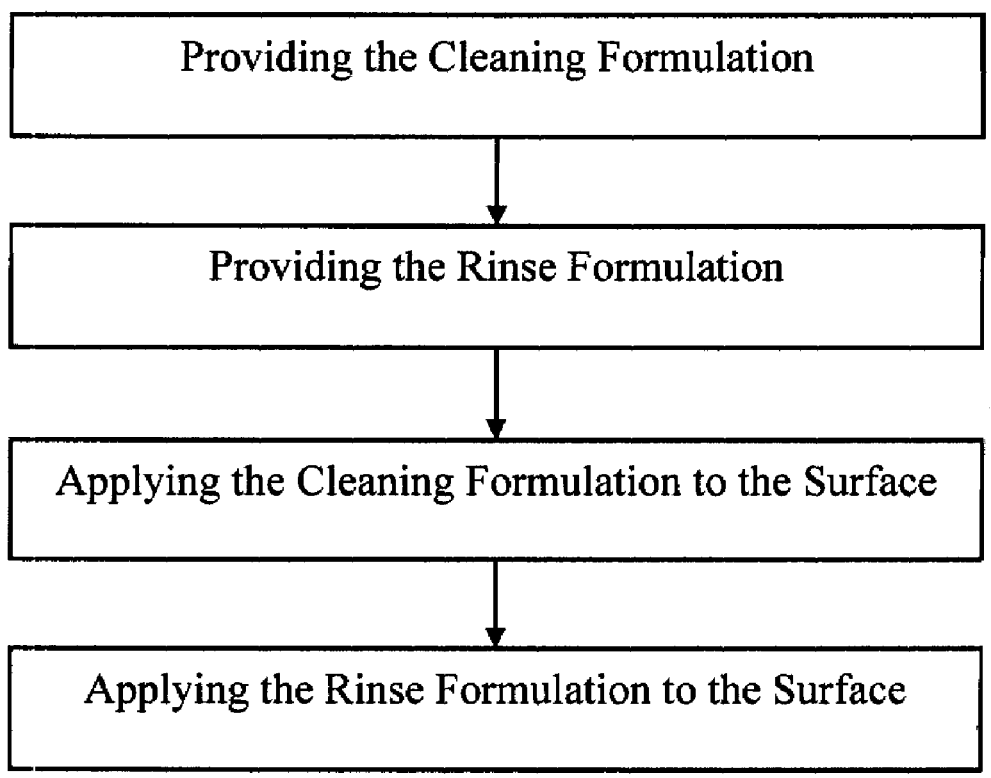
FIG. 1 is a block diagram illustrating the steps of a first embodiment of the instant invention.

The instant invention provides a method of washing a surface, as set forth in FIG. 1. In one embodiment, the surface is a hard surface. Non-limiting examples of hard surfaces are those found in kitchens and bathrooms, on walls and floors, in showers and bathtubs, on countertops and cabinets, on exterior surfaces such as on driveways, patios, siding, decking, and the like, on vehicles, and on marble, glass, metal, vinyl, fiberglass, ceramic, granite, concrete, acrylic, Formica®, Silestone®, Corian®, and laminated surfaces. In another embodiment, the surface is a soft surface. Examples of soft surfaces include, but are not limited to, fabrics, textiles, and carpets.

It is contemplated that washing may be further defined as laundering. Washing may include dry cleaning a surface (e.g. a textile) and/or treating stains on the surface. The textile typically includes cloth, fabric, and/or yarn and may include, but is not limited to, polyester, cotton, nylon, wool, silk, and combinations thereof. In one embodiment, the textile includes a commercial uniform, e.g., coveralls, overalls, medical scrubs, prison uniforms, etc. The textile may be soiled with stains such as greasy stains, inorganic stains, organic stains, petroleum based stains, and combinations thereof. Non-limiting examples of greasy stains include stains resulting from sebum, body oils, animal fats, carbohydrates, proteins, soap scums, etc. Examples of inorganic stains include, but are not limited to, stains resulting from scale/lime deposits, rust, corrosion and oxidation, minerals, water spots, etc. Typical organic stains include, but are not limited to, stains resulting from ink, mold, yeast, blood, grass, mustard, coffee, alcohol, bacteria and animal waste, vomit, etc. Non-limiting examples of typical petroleum based stains include stains resulting from used motor oil from both gasoline and diesel engines, axle grease, gum, paint, tar, lipstick and make-up, paraffins, cooking oils, adhesive residue, etc.

The cleaning formulation is preferably biodegradable. The terminology "biodegradable," as referenced herein, refers to a tendency of the cleaning formulation to be chemically degraded via natural effectors such as soil bacteria, weather, plants and/or animals. The biodegradability of the cleaning formulation reduces a possibility of pollution and formation of environmental hazards and is dependent on the components of the cleaning formulation.

The cleaning formulation includes a first surfactant, a second surfactant, and a polyalkylene glycol. In one embodiment, the cleaning formulation consists essentially of the first surfactant, second surfactant, and the polyalkylene glycol. In another embodiment, the cleaning formulation consists of the first surfactant, the second surfactant, and the polyalkylene glycol.

The first surfactant has the general formula $R^1$—O-$(A)_m$H. In this formula, $R^1$ is an aliphatic hydrocarbon having from 8 to 11 carbon atoms. As is known in the art, aliphatic hydrocarbons may include straight, branched, and/or cyclic chains of carbon and hydrogen atoms which may be saturated or unsaturated. It is contemplated that $R^1$ may include a mixture of different aliphatic hydrocarbons having 8, 9, 10, and 11 carbon atoms. Alternatively, $R^1$ can be an aliphatic hydrocarbon having 8 carbon atoms, 9 carbon atoms, 10 carbon atoms, or 11 carbon atoms. Preferably, $R^1$ is an aliphatic hydrocarbon having 10 carbon atoms. An example of a particularly suitable hydrocarbon having 10 carbon atoms includes, but is not limited to, a 2-propylheptane moiety. It is to be understood that the terminology "2-propylheptane moiety" refers to a $C_{10}H_{22}$ moiety bonded to the oxygen atom of the first surfactant. For descriptive purposes only, a chemical structure of the 2-propylheptane moiety is shown below:

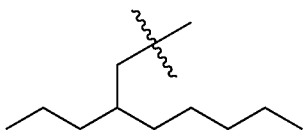

In another embodiment, the first surfactant is substantially free of aliphatic hydrocarbons having less than 8 carbon atoms and/or more than 11 carbon atoms. The terminology "substantially free" refers to an amount of the hydrocarbons of preferably of less than 10% by weight, more preferably of less than 5% by weight, and most preferably of less than 1% by weight, of the cleaning formulation.

It is contemplated that the aliphatic hydrocarbon having from 8 to 11 carbon atoms may have any average degree of branching. That is, the aliphatic hydrocarbon having from 8 to 11 carbon atoms may have an average degree of branching of zero or may have an average degree of branching of greater than zero. Preferably, the aliphatic hydrocarbon having from 8 to 11 carbon atoms has an average degree of branching of approximately one. The degree of branching is defined as a number of carbon atoms in aliphatic hydrocarbon (3° carbon atoms) which are bonded to three additional carbon atoms, plus two times a number of carbon atoms (4° carbon atoms) which are bonded to four additional carbon atoms. The average degree of branching is calculated as a sum of all degrees of branching of individual aliphatic hydrocarbon molecules divided by a total number of the individual aliphatic hydrocarbon molecules. The degree of branching may be determined, for example, through use of $^{13}C$ NMR methods such as COSY, DEPT, INADEQUATE, followed by quantification via use of relaxation reagents. Other NMR methods and GC-MS methods may also be used.

In addition to $R^1$, A is an alkyleneoxy group having from 2 to 5 carbon atoms. The alkyleneoxy group may include, but is not limited to, ethyleneoxy groups (2 carbon atoms), propyleneoxy groups (3 carbon atoms), butyleneoxy groups (4 carbon atoms), pentoxy groups (5 carbon atoms), and combinations thereof. The butyleneoxy groups may include any or all of 1,2-butylene oxide groups, 2,3-butylene oxide groups, and isobutylene oxide groups. Most preferably, A is further defined as an ethyleneoxy group (2 carbon atoms).

Further, m is a positive number. As is known in the art, m represents a number of moles of the alkyleneoxy group added to the aliphatic hydrocarbon of the first surfactant. It is contemplated that m can be any whole number or any fraction greater than zero. In one embodiment, the first surfactant includes a mixture of molecules having differing numbers of moles of the alkyleneoxy group added to the aliphatic hydrocarbon molecules. In one embodiment, m is a number of from 3 to 50, more preferably of from 3 to 12, still more preferably of from 5 to 12, and most preferably of from 5 to 10. In another embodiment, m is a number of from 3 to 100, more preferably of from 3 to 15, still more preferably of from 3 to 12, and most preferably of from 3 to 10. When m is greater than or equal to 2, it is contemplated that the alkyleneoxy groups may be distributed randomly or blockwise. Additionally, the first surfactant is preferably present in the cleaning formulation in an amount of from 10 to 90, and more preferably of from 15 to 75, parts by weight per 100 parts by weight of the composition.

The first surfactant preferably has both an aqueous cloud point and a solvent cloud point of from 25 to 80, more preferably of from 30 to 70, and most preferably of from 40 to 70, ° C. As is known in the art, cloud point is a measure of a temperature where the (first) surfactant begins to phase separate such that two phases appear, thus making the (first) surfactant cloudy. To determine the aqueous cloud points, 1% by weight of the (first) surfactant is added to water and either heated or cooled. To determine the solvent cloud points, approximately 5 grams of the (first) surfactant is added to 25 grams of an aqueous solution including 25% by weight of butyldiglycol.

In one embodiment, the (first) surfactant preferably has a hydrophilic lipophilic balance (HLB) of from 7 to 15, more preferably of from 9 to 14, and most preferably of from 11 to 14, as determined by the Griffin method. In another embodiment, the (first) surfactant preferably has a hydrophilic lipophilic balance (HLB) of from 7 to 15, more preferably of from 8 to 14, and most preferably of from 9 to 14, as determined by the Griffin method. As is known in the art, the HLB is a measure of the lipophilicity of the (first) surfactant based on an arbitrary scale of from 0 to 40, with higher values indicating a lower lipophilicity or greater hydrophilicity of the (first) surfactant.

Still further, it is contemplated that the (first) surfactant may have a critical micelle concentration (CMC) at 25° C. of from 0.1 to 5, of from 0.1 to 2, or of from 0.1 to 1, g/L, as determined by a surface tension method well known in the art. The (first) surfactant preferably has a critical micelle concentration (CMC) at 25° C. of from 0.01 to 5, of from 0.02 to 2, or of from 0.03 to 1, g/L, as determined by the surface tension method well known in the art. The method includes production of a graph of surface tension vs. log concentration of the (first) surfactant. The CMC is found as the point at which two lines intersect, i.e., the baseline of minimal surface tension and the slope where surface tension shows linear decline. To measure CMC, a surface or interfacial tensiometer equipped with an automated dosimeter is utilized. A probe is chosen (e.g., a Wilhelmy plate or DuNouy ring) and a measuring vessel is filled with solute. The automated dosimeter is filled with concentrated (first) surfactant. A surface tension of the solute is measured prior to any addition of the (first) surfactant to the solute. Subsequently, an addition of the (first) surfactant is made to the solute and surface tension is measured. Additions of the (first) surfactant to the solute are then continuously made, and surface tensions measured, such that data is evenly spaced along a log scale of concentration. As is known in the art, CMC is a measure of the concentration of the (first) surfactant that represents a critical value above which increasing concentration of the (first) surfactant forces formation of micelles. A decreased CMC is indicative of an ability of the (first) surfactant to form micelles in solution at minimized concentrations leading to increased cleaning ability and decreased cost of use.

In addition to the first surfactant, the cleaning formulation also includes the second surfactant. The second surfactant has the general formula $R^2$—O-(B)$_n$H. In this formula, $R^2$ is an aliphatic hydrocarbon having from 12 to 14 carbon atoms. It is contemplated that $R^2$ may include a mixture of different aliphatic hydrocarbons having 10, 12, 14, and/or 16 carbon atoms. Alternatively, $R^2$ may be an aliphatic hydrocarbon having 12 carbon atoms or 14 carbon atoms. Preferably, $R^2$ is an aliphatic hydrocarbon having 12 carbon atoms. In one embodiment, the second surfactant includes approximately 55 percent by weight of molecules wherein $R^2$ is an aliphatic hydrocarbon having 12 carbon atoms and approximately 45 percent of molecules wherein $R^2$ is an aliphatic hydrocarbon having 14 carbon atoms. In one embodiment, the second surfactant includes only molecules having 12 carbon atoms. An example of a particularly suitable hydrocarbon having 12 carbon atoms includes, but is not limited to, a dodecane moiety. It is to be understood that the terminology "dodecane moiety" refers to a $C_{12}H_{25}$ moiety bonded to the oxygen atom of the second surfactant. Preferably, the oxygen atom is bonded to a primary carbon atom of the dodecane moiety, i.e., in a 1-dodecanol structure. In another embodiment, the second surfactant is substantially free of aliphatic hydrocarbons having less than 12 carbon atoms and/or more than 14 carbon atoms. The terminology "substantially free" refers to an amount of hydrocarbons preferably of less than 10% by weight, more preferably of less than 5% by weight, and most preferably of less than 1% by weight, of the cleaning formulation.

It is contemplated that the aliphatic hydrocarbon having from 12 to 14 carbon atoms may have any average degree of branching. That is, the aliphatic hydrocarbon having from aliphatic hydrocarbon having from 12 to 14 carbon atoms may have an average degree of branching of zero or may have an average degree of branching of greater than zero. Preferably, the aliphatic hydrocarbon having from 8 to 11 carbon atoms has an average degree of branching of approximately zero.

Additionally, B is an alkyleneoxy group having from 2 to 5 carbon atoms and may be the same or may be different than A, first introduced above. Most preferably, B is an ethyleneoxy group (2 carbon atoms). Additionally, n is a positive number, may be any fraction or whole number greater than zero, and may be the same or different than m. In one embodiment, the second surfactant includes a mixture of molecules having differing numbers of moles of the alkyleneoxy group added to the aliphatic hydrocarbon molecules. In one embodiment, n may be a number of from 3 to 100, from 3 to 50, from 3 to 15, from 3 to 12, from 3 to 10, or from 5 to 10. When n is greater than or equal to 2, it is contemplated that the alkyleneoxy groups may be distributed randomly or blockwise. Additionally, the second surfactant is preferably present in the cleaning formulation in an amount of from 10 to 90, and more preferably of from 15 to 75, parts by weight per 100 parts by weight of the cleaning formulation.

The second surfactant preferably has both an aqueous cloud point and a solvent cloud point of from 25 to 80, more preferably of from 30 to 70, and most preferably of from 40 to 70° C. Further, the second surfactant preferably has a hydrophilic lipophilic balance (HLB) from 7 to 15, more preferably of from 8 to 14, and most preferably of from 9 to 14, as determined by the Griffin method. However, in one embodiment, the second surfactant preferably may have a hydrophilic lipophilic balance (HLB) from 7 to 15, from 9 to 14, or from 11 to 14, as determined by the Griffin method Still further, the second surfactant preferably has a CMC at 25° C. of from 0.0001 to 0.6, more preferably of from 0.002 to 0.3, and most preferably of from 0.002 to 0.06, g/L, as determined by a method well known in the art and described above.

In addition to the first and second surfactants, the cleaning formulation also includes a polyalkylene glycol. The polyalkylene glycol may be specifically added to the cleaning formulation or may be formed in situ while forming the first and or second surfactants. The polyalkylene glycol preferably includes, but is not limited to, polyethylene glycol (PEG), polypropylene glycol (PPG), polybutylene glycol (PBG), and combinations thereof. Most preferably, the polyalkylene glycol is further defined as polyethylene glycol. In one embodiment, the polyalkylene glycol may have any number average molecular weight up to approximately 12,000 g/mol. The polyalkylene glycol may have a number average molecular weight of from 200 to 12,000, from 300 to 3,000, from 300 to 2,000, from 400 to 2,000, from 300 to 1,000, from 400 to 1,000, from 400 to 800, from 600 to 800, or of approximately 700, g/mol. For descriptive purposes only, a chemical structure of polyethylene glycol having a number average weight of approximately 700 g/mol is shown below:

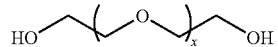

wherein x is an integer of approximately 9-22.

The polyalkylene glycol is present in an amount of from 3 to 20 parts by weight per 100 parts by weight of the cleaning formulation. More preferably, the polyalkylene glycol is present in an amount of from 5 to 15, and most preferably of from 8 to 10, parts by weight per 100 parts by weight of the surfactant composition. In one embodiment, the polyalkylene glycol is present in an amount of from 6 to 10 parts by weight per 100 parts by weight of the surfactant composition. In another embodiment, the surfactant composition includes from 18 to 19 parts by weight of the first surfactant, from 72 to 73 parts by weight of the second surfactant, and approximately 8 to 10 parts by weight of the polyalkylene glycol, per 100 parts by weight of the cleaning formulation. In another embodiment, the surfactant composition includes from 72 to 73 parts by weight of the first surfactant, from 18 to 19 parts by weight of the second surfactant, and approximately 8 to 10 parts by weight of the polyalkylene glycol, per 100 parts by weight of the surfactant composition.

In addition to the first surfactant, the second surfactant, and the polyalkylene glycol, the surfactant composition may also include, but does not require, an additional surfactant that is different from the first and second surfactants. If the additional surfactant is included in the surfactant composition, it may only be included in addition to both the first and second surfactants. In one embodiment, the surfactant composition includes a third surfactant and a fourth surfactant. In this embodiment, the third surfactant is different from the first surfactant and has the general formula: $R^1$—O-(A)$_m$H, wherein $R^1$, A, and m are the same as described above. Also in this embodiment, the fourth surfactant is different from the second surfactant and has the general formula: $R^2—O-(B)_nH$, wherein $R^2$, B, and n are the same as described above. It is contemplated that the surfactant composition may consist essentially of the first, second, third, and fourth surfactants. Alternatively, the surfactant composition may consist of the first, second, third, and fourth surfactants.

In yet another embodiment, the surfactant composition includes the third and fourth surfactants and a fifth and sixth surfactant. In this embodiment, the fifth surfactant is different from the first and third surfactants and has the same general formula as the third surfactant described immediately above. Also in this embodiment, the sixth surfactant is different from the second and fourth surfactants. The sixth surfactant also has the same general formula as the fourth surfactant described immediately above. It is contemplated that the surfactant composition may consist essentially of the first through sixth surfactants. Alternatively, the surfactant composition may consist of the first through sixth surfactants.

In still another embodiment, the additional surfactant may include, but is not limited to, aliphatic and/or aromatic alkoxylated alcohols, LAS (linear alkyl benzene sulfonates), paraffin sulfonates, FAS (fatty alcohol sulfates), FAES (fatty alcohol ethersulfates), and combinations thereof. Examples of suitable non-limiting additional surfactants include methylethylene glycols, butylethylene glycols, pentylethylene glycols, hexylethylene glycols, butylpropylene glycols, trimethylolpropane ethoxylates, glycerol ethoxylates, pentaerythritol ethoxylates, alkoxylates of bisphenol A, and alkoxylates of 4-methylhexanol and 5-methyl-2-propylheptanol.

It is also contemplated that in addition to, and different from the first through sixth surfactant, the surfactant composition may include other surfactants including non-ionic, cationic, anionic, and/or ampholytic surfactants. Suitable anionic surfactants include, but are not limited to, fatty alcohol sulfates of fatty alcohols having from 8 to 22, and more preferably from 10 to 18, carbon atoms, e.g., $C_9$-$C_{11}$ alcohol sulfates, $C_{12}$-$C_{14}$ alcohol sulfates, cetyl sulfate, myristyl sulfate, palmityl sulfate, stearyl sulfate, tallow fatty alcohol sulfate, and combinations thereof. Further non-limiting examples of suitable anionic surfactants include alkanesulfonates, such as $C_8$-$C_{24}$ alkylsulfonates, soaps such as alkali metal salts of $C_8$-$C_{24}$ carboxylic acids, $C_9$-$C_{20}$ linear alkylbenzenesulfonates, and $C_9$-$C_{20}$ linear alkyltoluenesulfonates. Still further, the anionic surfactant may include $C_8$-$C_{24}$ olefinsulfonates and di-sulfonates, mixtures of alkene- and hydroxyalkane-sulfonates or di-sulfonates, alkyl ester sulfonates, sulfonated polycarboxylic acids, alkyl glyceryl sulfonates, fatty acid glycerol ester sulfonates, alkylphenol polyglycol ether sulfates, paraffinsulfonates having from 20 to 50 carbon atoms, alkyl phosphates, acyl isothionates, acyl taurates, acyl methyl taurates, alkylsuccinic acids, alkenylsuccinic acids and corresponding esters and amides thereof, alkylsulfosuccinic acids and corresponding amides, mono- and di-esters of sulfosuccinic acids, acyl sarcosinates, sulfated alkyl polyglucosides, alkyl polyglycol carboxylates, hydroxyalkyl sarcosinates, and combinations thereof. The anionic surfactant may be a salt such as an alkali metal salt and/or an ammonium salt such as a hydroxyethylammonium, di(hydroxyethyl)ammonium, and/or tri(hydroxyethyl)ammonium salt. In one embodiment, the anionic surfactant is present in the cleaning formulation in an amount of from 3 to 30% by weight.

Suitable non-ionic surfactants include, but are not limited to, alkylphenol alkoxylates, alkyl polyglucosides, hydroxyalkyl polyglucosides, N-alkylglucamides, alkylene oxide block copolymers, polyhydroxy and polyalkoxy fatty acid derivatives, and combinations thereof. The alkylphenol alkoxylates may include alkylphenol ethoxylates having $C_6$-$C_{14}$ alkyl chains and from 5 to 30 moles of alkylene oxide added to the alkyl chains. The alkyl polyglucosides and/or hydroxyalkyl polyglucosides may have from 8 to 22 carbon atoms in an alkyl chain and have from 1 to 20 glucoside units. The N-alkylglucamides may have $C_6$-$C_{22}$ alkyl chains and may be formed from acylation of reductively aminated sugars with corresponding long-chain carboxylic acid derivatives. Further, the alkylene oxide block copolymers may include block copolymers of ethylene oxide, propylene oxide and/or butylene oxide. Still further, the polyhydroxy and/or polyalkoxy fatty acid derivatives may include polyhydroxy fatty acid amides, N-alkoxy- and/or N-aryloxy-polyhydroxy fatty acid amides, fatty acid amide ethoxylates, and also fatty acid alkanolamide alkoxylates. In one embodiment, the non-ionic surfactant is present in the cleaning formulation in an amount of from 1 to 20% by weight. In another embodiment, the additional surfactants include a mixture of anionic and non-ionic surfactants in a weight ratio from 95:5 to 20:80 and more preferably from 80:20 to 50:50.

Suitable cationic surfactants include, but are not limited to, interface-active compounds including ammonium groups such as alkyldimethylammonium halides and compounds having the chemical formula $RR'R''R'''N^+X^-$ wherein R, R', R'', and R''' are independently selected from the group of alkyl groups, aryl groups, alkylalkoxy groups, arylalkoxy groups, hydroxyalkyl(alkoxy) groups, and hydroxyaryl(alkoxy) groups and wherein X is an anion. In one embodiment, the cationic surfactant is present in the cleaning formulation in an amount of from 0.1 to 25 percent by weight.

Suitable ampholytic surfactants include, but are not limited to, aliphatic derivatives of secondary and/or tertiary amines which include an anionic group, alkyldimethylamine oxides, alkyl- and/or alkoxymethylamine oxides, and combinations thereof. In one embodiment, the ampholytic surfactant is present in the cleaning formulation in an amount of from 0.1 to 25 percent by weight of the cleaning formulation.

Once formed, the surfactant composition preferably has both an aqueous cloud point and a solvent cloud point of from 25 to 80, more preferably of from 30 to 70, and most preferably of from 40 to 70,° C. The surfactant composition can be a liquid, a solid, or a gel paste. The surfactant composition also preferably forms a contact angle with lime soap soil of from 30 to 90, more preferably of from 40 to 80, and most preferably of from 45 to 75, degrees, measured with a contact angle goniometer at a time of from 0.1 to 10 seconds. The lime soap soil used to determine contact angle is formed according to Chemical Specialty Products Association (CSPA) method DCC-16. To measure contact angle, the surfactant composition is present in an aqueous solution at a concentration of approximately 500 parts per million. The contact angle is determined by the method described in greater detail in the Examples below. Further, the surfactant composition preferably has a Draves Wetting value of less than 80, more preferably of less than 30, and most preferably of less than 20, seconds. The surfactant composition also preferably has a pH of from 5 to 8 and more preferably of from 6 to 7. It is to be appreciated that the pH of the surfactant composition may be the same or different from the pH of the cleaning formulation. In one embodiment, the surfactant composition may be neutralized with an organic or inorganic acid to a pH of about 7. In another embodiment, the surfactant composition is not neutralized.

The surfactant composition may be formed by any method known in the art. In one embodiment, the method includes the step of alkoxylating a first aliphatic alcohol having from 8 to 11 carbon atoms in the presence of a catalyst to form the first surfactant and the polyalkylene glycol in situ. Preferably, the catalyst is a metal catalyst, e.g., sodium hydroxide, which is described in greater detail below. As is known in the art, the terminology "in situ", relative to the step of alkoxylating the first aliphatic alcohol, refers to formation of the polyalkylene glycol in an original place, i.e., in the same reaction vessel as is used to form the first surfactant, and by the same reaction used to form the first surfactant.

The step of alkoxylating the first aliphatic alcohol preferably includes reacting a metal catalyst, i.e., a metal hydroxide catalyst, with the first aliphatic alcohol to form an alkoxide ($M^+O^-$). This step may be completed in the presence or absence of water. After the alkoxide is formed, the alkoxide is preferably reacted with an alkylene oxide to form the first surfactant and form the polyalkylene glycol in situ. For descriptive purposes only, a chemical reaction scheme of the alkoxylation of the first aliphatic alcohol to form the first surfactant and the polyalkyleneglycol is generically shown below:

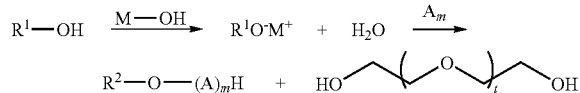

wherein t is a positive number.

The first aliphatic alcohol may include any aliphatic alcohol having from 8 to 11 carbon atoms. In one embodiment the first aliphatic alcohol includes a mixture of different aliphatic alcohols having 8, 9, 10, and/or 11 carbon atoms. Alternatively, the first aliphatic alcohol may have 8 carbon atoms, 9 carbon atoms, 10 carbon atoms, or 11 carbon atoms. Preferably, the first aliphatic alcohol has 10 carbon atoms and includes 2-propylheptanol. For descriptive purposes only, a chemical structure of 2-propylheptanol is shown below:

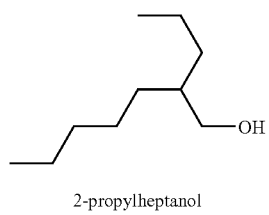

2-propylheptanol

The metal catalyst preferably includes an alkali metal or alkaline earth metal hydroxide, but may include any metal catalyst known in the art including transition metal organometallic catalysts. Particularly suitable alkali metal catalysts include, but are not limited to, sodium hydroxide, potassium hydroxide, rubidium hydroxide, cesium hydroxide, and combinations thereof. The metal catalyst may be a single metal catalyst or may include a mixture of metal catalysts, as determined by one of skill in the art.

In addition to the step of alkoxylating the first aliphatic alcohol, the method may also include the step of alkoxylating a second aliphatic alcohol having from 12 to 14 carbon atoms in the presence of the metal catalyst to form the second surfactant and the polyalkylene glycol in situ. As first described above, the terminology "in situ", relative to the step of alkoxylating the second aliphatic alcohol, refers to formation of the polyalkylene glycol in the original place, i.e., in the same reaction vessel as is used to form the second surfactant, and by the same reaction used to form the second surfactant.

The step of alkoxylating the second aliphatic alcohol includes reacting the catalyst with the second aliphatic alcohol to form an alkoxide. This step may also be completed in the presence or absence of water. After the alkoxide is formed, the alkoxide is reacted with an alkylene oxide to form the second surfactant and form the polyalkylene glycol in situ. For descriptive purposes only, a chemical reaction scheme of the alkoxylation of the second aliphatic alcohol to form the second surfactant and the polyalkyleneglycol is generically shown below:

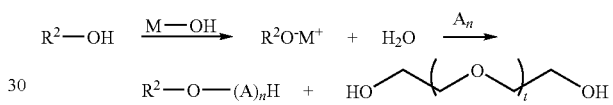

wherein t is a positive number.

The second aliphatic alcohol may include any aliphatic alcohol having from 12 to 14 carbon atoms. Preferably, the second aliphatic alcohol includes a mixture of different alcohols having 12, 13, and 14 carbon atoms. It is to be understood that the second aliphatic may have 12 carbon atoms or 13 carbon atoms, or 14 carbon atoms, or 12 to 14 carbon atoms, or 13 to 14 carbon atoms. In one embodiment, the second aliphatic alcohol has 13 carbon atoms and is commonly known as tridecyl alcohol. Preferably, the second aliphatic alcohol includes a mixture of 1-dodecanol and 1-tetradecanol in a ratio of from 5:95 to 95:5. More preferably, the second aliphatic alcohol includes a mixture of 1-dodecanol and 1-tetradecanol in a ratio of 55:45.

It is contemplated that the step of alkoxylating the first aliphatic alcohol may be completed separately from, or simultaneously with, the step of alkoxylating the second aliphatic alcohol. Also, the first and second aliphatic alcohols may be alkoxylated in the same vessel or in different vessels. Preferably, the first and second aliphatic alcohols are alkoxylated simultaneously in the same vessel. It is contemplated that if the first and second alcohols are alkoxylated simultaneously in the same vessel, then the polyalkylene glycol formed in situ may be formed from one or both of the reactions to form the first surfactant and/or the second surfactant.

The steps of alkoxylating the first and second aliphatic alcohols may be completed at any temperature and at any pressure. Preferably, these steps are completed at a temperature of from 100° C. to 160° C. and at a pressure of from 20 psig to 100 psig. For descriptive purposes only, a preferred chemical reaction scheme including the ethoxylation of the first and second aliphatic alcohols in the presence of potassium hydroxide as the metal catalyst, to form the polyethylene glycol in situ, is shown below:

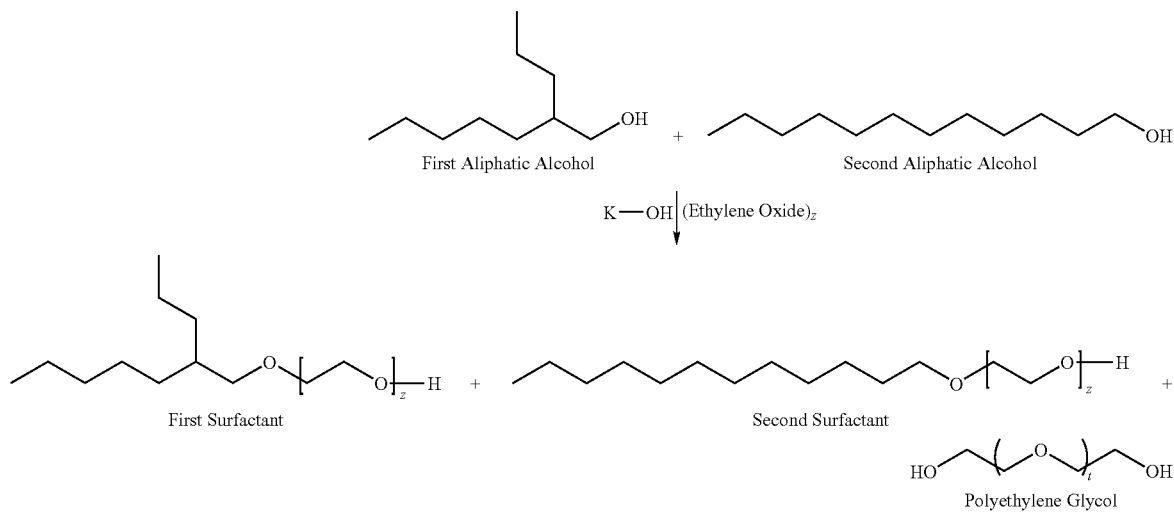

wherein z is a number of from 5 to 12 and t is a number of from 22-24.

In addition to including the surfactant composition, the cleaning formulation may also include, but is not limited to, water, builders, bleaches, enzymes, solvents, salts, graying inhibitors, soil release polymers, color transfer inhibitors, foam inhibitors, complexing agents, optical brighteners, fragrances, fillers, inorganic extenders, formulation auxiliaries, solubility improvers, opacifiers, dyes, corrosion inhibitors, peroxide stabilizers, electrolytes, water, soaps, detergents, acids such as phosphoric acid, amidosulfonic acid, citric acid, lactic acid, acetic acid, peracids, and trichloroisocyanuric acid, solvents such as ethylene glycol, 2-butoxyethanol, butyldiglycol, alkyl glycol ethers, and isopropanol, chelating agents such as EDTA, NTA (N,N,N-nitrilotriacetic acid), and MGDA (2-methylglycine-N,N-diacetic acid), phosphonates, polymers, such as polyacrylates, copolymers of maleic acid and acrylic acid, alkali donors such as alkaline and alkaline earth metal hydroxides, amines, silicates, carbonates, phosphates, amides, Group 1 salts of carbanions, amides, and hydrides, perfumes, oils, oxidizing agents such as perborates, dichloroisocyanurates, enzymes, interface-active ethyleneoxy adducts, and combinations thereof. Although the cleaning formulation may include any amount of water, as determined by one of skill in the art, the water is preferably included in an amount of from 5 to 95% by weight, more preferably of from 10 to 90% by weight, still more preferably of from 50 to 90% by weight, and most preferably of from 70 to 90% by weight, of the cleaning formulation.

Particularly suitable builders include both inorganic and organic builders. Preferably, the inorganic builders include crystalline and/or amorphous alumosilicates with ion-exchanging properties, such as zeolites. Various types of zeolites may be used including, but not limited to, A, X, B, P, MAP and HS zeolites in sodium form or in forms in which sodium is partially exchanged for lithium, potassium, calcium, magnesium, and/or ammonium. In one embodiment, the inorganic builders include carbonates and hydrogencarbonates as alkali metal salts, alkaline earth metal salts, and/or ammonium salts. Alternatively, the inorganic builder may include polyphosphates such as pentasodium triphosphate. One or more inorganic builders may be present in the cleaning formulation in any amount or any ratio. Preferably, the inorganic builder includes a mixture of alumosilicates and carbonates in a weight ratio of 98:2 to 20:80 and more preferably of 85:15 to 40:60. Alternatively, the inorganic builder may be present in the cleaning formulation in an amount of from 5 to 50% by weight.

The organic builders preferably include di-silicates and/or sheet silicates that may include alkali metal silicates, alkaline earth metal silicates, and/or ammonium silicates. Amorphous silicates such as sodium metasilicate may also be used. In one embodiment, the organic builder includes an acid selected from the group of carboxylic acids, copolymers of carboxylic acids, terpolymers of carboxylic acids, graft polymers of carboxylic acids, polyglyoxylic acids, polyamidocarboxylic acids, phosphonic acids, and combinations thereof.

Particularly suitable carboxylic acids include $C_4$-$C_{20}$ di-, tri- and tetra-carboxylic acids such as succinic acid, propanetricarboxylic acid, butanetetracarboxylic acid, and cyclopentanetetracarboxylic acid, $C_4$-$C_{20}$ hydroxycarboxylic acids such as malic acid, tartaric acid, gluconic acid, glutaric acid, citric acid, and lactobionic acid, sucrose mono-, di- and tricarboxylic acids, alkyl- and alkenyl-succinic acids having $C_2$-$C_{16}$ alkyl and/or alkenyl radicals, aminopolycarboxylic acids such as nitrilotriacetic acid, 3-alaninediacetic acid, ethylenediaminetetraacetic acid, serinediacetic acid, isoserinediacetic acid, methylglycinediacetic acid and alkylethylenediamine triacetates, oligomaleic acids, co- and terpolymers of unsaturated $C_4$-$C_8$ dicarboxylic acids such as maleic acid, fumaric acid, itaconic acid and citraconic acid, monoethylenically unsaturated $C_3$-$C_8$ monocarboxylic acids such as acrylic acid, methacrylic acid, crotonic acid and vinylacetic acid, and combinations thereof.

Examples of suitable copolymers of dicarboxylic acids include, but are not limited to, copolymers of maleic acid and acrylic acid in a weight ratio of 100:90 to 95:5 and more preferably of 30:70 to 90:10 with molar masses from 100,000 to 150,000, and copolymers of maleic acid with $C_2$-$C_8$ olefins in a molar ratio 40:60 to 80:20. A non-limiting example of a suitable terpolymer of the carboxylic acids includes a terpolymer of maleic acid, acrylic acid and a vinyl ester of a $C_1$-$C_3$ carboxylic acid in a weight ratio of 10 (maleic acid): 90 (acrylic acid+vinyl ester): 95 (maleic acid): 10 (acrylic acid+vinyl ester), where the weight ratio of acrylic acid to the vinyl ester can be from 30:70 to 70:30.

Suitable examples of graft polymers of carboxylic acids include a graft base and an unsaturated carboxylic acid. The carboxylic acid may include, but is not limited to, maleic acid, fumaric acid, itaconic acid, citraconic acid, acrylic acid, methacrylic acid, crotonic acid vinylacetic acid, and combinations thereof. Suitable graft bases included in the graft polymers of the carboxylic acids include degraded polysaccharides such as acidically and/or enzymatically degraded starches, inulins, cellulose, protein hydrolysates, reduced degraded polysaccharides such as mannitol, sorbitol, aminosorbitol and N-alkylglucamine, alkylene oxide block copolymers such as ethylene oxide/propylene oxide block copolymers, ethylene oxide/butylene oxide block copolymers, ethylene oxide/propylene oxide/butylene oxide block copolymers, and alkoxylated mono- or polyhydric $C_1$-$C_7$ alcohols and/or $C_{15}$-$C_{22}$ alcohols that are different from the first and second surfactants. It is to be understood that if alkoxylated mono- or polyhydric $C_1$-$C_7$ alcohols and/or $C_{15}$-$C_{22}$ alcohols are included in the cleaning formulation, these alkoxylated alcohols are not equivalent to the first and second surfactants and may only be included in addition to the first and second surfactants. In one embodiment, 20 to 80 parts by weight of the carboxylic acid per 100 parts by weight of the graft base, may be polymerized. In this embodiment, a mixture of maleic acid and acrylic acid in the weight ratio from 90:10 to 10:90 is preferably polymerized with the graft base.

Additionally, the organic builder may include a polyaspartic acid or a co-condensate of aspartic acid with one or more amino acids including, but not limited to, $C_4$-$C_{25}$ mono- or di-carboxylic acids and/or $C_4$-$C_{25}$ mono- or di-amines. In one embodiment, the co-condensate includes a polyaspartic acid modified with $C_6$-$C_{22}$ mono- or di-carboxylic acids or with $C_6$-$C_{22}$ mono- or di-amines in acids including phosphorous.

Further, the organic builder may include a condensation product of citric acid and a hydroxycarboxylic acid or a polyhydroxy compound. Most preferably, the condensation products of citric acid include carboxyl groups and have number average molecular weights of up to 10,000 g/mol. Still further, the organic builder may include ethylenediaminedisuccinic acid, oxydisuccinic acid, aminopolycarboxylates, aminopolyalkylene phosphonates, polyglutamates, and combinations thereof. Also, a non-limiting example of a suitable phosphonic acid includes hydroxyethanediphosphonic acid.

Alternatively, the organic builder may be selected from the group of olefins, ethers, esters, amines, oxidized starches, and combinations thereof. Suitable olefins, ethers, esters, and amines include, but are not limited to, monoethylenically unsaturated $C_2$-$C_{22}$ olefins, vinyl alkyl ethers with $C_1$-$C_8$ alkyl groups, styrene, vinyl esters of $C_1$-$C_8$ carboxylic acids, (meth)acrylamide and vinylpyrrolidone, (meth)acrylic esters of $C_1$-$C_8$ alcohols, (meth)acrylonitrile, (meth)acrylamides of $C_1$-$C_8$ amines, N-vinylformamide and vinylimidazole. In one embodiment, the organic builder is present in the cleaning formulation in an amount of from 0.1 to 20% by weight.

The cleaning formulation may also include a bleach, as first introduced above. The bleach may include, but is not limited to, alkali metal perborates, alkali metal carbonate perhydrates, peracids, hypochlorites, and combinations thereof. Suitable examples of peracids include, but are not limited to, peracetic acid, $C_1$-$C_{12}$ percarboxylic acids, $C_8$-$C_{16}$ dipercarboxylic acids, imidopercaproic acids, aryldipercaproic acids, linear and branched octane-, nonane-, decane- or dodecane-monoperacids, decane- and dodecane-diperacid, mono- and di-perphthalic acids, isophthalic acids and terephthalic acids, phthalimidopercaproic acid, terephthaloyldipercaproic acid, polymeric peracids, salts thereof, and combinations thereof. The bleach may be present in the cleaning formulation in an amount of from 0.5 to 30% by weight.

The cleaning formulation may also include a bleach activator present in an amount of from 0.1 to 15% by weight. The bleach activator may include, but is not limited to, polyacylated sugars, e.g., pentaacetylglucose, acyloxybenzenesulfonic acids and alkali metal and alkaline earth metal salts thereof, e.g., sodium p-isononanoyloxybenzenesulfonate and sodium p-benzoyloxybenzenesulfonate, N,N-diacetylated and N,N,N',N'-tetraacylated amines, e.g., N,N,N',N'-tetraacetylmethylenediamine and -ethylenediamine (TAED), N,Ndiacetylaniline, N,N-diacetyl-p-toluidine or 1,3-diacylated hydantoins, such as 1,3-diacetyl-5,5-dimethylhydantoin, N-alkyl-N-sulfonylcarboxamides, e.g., N-methyl-N-mesylacetamide and N-methyl-N-mesylbenzamide, N-acylated cyclic hydrazides, acylated triazoles and urazoles, e.g., monoacetylmaleic acid hydrazide, O,N,N-trisubstituted hydroxylamines, e.g., O-benzoyl-N,N-succinylhydroxylamine, O-acetyl-N,N-succinylhydroxylamine and O, N,N-triacetylhydroxylamine, N,N'-diacylsulfurylamides, e.g., N,N'-dimethyl-N,N'-diacetylsulfurylamide and N,N'-diethyl-N,N'-dipropionylsulfurylamide, triacyl cyanurates, e.g., triacetyl cyanurate and tribenzoyl cyanurate, carboxylic anhydrides, e.g., benzoic acid anhydride, m-chlorobenzoic anhydride and phthalic anhydride, 1,3-diacyl-4,5-diacyloxy-imidazolines, e.g., 1,3-diacetyl-4,5-diacetoxyimidazoline, tetraacetylglycoluril, tetrapropionylglycoluril, diacylated 2,5-diketopiperazines, e.g., 1,4-diacetyl-2,5-diketopiperazine, acylation products of propylenediurea and 2,2-dimethylpropylenediurea, e.g., tetraacetylpropylenediurea, a-acyloxypolyacylmalonamides, e.g., a-acetoxy-N,N'-diacetylmalonamide, diacyldioxohexahydro-1,3,5-triazines, e.g., 1,5-diacetyl-2,4-dioxohexahydro-1,3,5-triazine, benz (4H)-1,3-oxazin-4-ones with alkyl radicals, e.g., methyl, or aromatic radicals, and combinations thereof.

The bleach may also be combined with a bleach catalyst. The bleach catalyst may include, but is not limited to, quaternized imines, sulfonimines, manganese complexes, and combinations thereof. The bleach catalyst may be included in the cleaning formulation in amounts up to 1.5% by weight.

The cleaning formulation may also include an enzyme, as introduced above. The enzyme may include, but is not limited to, proteases such as Savinase® and Esperase®, lipases such as Lipolase®, cellulases such as Celluzym, and combinations thereof. Each of the Savinase®, Esperase®, Lipolase®, and Celluzym are commercially available from Novo Nordisk of Princeton, N.J. In one embodiment, the cleaning formulation includes an enzyme present in an amount of from 0.1 to 4% by weight.

Suitable graying inhibitors include, but are not limited to, polyesters of polyethylene oxides with ethylene glycol and/or propylene glycol and aromatic dicarboxylic acids or aromatic and aliphatic dicarboxylic acids, polyesters of polyethylene oxides terminally capped at one end with di- and/or polyhydric alcohols or dicarboxylic acids, and combinations thereof. Suitable soil release polymers include, but are not limited to, amphiphilic graft polymers or copolymers of vinyl esters and/or acrylic esters onto polyalkylene oxides or modified celluloses, such as methylcellulose, hydroxypropylcellulose, and carboxymethylcellulose, and combinations thereof. In one embodiment, the cleaning formulation includes the soil release polymer present in an amount of from 0.3 to 1.5% by weight. Suitable color transfer inhibitors include, but are not limited to, color transfer inhibitors, for example homopolymers and copolymers of vinylpyrrolidone, of vinylimidazole, of vinyloxazolidone and of 4-vinylpyridine N-oxide having number average molecular weights of from 15,000 to 100,000 g/mol. In one embodiment, the cleaning formulation includes the color transfer inhibitor present in an amount of from 0.05 to 5% by weight. Suitable foam inhibitors include, but are not limited to, organopolysiloxanes, silica, paraffins, waxes, microcrystalline waxes, and combinations thereof.

The cleaning formulation preferably has a pH of greater than 10. In one embodiment, the cleaning formulation has a pH of from 10-12. In another embodiment, the cleaning formulation has a pH of from 12-14. The surfactant composition, included in the cleaning formulation, preferably has a pH of from 5 to 8 and more preferably of from 6 to 7.

It is also contemplated that the cleaning formulation and/or the surfactant composition may exhibit a mean percent cleaning, of from 40 to 100, more preferably of from 60 to 100, still more preferably of from 70 to 100, and most preferably of from 80 to 100, percent, as determined in tergotometer tests, scrub tests, and spray tests. The mean percent clean in these tests is determined by the methods described in greater detail in the Examples below.

Referring back to the method, as first introduced above, the method includes the step of applying the cleaning formulation to the surface, as set forth in FIGS. 1-4. The step of applying the cleaning formulation to the surface may be undertaken by any method known in the art. It is contemplated that the step of applying the cleaning formulation to the surface may be further defined as exposing the surface to the cleaning formulation. If the surface is a textile, the step of applying the cleaning formulation may be further defined as flushing the textile with the cleaning formulation, as set forth in FIGS. 2-4. As is known in the art, "flushing," or the step of flushing, may include contacting the textile with the cleaning formulation. In one embodiment, flushing includes an initial wetting step in a washing machine. In another embodiment, the cleaning formulation is applied in a flushing step before a rinse formulation is applied, as described in greater detail below. It is contemplated that the step of flushing may occur once, twice, or multiple times. It is contemplated that the step of flushing may include separating loose soil from the textile. As is also known in the art, flushing may be known as pre-soaking, pre-flushing, and/or pre-washing. The step of applying the cleaning formulation preferably occurs for a time of less than three minutes and more preferably for about two minutes. However, this step may continue for any amount of time selected by one of skill in the art to achieve the desired objective. In one embodiment, the step of flushing occurs three times for a total of about six minutes.

As described above, the cleaning formulation may have a pH of greater than 10. If so, the method preferably includes the step of applying the cleaning formulation having the pH of greater than 10. As known in the art of laundering textiles, this step is known as "breaking" or as a "break step," as set forth in FIGS. 2-4. Typically, a break step includes use of alkali salts to enhance stain removal and assist with microbial kill. If the surface includes a textile and the method includes this step, this step preferably occurs for a time of less than thirteen minutes and more preferably for a time of from eight to twelve minutes. In one embodiment, the step of breaking occurs for about twelve minutes. However, this step may continue for any amount of time selected by one of skill in the art to achieve the desired objective.

The method may also include the step of sudsing the cleaning formulation. As is known in the art, "sudsing" includes cleaning the surface with the cleaning formulation, e.g., washing a textile. The step of sudsing may occur in a consumer and/or commercial washing machine and may occur at any point in the method. In one embodiment, the method includes the step of sudsing the cleaning formulation after the step of flushing. In another embodiment, the method includes the step of sudsing after the step of breaking. Alternatively, the method may include the step of sudsing after both the steps of flushing and breaking. The step of sudsing preferably occurs for a time of less than seven minutes and more preferably for a time of from four to six minutes. In one embodiment, this step occurs for about four minutes. However, this step may continue for any amount of time selected by one of skill in the art to achieve the desired objective.

The method also includes the step of providing a rinse formulation. The rinse formulation may be the same as the cleaning formulation or may be different. In one embodiment, the rinse formulation comprises water. In another embodiment, the rinse formulation consists essentially of water. In yet another embodiment, the rinse formulation consists of water. The water may be purified water, tap water, or hard water, as defined in the art. It is contemplated that the step of applying the rinse formulation to the surface may be further defined as exposing the surface to the rinse formulation.

In one embodiment, the method also includes the step of applying the rinse formulation to the surface, commonly known as rinsing. This step may include contacting the surface with the rinse formulation to at least partially remove the cleaning formulation from the surface. Alternatively, this step may occur before the step of applying the cleaning formulation to the surface. The step of applying the rinsing composition may occur once, twice, or multiple times, i.e., more than once. In one embodiment, the step of applying the rinse formulation includes rinsing the surface with tap water to remove the cleaning formulation. It is contemplated that this step may occur as part of a rinse cycle in a consumer or commercial washing machine. The step of applying the rinse formulation preferably occurs for a time of less than three minutes and more preferably for a time of about two minutes. However, this step may continue for any amount of time selected by one of skill in the art to achieve the desired objective.

Figure 2:
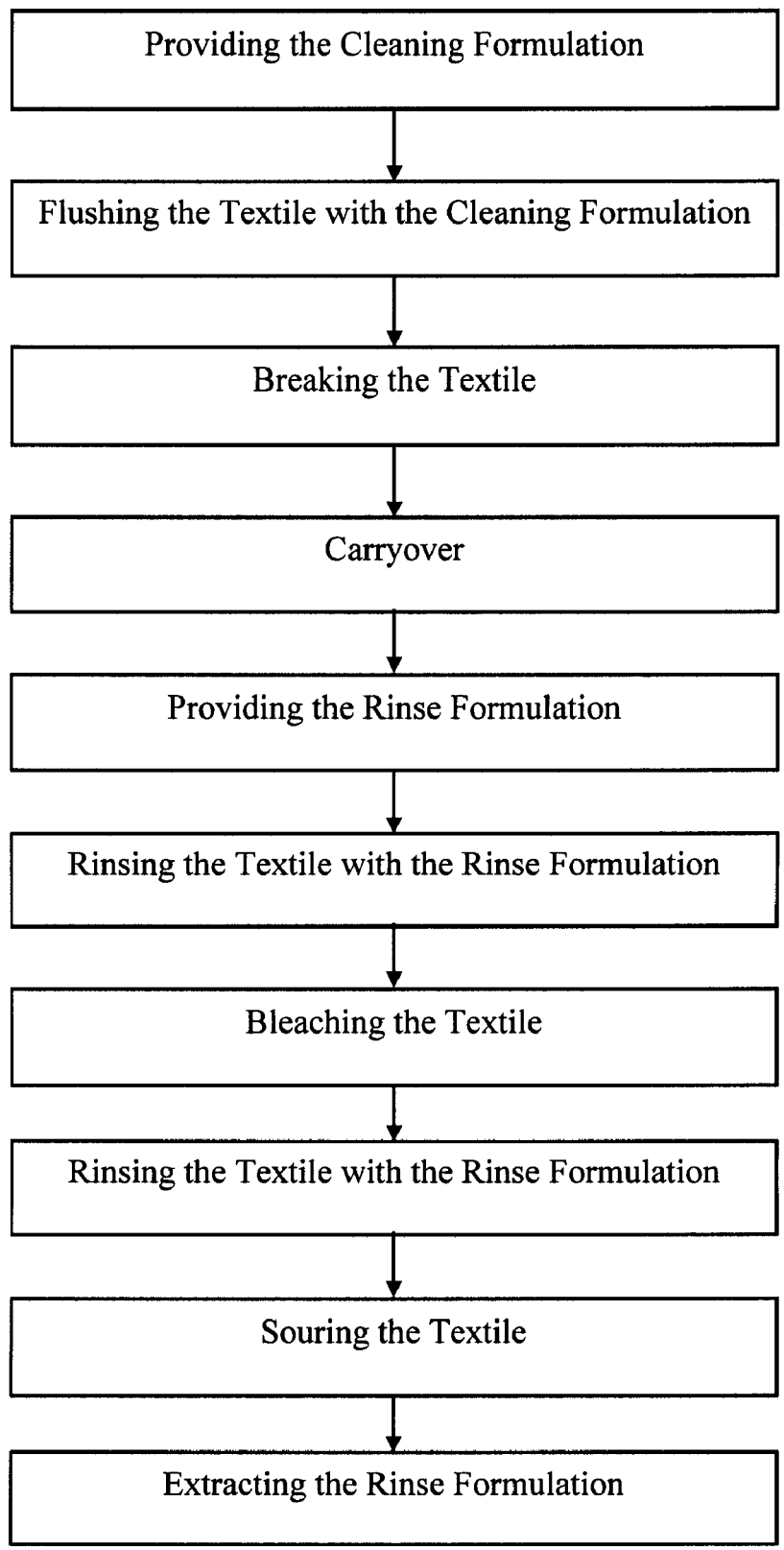
FIG. 2 is a block diagram illustrating the steps of a second embodiment of the instant invention.

Further, the method may include the step of bleaching the surface, as set forth in FIG. 2. The step of bleaching may occur at any point in the method. As is known in the art, the step of bleaching the surface includes applying a bleach to the surface, as described above. In one embodiment, the step of bleaching occurs after the step of applying the cleaning formulation, as also set forth in FIG. 2. The step of bleaching preferably occurs for a time of less than eleven minutes and may occur for a time of from eight to ten minutes. In one embodiment, this step continues for about ten minutes. However, this step may continue for any amount of time selected by one of skill in the art to achieve the desired objective.

Figure 3:
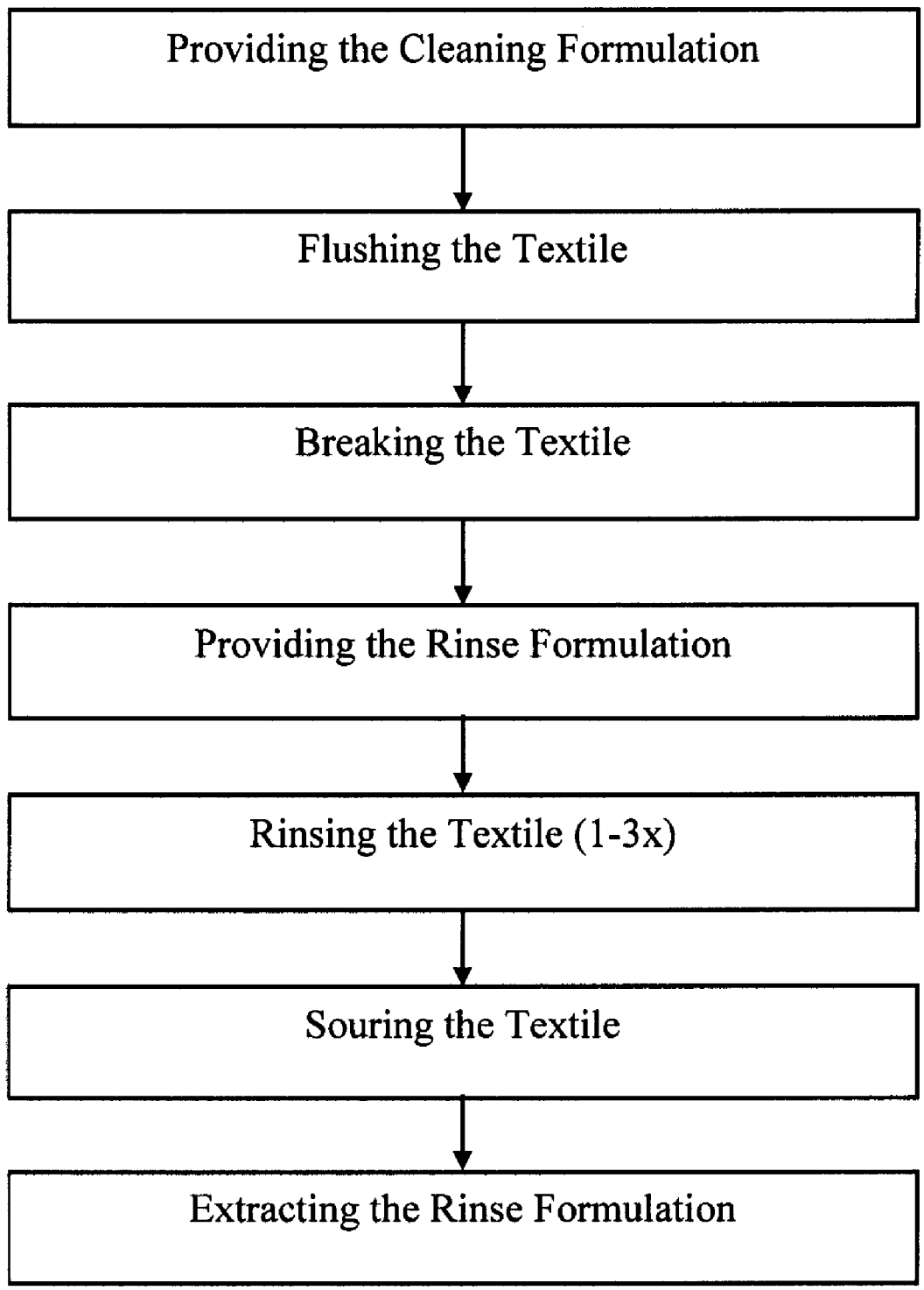
FIG. 3 is a block diagram illustrating the steps of a third embodiment of the instant invention.
Figure 4:
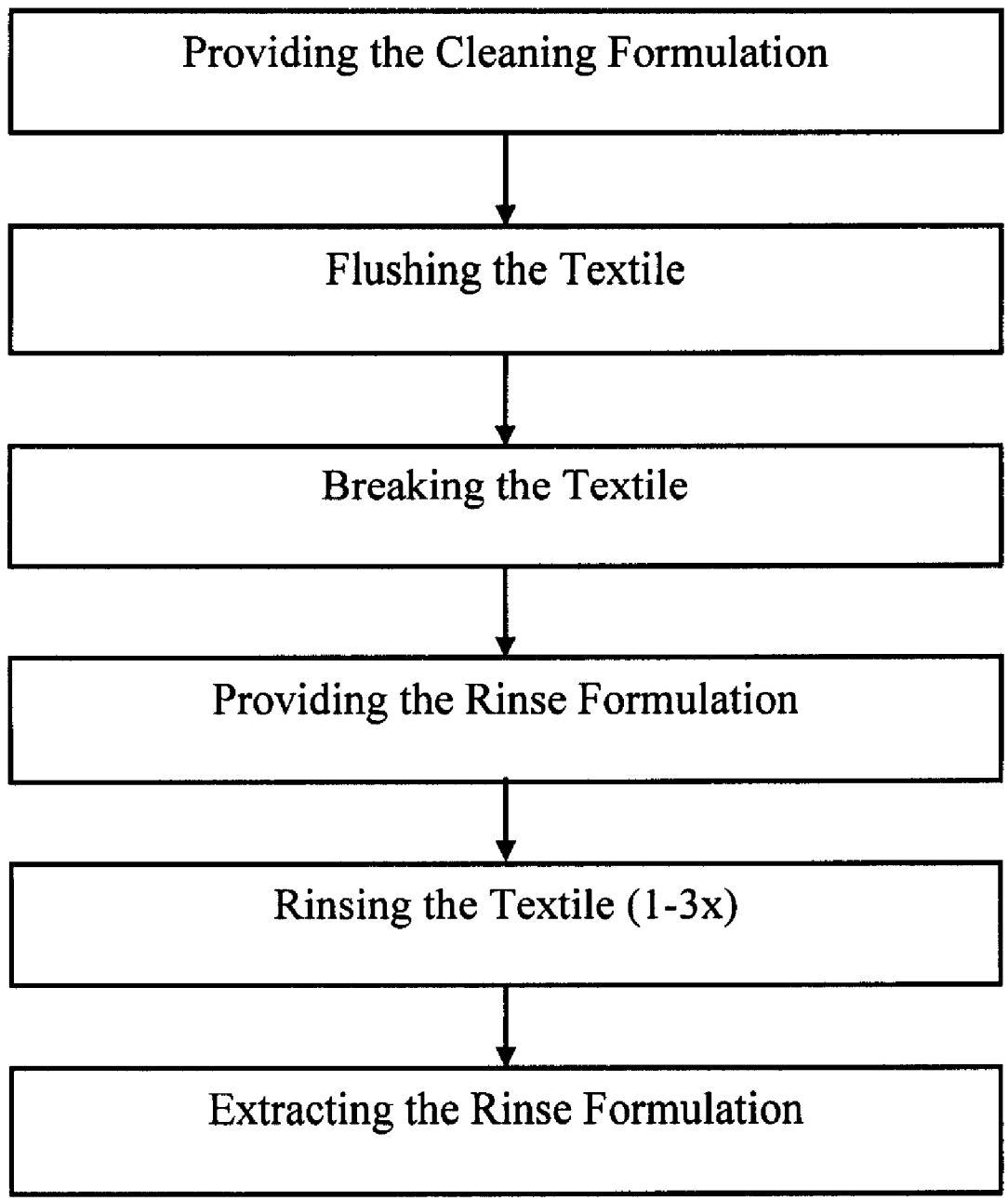
FIG. 4 is a block diagram illustrating the steps of a fourth embodiment of the instant invention.

The method may also include the step of souring the surface, which may occur at any point in the method, as set forth in FIGS. 2 and 3. As is known in the art, the step of souring includes adding an acid to the cleaning formulation and/or rinse formulation to neutralize alkalinity. The acid may be any known in the art. In one embodiment, the step of souring includes adding at least one of a softener, an optical brightener, and an antistatic agent to the cleaning formulation and/or rinse formulation. In one embodiment, the step of souring occurs after the cleaning formulation, having a pH of greater than 10, is applied. The step of souring preferably occurs for a time of less than thirteen minutes and more preferably from one half to twelve minutes. In one embodiment, this step continues for about two minutes. However, this step may continue for any amount of time selected by one of skill in the art to achieve the desired objective.

It is contemplated that the method may also include the step of extracting the rinse formulation from the surface. In one embodiment, the step of extracting may be completed through use of gravity and/or centrifugal force and may follow the step of applying the rinse formulation one or more times, as set forth in FIGS. 2-4. In another embodiment, the step of extracting the rinse formulation includes engaging a "spin cycle" in a consumer and/or commercial washing machine. The step of extracting the rinse formulation from a textile preferably occurs for a time of from two to eight and more preferably of from one-half to two, minutes. However, this step may continue for any amount of time selected by one of skill in the art to achieve the desired objective.

The method may also include the step of draining the cleaning formulation. As is known in the art of laundering textiles, the step of draining the cleaning formulation from the textile may be accomplished by gravity and/or centrifugal force. In one embodiment, the step of draining follows the step of sudsing. In another embodiment, the step of draining occurs between multiple occurrences of the step of flushing. The step of draining the cleaning formulation from the textile preferably occurs for a time of from two to eight and more preferably of from one-half to two, minutes. However, this step may continue for any amount of time selected by one of skill in the art to achieve the desired objective.

Further, the method may also include a carryover step, as set forth in FIG. 2. As is known in the art of laundering textiles, a carryover step is similar to the step of flushing but includes less water and an increased amount of the cleaning formulation. Without intending to be bound by any particular theory, it is believed that the carryover step lengthens a time of contact between the surface and the cleaning formulation and also adjusts a pH of the cleaning formulation and/or rinse formulation. It is also believed that the carryover step lowers a content of soil in the cleaning formulation and/or rinse formulation. It is contemplated that the carryover step may occur simultaneously with or as part of the sudsing step. The carryover step preferably occurs for a time of less than seven minutes and more preferably for a time of from four to six minutes. In one embodiment, this step occurs for about four minutes. However, this step may continue for any amount of time selected by one of skill in the art to achieve the desired objective.

The method may also include the step of softening the cleaning formulation and/or rinse formulation. As is known in the art, the step of softening includes adding a softener to the cleaning formulation and/or rinse formulation to reduce the pH of the cleaning formulation and/or rinse formulation. If included, the step of softening is different from the step of souring. It is contemplated that the softener may be any known in the art.

The method may further include the step of oiling the surface. If included in the method, this step preferably includes adding an oil to the surface and/or textile to increase affinity of the surface for additional soil and/or stains. As is known in the art, the step of oiling may be used when the surface is further defined as a textile, e.g., in "bar mop" applications.

The method may also include the step of starching the surface. It is contemplated that this step may include applying a starch to the surface and/or textile. The step of starching may occur as part of the step of souring or occur simultaneously with the step of souring. Alternatively, the step of starching may occur separately. The step of starching preferably occurs for a time of less than thirteen minutes and more preferably from one half to twelve minutes. In one embodiment, this step continues for about two minutes. However, this step may continue for any amount of time selected by one of skill in the art to achieve the desired objective.

In one embodiment, the method of washing the surface includes the steps of providing the cleaning formulation including surfactant composition including the first surfactant having the general formula: $R^1-O-(A)_m H$. In this formula, $R^1$ is a 2-propylheptane moiety, A is an ethyleneoxy group, and m is a number of from 3 to 12. In this embodiment, the surfactant composition also includes the second surfactant having the general formula: $R^2-O-(B)_n H$. In this formula, $R^2$ is an aliphatic hydrocarbon having from 12 to 14 carbon atoms, B is an ethyleneoxy group, and n is an number of from 3 to 12. Additionally, in this embodiment, the surfactant composition includes the polyalkylene glycol having a number average molecular weight of from 300 to 2,000 g/mol and present in an amount of from 8 to 10 parts by weight per 100 parts by weight of the cleaning formulation. Further, in this embodiment, the method includes the steps of providing the rinse formulation, applying the cleaning formulation to the surface, and applying the rinse formulation to the surface.

The instant invention also provides a method for treating a stain on the textile. In one embodiment, the method includes the aforementioned step of providing the cleaning formulation including the surfactant composition including the first surfactant having the general formula: $R^1-O-(A)_m H$, wherein $R^1$ is an aliphatic hydrocarbon having from 8 to 11 carbon atoms, A is an alkyleneoxy group having from 2 to 5 carbon atoms, and m is a positive number. In this embodiment, the surfactant composition also includes the second surfactant having the general formula: $R^2-O-(B)_n H$, wherein $R^2$ is an aliphatic hydrocarbon having from 12 to 14 carbon atoms, B is an alkyleneoxy group having from 2 to 5 carbon atoms, and n is a positive number. Further, in this embodiment, the surfactant composition includes the polyalkylene glycol present in an amount of from 3 to 20 parts by weight per 100 parts by weight of the cleaning formulation. Still further, in this embodiment, the method includes the steps of providing a rinse formulation, flushing the textile with the cleaning formulation, sudsing the cleaning formulation to treat the stain, as described above, and rinsing the textile with the rinse formulation.

In another embodiment, the method for treating the stain includes the steps of providing the cleaning formulation having a pH of greater than 10 and including the surfactant composition consisting essentially of the first surfactant, the second surfactant, and the polyalkylene glycol. In this embodiment, the first surfactant has the general formula: $R^1-O-(A)_m H$, wherein $R^1$ is a 2-propylheptane moiety, A is an ethyleneoxy group, and m is a number of from 3 to 12. Also in this embodiment, the second surfactant has the general formula: $R^2-O-(B)_n H$, wherein $R^2$ is an aliphatic hydrocarbon having from 12 to 14 carbon atoms, B is an ethyleneoxy group, and n is an number of from 3 to 12. Further, in this embodiment, the polyalkylene glycol has a number average molecular weight of from 300 to 2,000 g/mol and is present in an amount of from 8 to 10 parts by weight per 100 parts by weight of the cleaning formulation. Still further, in this embodiment, the method includes the steps of providing the rinse formulation consisting essentially of water, sudsing the cleaning formulation to treat the stain, and rinsing the textile with the rinse formulation. This embodiment may also include the step of bleaching the textile and/or any of the other aforementioned steps.

In yet another embodiment, the method includes the following steps in order: flushing, breaking, carryover, rinsing, bleaching, rinsing, souring, and extracting. In a further embodiment, the method includes the following steps in order: breaking, carryover, rinsing one to three times, souring, and extracting. It is also contemplated that the method may include the following steps in order: flushing, breaking, rinsing, and extracting. In all embodiments of the instant invention, it is contemplated that the method may be operated in a continuous mode, semi-continuous mode, batch mode, or semi-batch mode and may be operated in commercial and/or residential settings. It is contemplated that the entire method may occur in a time of from less than one minute to 45 minutes. However, it is to be appreciated that the method is not limited by a time needed for completion.

EXAMPLES

A series of surfactant compositions (Surfactant Compositions 1-13) are formed according to the present invention. Specifically, amounts of two of the First, Second, Third, and/or Fourth Aliphatic Alcohols are added to a vessel and mixed. Subsequently, potassium hydroxide (KOH) as the Metal Catalyst is added to the vessel and mixed with the two Aliphatic Alcohols to form a mixture. The mixture is heated to 85° C. and agitated for 1 hour. Subsequently, the mixture is heated to 110° C. and adjusted to a pressure of approximately 90 psig. Then, Ethylene Oxide is added to the mixture to react with the two Aliphatic Alcohols, thereby forming Surfactants and forming the Polyethylene Glycol in situ. The Ethylene Oxide is added to the mixture at a rate of approximately 1100-1200 gm/hr while the temperature of the mixture is allowed to increase to approximately 145° C. After formation of the Surfactants and Polyethylene Glycol, the temperature of the reaction vessel is lowered to approximately 80° C.

Amounts of each of the Metal Catalyst, the Aliphatic Alcohols, and the Ethylene Oxide, used to form the Surfactant Compositions 1-13, are set forth in Table 1 below, wherein all amounts are in grams unless otherwise indicated.

TABLE 1

| Components | Surfactant Composition 1 | Surfactant Composition 2 | Surfactant Composition 3 | Surfactant Composition 4 |
| --- | --- | --- | --- | --- |
| First Aliphatic Alcohol | 1260 | 400 | 345 | 1260 |
| Second Aliphatic Alcohol | 315 | 1600 | 1380 | 5040 |
| Third Aliphatic Alcohol | — | — | — | — |
| Fourth Aliphatic Alcohol | — | — | — | — |
| Metal Catalyst | 18 | 22 | 20 | 61 |
| Ethylene Oxide | 3775 | 3753 | 3640 | 8130 |
| Weight Percent of First Aliphatic Alcohol | 80 | 20 | 20 | 20 |
| Weight Percent of Second Aliphatic Alcohol | 20 | 80 | 80 | 80 |
| Moles of Ethylene Oxide Added to Reaction | 9 | 8 | 9 | 5.5 |

| Components | Surfactant Composition 5 | Surfactant Composition 6 | Surfactant Composition 7 | Surfactant Composition 8 |
| --- | --- | --- | --- | --- |
| First Aliphatic Alcohol | 4800 | 1200 | 6400 | — |
| Second Aliphatic Alcohol | 1200 | 4800 | 1600 | 500 |
| Third Aliphatic Alcohol | — | — | — | 1500 |
| Fourth Aliphatic Alcohol | — | — | — | — |
| Metal Catalyst | 74 | 39 | 60 | 10 |
| Ethylene Oxide | 9585 | 4360 | 10224 | 2646 |
| Weight Percent of First Aliphatic Alcohol | 80 | 20 | 80 | 25 |
| Weight Percent of Second Aliphatic Alcohol | 20 | 80 | 20 | 75 |
| Moles of Ethylene Oxide Added to Reaction | 6.3 | 3.1 | 4.7 | 6 |

| Components | Surfactant Composition 9 | Surfactant Composition 10 | Surfactant Composition 11 | Surfactant Composition 12 | Surfactant Composition 13 |
| --- | --- | --- | --- | --- | --- |
| First Aliphatic Alcohol | 900 | 900 | 900 | 3900 | 3900 |
| Second Aliphatic Alcohol | — | — | — | 2100 | 2100 |
| Third Aliphatic Alcohol | — | — | — | — | — |
| Fourth Aliphatic Alcohol | 2100 | 2100 | 2100 | — | — |
| Metal Catalyst | 17 | 17 | 17 | 18 | 18 |
| Ethylene Oxide | 2822 | 4233 | 5644 | 10973 | 12519 |
| Weight Percent of First Aliphatic Alcohol | 70 | 70 | 70 | 65 | 65 |
| Weight Percent of Second Aliphatic Alcohol | 30 | 30 | 30 | 35 | 35 |
| Moles of Ethylene Oxide Added to Reaction | 4 | 6 | 8 | 7.1 | 8.1 |

The First Aliphatic Alcohol includes 2-propylheptanol, commercially available from BASF Corporation of Florham Park, N.J. under the trade name of Lutensol® PH-2.

The Second Aliphatic Alcohol includes a mixture of 1-dodecanol, 1-tridecanol, and 1-tetradecanol, commercially available from Proctor and Gamble of Cincinnati, Ohio under the trade name of Fatty Alcohol CO-1214 CNO, commercially available from Henkel KGaA of Düsseldorf, Germany under the trade name of Lorol® 3333, commercially available from Cognis Corp. USA of Cincinnati, Ohio under the trade name of C12-14 A, and commercially available from United Coconut Chemicals, Inc. of the Philippines under the trade name of Philcohol 1216.

The Third Aliphatic Alcohol includes a mixture of 1-tridecanol, 1-tetradecanol, and 1-pentadecanol, commercially available from BASF Corporation of Wyandotte, Mich.

The Fourth Aliphatic Alcohol includes tridecyl alcohol commercially available from Exxon Mobil of Irving, Tex. under the trade name of Exaal® 13.

The Metal Catalyst is a 45% by weight aqueous solution of potassium hydroxide.

After formation, differing amounts of each of the Surfactant Compositions 1-13, in addition to samples of Comparative Surfactant Compositions 1-21, are independently added to a first cleaning solution (cleaning solution 1) to form Cleaning Formulations 1-32 and Comparative Cleaning Formulations 1-16, respectively. Each of the Cleaning Formulations 1-32 and the Comparative Cleaning Formulations 1-16 are evaluated for Percent Clean when applied to stained textile swatches. The Comparative Cleaning Formulations 1-16 are not formed according to the instant invention and do not include amounts of a polyalkylene glycol in excess of three percent by weight. It is to be appreciated that before addition into the first cleaning solution, each of the Surfactant Composition 1-13 are neutralized to a pH of approximately from 5 to 7.

The first cleaning solution, to which samples of each of the Compositions 1-13 and the Comparative Surfactant Compositions 1-16 are added, includes:
 0.5 g/l of the one of the Surfactant Compositions 1-13 or the Comparative Surfactant Compositions 1-16; and
 1.0 g/l of a builder system including:
  35% by weight of NaOH;
  6% by weight of sodium metasilicate.5$H_2O$;
  2% of methylglycinediacetic acid; and
  a balance of tap water (150 ppm of 2:1 Ca/Mg).

The Comparative Surfactant 1 includes a blend of 3 mole ethylene oxide adducts of alcohols having from 12 to 14 carbon atoms and is commercially available from BASF Corporation.

The Comparative Surfactant 2 includes a blend of 7 mole ethylene oxide adducts of alcohols having from 12 to 14 carbon atoms and is commercially available from BASF Corporation.

The Comparative Surfactant 3 includes a blend of 3 mole ethylene oxide adducts of alcohols having from 12 to 15 carbon atoms and is commercially available from Shell Chemicals of Houston, Tex.

The Comparative Surfactant 4 includes a blend of 7 mole ethylene oxide adducts of alcohols having from 12 to 15 carbon atoms and is commercially available from Shell Chemicals of Houston, Tex.

The Comparative Surfactant 5 includes a 4 mole ethoxylate of nonylphenol that is commercially available from BASF Corporation.

The Comparative Surfactant 6 includes a 6 mole ethoxylate of nonylphenol that is commercially available from BASF Corporation.

The Comparative Surfactant 7 includes a 9 mole ethoxylate of nonylphenol that is commercially available from BASF Corporation.

The Comparative Surfactant 8 includes an alkoxylate adduct of 2-propylheptanol that is commercially available from BASF Corporation under the trade name of Lutensol® XL-40 Surfactant.

The Comparative Surfactant 9 includes an ethoxylate adduct of 2-propylheptanol that is commercially available from BASF Corporation under the trade name of Lutensol® XP-30 Surfactant.

The Comparative Surfactant 10 includes an ethoxylate adduct of 2-propylheptanol that is commercially available from BASF Corporation under the trade name of Lutensol® XP-50 Surfactant.

The Comparative Surfactant 11 includes an ethoxylate adduct of 2-propylheptanol that is commercially available from BASF Corporation under the trade name of Lutensol® XP-70 Surfactant.

The Comparative Surfactant 12 includes a 3 mole ethylene oxide adduct of tridecyl alcohol that is commercially available from BASF Corporation.

The Comparative Surfactant 13 includes a 6 mole ethylene oxide adduct of tridecyl alcohol that is commercially available from BASF Corporation.

The Comparative Surfactant 14 includes a 8 mole ethylene oxide adduct of tridecyl alcohol that is commercially available from BASF Corporation.

The Comparative Surfactant 15 includes a 9 mole ethylene oxide adduct of tridecyl alcohol that is commercially available from BASF Corporation.

The Comparative Surfactant 16 includes an alcohol alkoxylate and is commercially available from BASF Corporation under the trade name of Plurafac® B25-5 Surfactant.

Cleaning Formulation 1 includes 0.5 g/l of Surfactant 9.
Cleaning Formulation 2 includes 0.5 g/l of Surfactant 10.
Cleaning Formulation 3 includes 0.5 g/l of Surfactant 11.
Cleaning Formulation 4 includes 0.5 g/l of a combination of 33% by weight of Surfactant 4 and 67% by weight of Surfactant 2.
Cleaning Formulation 5 includes 0.5 g/l of a combination of 33% by weight of Surfactant 6 and 67% by weight of Surfactant 2.
Cleaning Formulation 6 includes 0.5 g/l of a combination of 33.3% by weight of Surfactant 2, 33.3% by weight of Surfactant 4, and 33.3% by weight of Surfactant 6.
Cleaning Formulation 7 includes 0.5 g/l of a combination of 33.3% by weight of Surfactant 2 and 66.6% by weight of Surfactant 5.
Cleaning Formulation 8 includes 0.5 g/l of a combination of 33.3% by weight of Surfactant 3 and 66.6% by weight of Surfactant 4.
Cleaning Formulation 9 includes 0.5 g/l of a combination of 33.3% by weight of Surfactant 4 and 66.6% by weight of Surfactant 5.
Cleaning Formulation 10 includes 0.5 g/l of a combination of 33.3% by weight of Surfactant 5 and 66.6% by weight of Surfactant 6.
Cleaning Formulation 11 includes 0.5 g/l of a combination of 33.3% by weight of Surfactant 7 and 66.6% by weight of Surfactant 2.
Cleaning Formulation 12 includes 0.5 g/l of a combination of 33.3% by weight of Surfactant 7 and 66.6% by weight of Surfactant 4.

Cleaning Formulation 13 includes 0.5 g/l of Comparative Surfactant 12.

Cleaning Formulation 14 includes 0.5 g/l of Comparative Surfactant 13.

Cleaning Formulation 15 includes 0.5 g/l of a combination of 66.6% by weight of Surfactant 2 and 33.3% by weight of Surfactant 5.

Cleaning Formulation 16 includes 0.5 g/l of a combination of 66.6% by weight of Surfactant 3 and 33.3% by weight of Surfactant 2.

Cleaning Formulation 17 includes 0.5 g/l of a combination of 66.6% by weight of Surfactant 4 and 33.3% by weight of Surfactant 5.

Cleaning Formulation 18 includes 0.5 g/l of a combination of 66.6% by weight of Surfactant 5 and 33.3% by weight of Surfactant 6.

Cleaning Formulation 19 includes 0.5 g/l of a combination of 66.6% by weight of Surfactant 7 and 33.3% by weight of Surfactant 2.

Cleaning Formulation 20 includes 0.5 g/l of a combination of 66.6% by weight of Surfactant 7 and 33.3% by weight of Surfactant 4.

Cleaning Formulation 21 includes 0.5 g/l of a combination of 67% by weight of Surfactant 4 and 33% by weight of Surfactant 2.

Cleaning Formulation 22 includes 0.5 g/l of a combination of 67% by weight of Surfactant 4 and 33% by weight of Surfactant 6.

Cleaning Formulation 23 includes 0.5 g/l of a combination of 67% by weight of Surfactant 6 and 33% by weight of Surfactant 2.

Cleaning Formulation 24 includes 0.5 g/l of a combination of 67% by weight of Surfactant 6 and 33% by weight of Surfactant 4.

Cleaning Formulation 25 includes 0.5 g/l of Surfactant 1.
Cleaning Formulation 26 includes 0.5 g/l of Surfactant 2.
Cleaning Formulation 27 includes 0.5 g/l of Surfactant 3.
Cleaning Formulation 28 includes 0.5 g/l of Surfactant 4.
Cleaning Formulation 29 includes 0.5 g/l of Surfactant 5.
Cleaning Formulation 30 includes 0.5 g/l of Surfactant 6.
Cleaning Formulation 31 includes 0.5 g/l of Surfactant 7.
Cleaning Formulation 32 includes 0.5 g/l of Surfactant 8.

Comparative Cleaning Formulation 1 includes 0.5 g/l of Comparative Surfactant 1.

Comparative Cleaning Formulation 2 includes 0.5 g/l of Comparative Surfactant 2.

Comparative Cleaning Formulation 3 includes 0.5 g/l of Comparative Surfactant 3.

Comparative Cleaning Formulation 4 includes 0.5 g/l of Comparative Surfactant 4.

Comparative Cleaning Formulation 5 includes 0.5 g/l of Comparative Surfactant 16.

Comparative Cleaning Formulation 6 includes 0.5 g/l of Comparative Surfactant 5.

Comparative Cleaning Formulation 7 includes 0.5 g/l of Comparative Surfactant 6.

Comparative Cleaning Formulation 8 includes 0.5 g/l of Comparative Surfactant 7.

Comparative Cleaning Formulation 9 includes 0.5 g/l of Comparative Surfactant 12.

Comparative Cleaning Formulation 10 includes 0.5 g/l of Comparative Surfactant 13.

Comparative Cleaning Formulation 11 includes 0.5 g/l of Comparative Surfactant 14.

Comparative Cleaning Formulation 12 includes 0.5 g/l of Comparative Surfactant 15.

Comparative Cleaning Formulation 13 includes 0.5 g/l of Comparative Surfactant 8.

Comparative Cleaning Formulation 14 includes 0.5 g/l of Comparative Surfactant 9.

Comparative Cleaning Formulation 15 includes 0.5 g/l of Comparative Surfactant 10.

Comparative Cleaning Formulation 16 includes 0.5 g/l of Comparative Surfactant 11.

After the Cleaning Formulations 1-32 and the Comparative Cleaning Formulations 1-16 are formed, samples of each are used to clean stained textiles, as first introduced above. The efficacy of each of the Cleaning Formulations and Comparative Cleaning Formulations is evaluated based on a calculation of average "Percent Clean." The Percent Clean is calculated using reflectance measurements of the textiles. Reflectance measurements of the textiles are taken in three conditions, "Before Soiling", "After Soiling", and "After Cleaning". These measurements are determined using a reflectometer commercially available from X-Rite Asia Pacific Ltd. under the trade name of Colormaster. The reflectometer records three values based on the Hunter Color Scale. In the Hunter Color Scale, "L" values represent light (100) to dark (0), "a" values represent red (+a) to green (−a), and "b" values represent yellow (+b) to blue (−b). These three measurements are used to calculate ΔE via the following formula:

$$\Delta E = ((L_{AS} - L_{AC})^2 + (a_{AS} - a_{AC})^2 + (b_{AS} - b_{AC})^2)^{1/2}$$

wherein AS represents the "After Soiling" condition and AC represents the "After Cleaning" condition. Subsequently, ΔE is used to calculate Percent Clean via the following formula:

$$\text{Percent Clean} = [(\Delta E(AS - AC)) \div (\Delta E(BS - AS))] \times 100$$

wherein AS and AC are defined as above and BS represents the "Before Soiling" condition.

Initially, the reflectance of the textiles "Before Soiling" is determined. Subsequently, the textiles are soiled with a stain, i.e., Used Motor Oil, Sebum, a mixture of olive oil and carbon black or a mixture of paraffin and carbon black. The swatches stained with Used Motor Oil and Sebum are commercially available from Scientific Services, Inc. of the United Kingdom. The swatches stained with the olive oil and carbon black are commercially available from Scientific Services, Inc. of the United Kingdom, under the trade name of EMPA 104. The swatches stained with the paraffin wax and carbon black and are commercially available from Scientific Services, Inc. of the United Kingdom, under the trade name of EMPA 106.

The swatches are then washed in a tergotometer for 10 minutes under different heating conditions (120° F./150° F.) according to ASTM D3050-05. Subsequently, the textiles are then rinsed for one minute in tap water (150 ppm of 2:1 Ca/Mg). The tergotometer is commercially available from United States Testing Company of Hoboken, N.J. After washing, the textiles are allowed to dry. After drying, the "After Cleaning" reflectance of each of the textiles is determined. Upon determination of the "Before Soiling", "After Soiling", and "After Cleaning" reflectance values for the textiles, the average "Percent Clean" measurements are calculated, as described above and set forth in Tables below. Higher mean percent clean measurements indicate greater degrees of cleaning efficacy.

Table 2 includes mean percent clean data, and standard deviation, after washing a textile in the various Formulations at 120° F. This data represents the calculation of mean Percent Clean based on a number of sample measurements. The textile is a fabric including a blend of 35% cotton and 65% polyester that is stained with Dirty Motor Oil. The stained textile is commercially available from Scientific Services, Inc. of the United Kingdom.

TABLE 2

|  | Cleaning Formulation 1 | Cleaning Formulation 2 | Cleaning Formulation 3 | Cleaning Formulation 4 | Cleaning Formulation 5 |
|---|---|---|---|---|---|
| Mean Percent Clean | −26.860 | 2.610 | 0.840 | 3.420 | 2.105 |
| Number of Samples | 2 | 2 | 2 | 2 | 2 |
| Standard Deviation | 0.481 | 1.018 | 1.598 | 0.750 | 2.298 |

|  | Cleaning Formulation 6 | Cleaning Formulation 7 | Cleaning Formulation 8 | Cleaning Formulation 9 | Cleaning Formulation 10 |
|---|---|---|---|---|---|
| Mean Percent Clean | 0.770 | −0.650 | 1.575 | −0.755 | −34.960 |
| Number of Samples | 2 | 2 | 2 | 2 | 2 |
| Standard Deviation | 1.259 | 2.107 | 0.926 | 0.276 | 5.954 |

|  | Cleaning Formulation 11 | Cleaning Formulation 12 | Cleaning Formulation 13 | Cleaning Formulation 14 | Cleaning Formulation 15 |
|---|---|---|---|---|---|
| Mean Percent Clean | 0.575 | 0.700 | 0.580 | −0.160 | −2.310 |
| Number of Samples | 2 | 2 | 2 | 2 | 2 |
| Standard Deviation | 1.704 | 0.141 | 1.103 | 1.018 | 0.127 |

|  | Cleaning Formulation 16 | Cleaning Formulation 17 | Cleaning Formulation 18 | Cleaning Formulation 19 | Cleaning Formulation 20 |
|---|---|---|---|---|---|
| Mean Percent Clean | 0.680 | 1.565 | −14.065 | 0.175 | −0.660 |
| Number of Samples | 2 | 2 | 2 | 2 | 2 |
| Standard Deviation | 1.245 | 0.290 | 5.494 | 1.082 | 0.028 |

|  | Cleaning Formulation 21 | Cleaning Formulation 22 | Cleaning Formulation 23 | Cleaning Formulation 24 | Cleaning Formulation 25 |
|---|---|---|---|---|---|
| Mean Percent Clean | 1.235 | 2.470 | 2.185 | −14.530 | −1.920 |
| Number of Samples | 2 | 2 | 2 | 2 | 2 |
| Standard Deviation | 1.181 | 2.305 | 0.969 | 0.339 | 0.297 |

|  | Cleaning Formulation 26 | Cleaning Formulation 27 | Cleaning Formulation 28 | Cleaning Formulation 29 | Cleaning Formulation 30 |
|---|---|---|---|---|---|
| Mean Percent Clean | 0.445 | −0.700 | 4.955 | 0.260 | −36.915 |
| Number of Samples | 2 | 2 | 2 | 2 | 2 |
| Standard Deviation | 2.694 | 1.047 | 3.627 | 1.541 | 1.336 |

|  | Cleaning Formulation 31 | Cleaning Formulation 32 | Comp. Cleaning Formulation 1 | Comp. Cleaning Formulation 2 | Comp. Cleaning Formulation 3 |
|---|---|---|---|---|---|
| Mean Percent Clean | −1.080 | 1.460 | −32.985 | 0.130 | −34.585 |
| Number of Samples | 2 | 2 | 2 | 2 | 2 |
| Standard Deviation | 1.739 | 0.594 | 2.991 | 0.693 | 5.565 |

TABLE 2-continued

|  | Comp. Cleaning Formulation 4 | Comp. Cleaning Formulation 5 | Comp. Cleaning Formulation 6 | Comp. Cleaning Formulation 7 | Comp. Cleaning Formulation 8 |
|---|---|---|---|---|---|
| Mean Percent Clean | 0.710 | −0.945 | −39.750 | 37.455 | 1.250 |
| Number of Samples | 2 | 2 | 2 | 2 | 2 |
| Standard Deviation | 0.297 | 0.064 | 0.764 | 2.058 | 0.509 |

|  | Comp. Cleaning Formulation 9 | Comp. Cleaning Formulation 10 | Comp. Cleaning Formulation 11 | Comp. Cleaning Formulation 12 | Comp. Cleaning Formulation 13 |
|---|---|---|---|---|---|
| Mean Percent Clean | −26.120 | 2.035 | 1.990 | 2.045 | −21.425 |
| Number of Samples | 2 | 2 | 2 | 2 | 2 |
| Standard Deviation | 0.693 | 2.015 | 1.400 | 0.601 | 8.379 |

|  | Comp. Cleaning Formulation 14 | Comp. Cleaning Formulation 15 | Comp. Cleaning Formulation 16 |
|---|---|---|---|
| Mean Percent Clean | −15.665 | −23.440 | −17.285 |
| Number of Samples | 2 | 2 | 2 |
| Standard Deviation | 0.431 | 1.669 | 3.175 |

Figure 5:
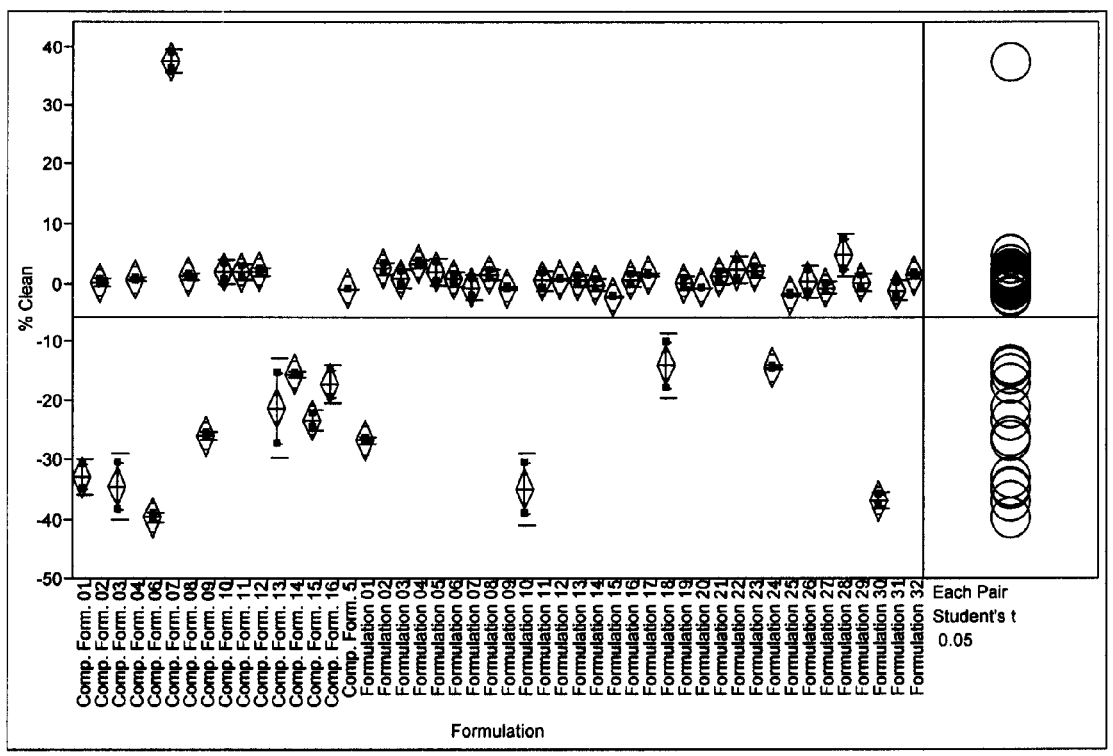
FIG. 5 is a diamond error graph of a one-way ANOVA of mean Percent Clean as a function of Cleaning Formulation. The Cleaning Formulations are diluted in a first cleaning solution and applied to polyester (65%)/cotton (35%) blend swatches stained with Dirty Motor Oil which are washed at 120° F.

As set forth in Table 2, and depicted in FIG. 5, the Formulations of the instant invention perform equally as well or better than many of the Comparative Formulations, as evidenced by the overlapping circles indicating that any differences between the Formulations and the Comparative Formulations are statistically insignificant at a confidence interval of 95%.

Table 3 includes mean percent clean data, and standard deviation, after washing a textile in the various Formulations at 150° F. This data represents the calculation of mean Percent Clean based on a number of sample measurements. The textile is a fabric including a blend of 35% cotton and 65% polyester that is stained with Dirty Motor Oil. The stained textile is commercially available from Scientific Services, Inc. of the United Kingdom.

TABLE 3

|  | Cleaning Formulation 1 | Cleaning Formulation 2 | Cleaning Formulation 3 | Cleaning Formulation 4 | Cleaning Formulation 5 |
|---|---|---|---|---|---|
| Mean Percent Clean | −55.280 | 7.720 | 4.370 | 5.015 | 4.345 |
| Number of Samples | 2 | 2 | 2 | 2 | 2 |
| Standard Deviation | 2.009 | 0.905 | 0.113 | 0.318 | 0.672 |

|  | Cleaning Formulation 6 | Cleaning Formulation 7 | Cleaning Formulation 8 | Cleaning Formulation 9 | Cleaning Formulation 10 |
|---|---|---|---|---|---|
| Mean Percent Clean | 10.315 | −0.695 | 3.730 | 9.365 | −48.450 |
| Number of Samples | 2 | 2 | 2 | 2 | 2 |
| Standard Deviation | 1.831 | 1.365 | 0.933 | 2.242 | 3.154 |

|  | Cleaning Formulation 11 | Cleaning Formulation 12 | Cleaning Formulation 13 | Cleaning Formulation 14 | Cleaning Formulation 15 |
|---|---|---|---|---|---|
| Mean Percent Clean | 3.120 | 19.730 | 4.020 | 2.385 | 0.345 |

TABLE 3-continued

|  | | | | | |
|---|---|---|---|---|---|
| Number of Samples | 2 | 2 | 2 | 2 | 2 |
| Standard Deviation | 1.655 | 0.721 | 1.032 | 1.704 | 0.544 |
|  | Cleaning Formulation 16 | Cleaning Formulation 17 | Cleaning Formulation 18 | Cleaning Formulation 19 | Cleaning Formulation 20 |
| Mean Percent Clean | 4.455 | 11.090 | −5.885 | 5.605 | 13.530 |
| Number of Samples | 2 | 2 | 2 | 2 | 2 |
| Standard Deviation | 0.714 | 2.333 | 1.365 | 2.270 | 0.566 |
|  | Cleaning Formulation 21 | Cleaning Formulation 22 | Cleaning Formulation 23 | Cleaning Formulation 24 | Cleaning Formulation 25 |
| Mean Percent Clean | 6.505 | 12.770 | −1.035 | −17.305 | 0.585 |
| Number of Samples | 2 | 2 | 2 | 2 | 2 |
| Standard Deviation | 0.007 | 7.594 | 1.082 | 2.722 | 0.601 |
|  | Cleaning Formulation 26 | Cleaning Formulation 27 | Cleaning Formulation 28 | Cleaning Formulation 29 | Cleaning Formulation 30 |
| Mean Percent Clean | −1.210 | 3.765 | 26.190 | 3.040 | −38.045 |
| Number of Samples | 2 | 2 | 2 | 2 | 4 |
| Standard Deviation | 0.636 | 2.949 | 0.269 | 2.772 | 4.104 |
|  | Cleaning Formulation 31 | Cleaning Formulation 32 | Comp. Cleaning Formulation 1 | Comp. Cleaning Formulation 2 | Comp. Cleaning Formulation 3 |
| Mean Percent Clean | 1.025 | 4.560 | −37.483 | 1.615 | −38.330 |
| Number of Samples | 4 | 2 | 4 | 2 | 2 |
| Standard Deviation | 1.659 | 1.146 | 2.460 | 2.397 | 5.332 |
|  | Comp. Cleaning Formulation 4 | Comp. Cleaning Formulation 5 | Comp. Cleaning Formulation 6 | Comp. Cleaning Formulation 7 | Comp. Cleaning Formulation 8 |
| Mean Percent Clean | 3.195 | 4.710 | −47.145 | 31.300 | 4.825 |
| Number of Samples | 2 | 2 | 2 | 2 | 2 |
| Standard Deviation | 0.700 | 0.410 | 1.223 | 4.893 | 1.068 |
|  | Comp. Cleaning Formulation 9 | Comp. Cleaning Formulation 10 | Comp. Cleaning Formulation 11 | Comp. Cleaning Formulation 12 | Comp. Cleaning Formulation 13 |
| Mean Percent Clean | −55.630 | 9.225 | 5.435 | 6.700 | −39.270 |
| Number of Samples | 2 | 2 | 2 | 2 | 2 |
| Standard Deviation | 6.251 | 0.587 | 0.898 | 1.980 | 8.202 |
|  |  | Comp. Cleaning Formulation 14 | Comp. Cleaning Formulation 15 | Comp. Cleaning Formulation 16 |  |
| Mean Percent Clean |  | −32.623 | −33.563 | −28.320 |  |

TABLE 3-continued

| | | | |
|---|---|---|---|
| Number of Samples | 4 | 4 | 4 |
| Standard Deviation | 2.613 | 7.463 | 3.826 |

Figure 6:
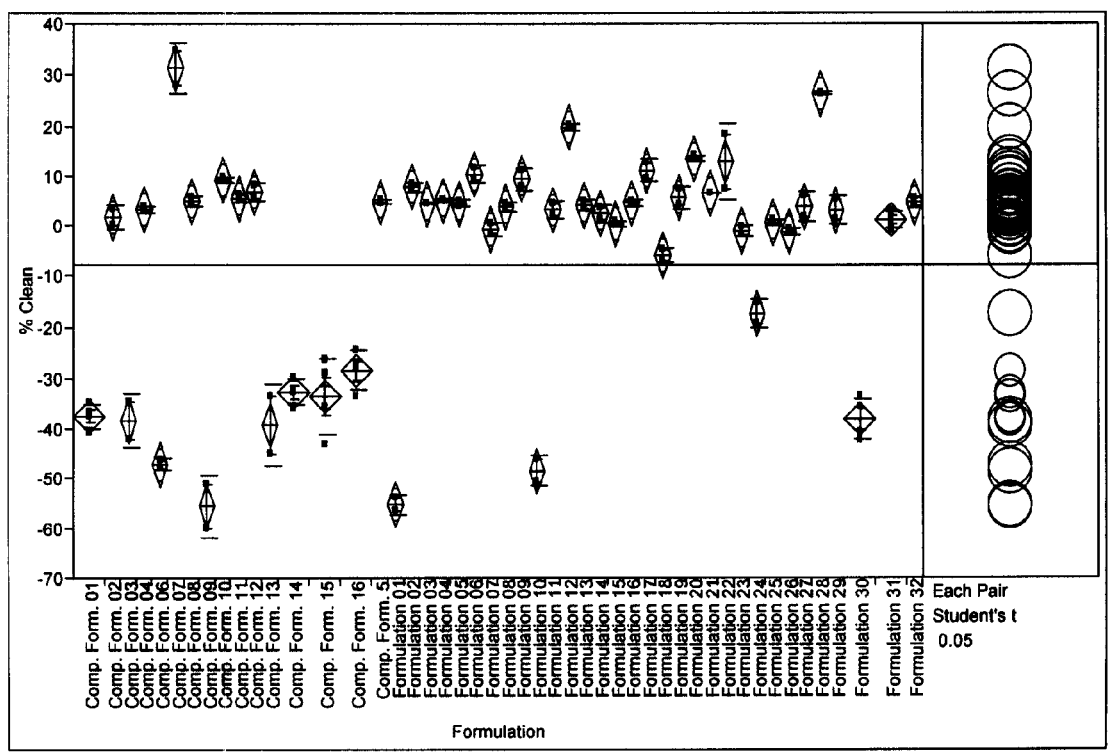
FIG. 6 is a diamond error graph of a one-way ANOVA of mean Percent Clean as a function of Cleaning Formulation. The Cleaning Formulations are diluted in a first cleaning solution and applied to polyester (65%)/cotton (35%) blend swatches stained with Dirty Motor Oil which are washed at 150° F.

As set forth in Table 3, and depicted in FIG. 6, the Formulations of the instant invention perform equally as well or better than many of the Comparative Formulations, as evidenced by the overlapping circles indicating that any differences between the Formulations and the Comparative Formulations are statistically insignificant at a confidence interval of 95%.

Table 4 includes mean percent clean data, and standard deviation, after washing a textile in the various Formulations at 120° F. This data represents the calculation of Mean Percent Clean based on a number of sample measurements. The textile is a fabric including 100% cotton that is stained with Dirty Motor Oil. The stained textile is commercially available from Scientific Services, Inc. of the United Kingdom.

TABLE 4

| | Cleaning Formulation 1 | Cleaning Formulation 2 | Cleaning Formulation 3 | Cleaning Formulation 4 | Cleaning Formulation 5 |
|---|---|---|---|---|---|
| Mean Percent Clean | −17.510 | 27.600 | 22.855 | 27.240 | 26.810 |
| Number of Samples | 2 | 2 | 2 | 2 | 2 |
| Standard Deviation | 15.769 | 0.608 | 1.011 | 2.942 | 1.626 |
| | Cleaning Formulation 6 | Cleaning Formulation 7 | Cleaning Formulation 8 | Cleaning Formulation 9 | Cleaning Formulation 10 |
| Mean Percent Clean | 26.650 | 23.500 | 22.330 | 29.600 | −19.355 |
| Number of Samples | 2 | 2 | 2 | 2 | 2 |
| Standard Deviation | 3.705 | 1.711 | 0.608 | 2.150 | 4.292 |
| | Cleaning Formulation 11 | Cleaning Formulation 12 | Cleaning Formulation 13 | Cleaning Formulation 14 | Cleaning Formulation 15 |
| Mean Percent Clean | 16.305 | 26.020 | 22.145 | 21.085 | 19.505 |
| Number of Samples | 2 | 2 | 2 | 2 | 2 |
| Standard Deviation | 6.951 | 0.113 | 3.825 | 2.595 | 1.534 |
| | Cleaning Formulation 16 | Cleaning Formulation 17 | Cleaning Formulation 18 | Cleaning Formulation 19 | Cleaning Formulation 20 |
| Mean Percent Clean | 19.860 | 22.620 | −9.420 | 26.130 | 22.980 |
| Number of Samples | 2 | 2 | 2 | 2 | 2 |
| Standard Deviation | 1.457 | 4.455 | 3.338 | 0.792 | 14.750 |
| | Cleaning Formulation 21 | Cleaning Formulation 22 | Cleaning Formulation 23 | Cleaning Formulation 24 | Cleaning Formulation 25 |
| Mean Percent Clean | 27.550 | 26.415 | 14.085 | −6.695 | 16.725 |
| Number of Samples | 2 | 2 | 2 | 2 | 2 |
| Standard Deviation | 0.127 | 8.606 | 6.187 | 7.715 | 3.500 |
| | Cleaning Formulation 26 | Cleaning Formulation 27 | Cleaning Formulation 28 | Cleaning Formulation 29 | Cleaning Formulation 30 |
| Mean Percent Clean | 23.270 | 18.585 | 29.785 | 20.985 | −23.675 |

TABLE 4-continued

|  | | | | | |
|---|---|---|---|---|---|
| Number of Samples | 2 | 2 | 2 | 2 | 2 |
| Standard Deviation | 0.693 | 2.114 | 11.236 | 10.034 | 4.207 |

|  | Cleaning Formulation 31 | Cleaning Formulation 32 | Comp. Cleaning Formulation 1 | Comp. Cleaning Formulation 2 | Comp. Cleaning Formulation 3 |
|---|---|---|---|---|---|
| Mean Percent Clean | 6.425 | 28.660 | −33.020 | 19.180 | −40.245 |
| Number of Samples | 2 | 2 | 2 | 2 | 2 |
| Standard Deviation | 11.986 | 0.905 | 11.469 | 11.172 | 5.607 |

|  | Comp. Cleaning Formulation 4 | Comp. Cleaning Formulation 5 | Comp. Cleaning Formulation 6 | Comp. Cleaning Formulation 7 | Comp. Cleaning Formulation 8 |
|---|---|---|---|---|---|
| Mean Percent Clean | 17.095 | 17.070 | −42.730 | 23.625 | 18.940 |
| Number of Samples | 2 | 2 | 2 | 2 | 2 |
| Standard Deviation | 1.732 | 0.410 | 6.025 | 3.472 | 2.319 |

|  | Comp. Cleaning Formulation 9 | Comp. Cleaning Formulation 10 | Comp. Cleaning Formulation 11 | Comp. Cleaning Formulation 12 | Comp. Cleaning Formulation 13 |
|---|---|---|---|---|---|
| Mean Percent Clean | −13.130 | 29.175 | 25.785 | 24.485 | −1.425 |
| Number of Samples | 2 | 2 | 2 | 2 | 2 |
| Standard Deviation | 13.364 | 7.884 | 2.807 | 3.755 | 3.288 |

|  | Comp. Cleaning Formulation 14 | Comp. Cleaning Formulation 15 | Comp. Cleaning Formulation 16 |
|---|---|---|---|
| Mean Percent Clean | 3.510 | 9.695 | 3.315 |
| Number of Samples | 2 | 2 | 2 |
| Standard Deviation | 5.120 | 2.666 | 9.652 |

Figure 7:
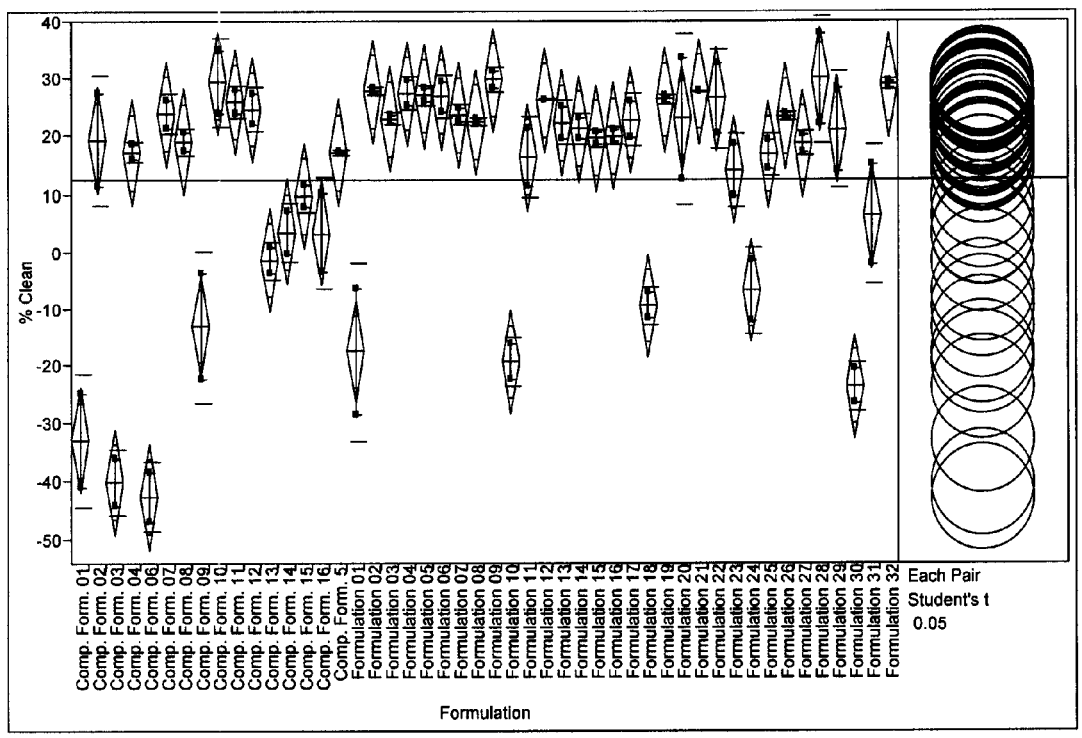
FIG. 7 is a diamond error graph of a one-way ANOVA of mean Percent Clean as a function of Cleaning Formulation. The Cleaning Formulations are diluted in a first cleaning solution and applied to 100% cotton swatches stained with Dirty Motor Oil which are washed at 120° F.

As set forth in Table 4, and depicted in FIG. 7, the Formulations of the instant invention perform equally as well or better than many of the Comparative Formulations, as evidenced by the overlapping circles indicating that any differences between the Formulations and the Comparative Formulations are statistically insignificant at a confidence interval of 95%.

Table 5 includes mean percent clean data, and standard deviation, after washing a textile in the various Formulations at 150° F. This data represents the calculation of mean Percent Clean based on a number of sample measurements. The textile is a fabric including 100% cotton that is stained with Dirty Motor Oil. The stained textile is commercially available from Scientific Services, Inc. of the United Kingdom.

TABLE 5

|  | Cleaning Formulation 1 | Cleaning Formulation 2 | Cleaning Formulation 3 | Cleaning Formulation 4 | Cleaning Formulation 5 |
|---|---|---|---|---|---|
| Mean Percent Clean | −12.040 | 40.605 | 35.810 | 38.485 | 38.095 |
| Number of Samples | 2 | 2 | 2 | 2 | 2 |
| Standard Deviation | 3.083 | 1.294 | 1.810 | 3.514 | 2.567 |

TABLE 5-continued

|  | Cleaning Formulation 6 | Cleaning Formulation 7 | Cleaning Formulation 8 | Cleaning Formulation 9 | Cleaning Formulation 10 |
| --- | --- | --- | --- | --- | --- |
| Mean Percent Clean | 35.310 | 28.945 | 36.775 | 35.040 | −6.195 |
| Number of Samples | 2 | 2 | 2 | 2 | 2 |
| Standard Deviation | 3.917 | 2.326 | 4.349 | 3.875 | 5.240 |
|  | Cleaning Formulation 11 | Cleaning Formulation 12 | Cleaning Formulation 13 | Cleaning Formulation 14 | Cleaning Formulation 15 |
| Mean Percent Clean | 33.710 | 32.105 | 32.825 | 33.280 | 36.160 |
| Number of Samples | 2 | 2 | 2 | 2 | 2 |
| Standard Deviation | 2.786 | 0.728 | 5.424 | 2.574 | 0.792 |
|  | Cleaning Formulation 16 | Cleaning Formulation 17 | Cleaning Formulation 18 | Cleaning Formulation 19 | Cleaning Formulation 20 |
| Mean Percent Clean | 34.715 | 36.600 | −2.520 | 26.735 | 21.305 |
| Number of Samples | 2 | 2 | 2 | 2 | 2 |
| Standard Deviation | 4.688 | 2.574 | 12.134 | 1.987 | 1.266 |
|  | Cleaning Formulation 21 | Cleaning Formulation 22 | Cleaning Formulation 23 | Cleaning Formulation 24 | Cleaning Formulation 25 |
| Mean Percent Clean | 40.525 | 36.145 | −6.525 | −22.340 | 29.680 |
| Number of Samples | 2 | 2 | 2 | 2 | 2 |
| Standard Deviation | 2.058 | 13.513 | 3.769 | 13.746 | 5.247 |
|  | Cleaning Formulation 26 | Cleaning Formulation 27 | Cleaning Formulation 28 | Cleaning Formulation 29 | Cleaning Formulation 30 |
| Mean Percent Clean | 27.000 | 34.365 | 35.155 | 37.560 | −35.960 |
| Number of Samples | 2 | 2 | 2 | 2 | 4 |
| Standard Deviation | 2.319 | 2.185 | 2.680 | 0.184 | 14.745 |
|  | Cleaning Formulation 31 | Cleaning Formulation 32 | Comp. Cleaning Formulation 1 | Comp. Cleaning Formulation 2 | Comp. Cleaning Formulation 3 |
| Mean Percent Clean | 15.818 | 38.130 | −30.295 | 36.695 | −38.710 |
| Number of Samples | 4 | 2 | 4 | 2 | 2 |
| Standard Deviation | 8.874 | 0.820 | 4.119 | 1.435 | 2.447 |
|  | Comp. Cleaning Formulation 4 | Comp. Cleaning Formulation 5 | Comp. Cleaning Formulation 6 | Comp. Cleaning Formulation 7 | Comp. Cleaning Formulation 8 |
| Mean Percent Clean | 31.050 | 25.210 | −38.420 | 34.130 | 32.585 |
| Number of Samples | 2 | 2 | 2 | 2 | 2 |
| Standard Deviation | 1.725 | 5.756 | 2.461 | 9.249 | 0.827 |

TABLE 5-continued

|  | Comp. Cleaning Formulation 9 | Comp. Cleaning Formulation 10 | Comp. Cleaning Formulation 11 | Comp. Cleaning Formulation 12 | Comp. Cleaning Formulation 13 |
|---|---|---|---|---|---|
| Mean Percent Clean | −1.570 | 39.380 | 35.515 | 38.570 | −20.710 |
| Number of Samples | 2 | 2 | 2 | 2 | 2 |
| Standard Deviation | 1.697 | 3.960 | 5.904 | 0.269 | 15.415 |

|  | Comp. Cleaning Formulation 14 | Comp. Cleaning Formulation 15 | Comp. Cleaning Formulation 16 |
|---|---|---|---|
| Mean Percent Clean | 1.828 | 7.985 | 14.735 |
| Number of Samples | 4 | 4 | 4 |
| Standard Deviation | 4.082 | 2.574 | 6.664 |

Figure 8:
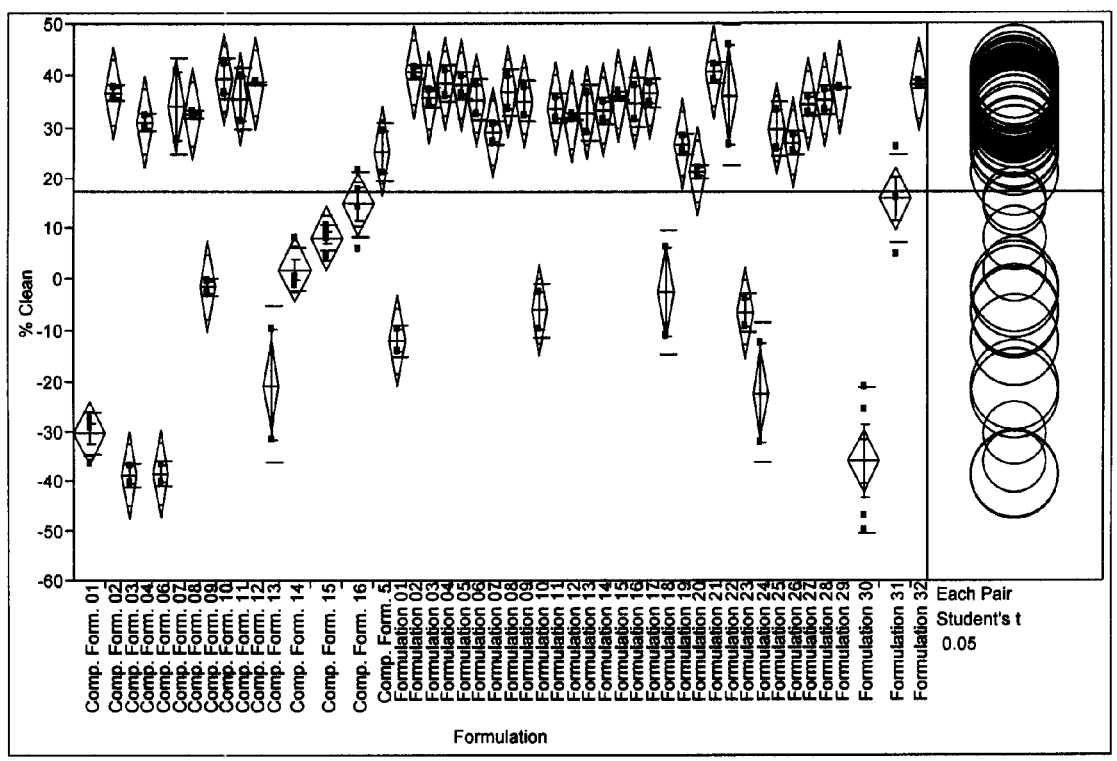
FIG. 8 is a diamond error graph of a one-way ANOVA of mean Percent Clean as a function of Cleaning Formulation. The Cleaning Formulations are diluted in a first cleaning solution and applied to 100% cotton swatches stained with Dirty Motor Oil which are washed at 150° F.

As set forth in Table 5, and depicted in FIG. 8, the Formulations of the instant invention perform equally as well or better than many of the Comparative Formulations, as evidenced by the overlapping circles indicating that any differences between the Formulations and the Comparative Formulations are statistically insignificant at a confidence interval of 95%.

Table 6 includes mean percent clean data, and standard deviation, after washing a textile in the various Formulations at 120° F. This data represents the calculation of mean Percent Clean based on a number of sample measurements. The textile is a fabric including a blend of 35% cotton and 65% polyester that is stained with Sebum. The stained textile is commercially available from Scientific Services, Inc. of the United Kingdom.

TABLE 6

|  | Cleaning Formulation 1 | Cleaning Formulation 2 | Cleaning Formulation 3 | Cleaning Formulation 4 | Cleaning Formulation 5 |
|---|---|---|---|---|---|
| Mean Percent Clean | 41.600 | 76.615 | 79.375 | 78.845 | 76.980 |
| Number of Samples | 2 | 2 | 2 | 2 | 2 |
| Standard Deviation | 8.287 | 0.700 | 0.332 | 0.799 | 1.909 |

|  | Cleaning Formulation 6 | Cleaning Formulation 7 | Cleaning Formulation 8 | Cleaning Formulation 9 | Cleaning Formulation 10 |
|---|---|---|---|---|---|
| Mean Percent Clean | 78.155 | 77.375 | 75.655 | 77.605 | 27.565 |
| Number of Samples | 2 | 2 | 2 | 2 | 2 |
| Standard DeviationP | 1.633 | 4.236 | 1.039 | 1.718 | 0.870 |

|  | Cleaning Formulation 11 | Cleaning Formulation 12 | Cleaning Formulation 13 | Cleaning Formulation 14 | Cleaning Formulation 15 |
|---|---|---|---|---|---|
| Mean Percent Clean | 73.760 | 76.130 | 78.025 | 75.555 | 74.830 |
| Number of Samples | 2 | 2 | 2 | 2 | 2 |
| Standard Deviation | 0.863 | 1.669 | 0.219 | 1.506 | 0.566 |

|  | Cleaning Formulation 16 | Cleaning Formulation 17 | Cleaning Formulation 18 | Cleaning Formulation 19 | Cleaning Formulation 20 |
|---|---|---|---|---|---|
| Mean Percent Clean | 73.880 | 75.815 | 49.060 | 77.645 | 74.385 |

TABLE 6-continued

|  | | | | | |
|---|---|---|---|---|---|
| Number of Samples | 2 | 2 | 2 | 2 | 2 |
| Standard Deviation | 1.131 | 2.143 | 4.214 | 0.983 | 0.276 |

|  | Cleaning Formulation 21 | Cleaning Formulation 22 | Cleaning Formulation 23 | Cleaning Formulation 24 | Cleaning Formulation 25 |
|---|---|---|---|---|---|
| Mean Percent Clean | 77.580 | 73.200 | 62.905 | 53.440 | 72.465 |
| Number of Samples | 2 | 2 | 2 | 2 | 2 |
| Standard Deviation | 3.281 | 1.966 | 2.086 | 7.114 | 0.502 |

|  | Cleaning Formulation 26 | Cleaning Formulation 27 | Cleaning Formulation 28 | Cleaning Formulation 29 | Cleaning Formulation 30 |
|---|---|---|---|---|---|
| Mean Percent Clean | 73.390 | 70.065 | 71.615 | 71.735 | 17.915 |
| Number of Samples | 2 | 2 | 2 | 2 | 2 |
| Standard Deviation | 0.834 | 2.666 | 0.219 | 1.393 | 1.761 |

|  | Cleaning Formulation 31 | Cleaning Formulation 32 | Comp. Cleaning Formulation 1 | Comp. Cleaning Formulation 2 | Comp. Cleaning Formulation 3 |
|---|---|---|---|---|---|
| Mean Percent Clean | 54.490 | 74.210 | 17.295 | 72.425 | 14.250 |
| Number of Samples | 2 | 2 | 2 | 2 | 2 |
| Standard Deviation | 11.879 | 1.641 | 9.496 | 1.435 | 6.053 |

|  | Comp. Cleaning Formulation 4 | Comp. Cleaning Formulation 5 | Comp. Cleaning Formulation 6 | Comp. Cleaning Formulation 7 | Comp. Cleaning Formulation 8 |
|---|---|---|---|---|---|
| Mean Percent Clean | 65.450 | 70.625 | −32.010 | 58.305 | 64.705 |
| Number of Samples | 2 | 2 | 2 | 2 | 2 |
| Standard Deviation | 0.226 | 2.482 | 4.511 | 0.431 | 0.332 |

|  | Comp. Cleaning Formulation 9 | Comp. Cleaning Formulation 10 | Comp. Cleaning Formulation 11 | Comp. Cleaning Formulation 12 | Comp. Cleaning Formulation 13 |
|---|---|---|---|---|---|
| Mean Percent Clean | 19.770 | 75.380 | 73.345 | 73.940 | 25.610 |
| Number of Samples | 2 | 2 | 2 | 2 | 2 |
| Standard Deviation | 0.552 | 1.471 | 2.737 | 1.810 | 12.304 |

|  | Comp. Cleaning Formulation 14 | Comp. Cleaning Formulation 15 | Comp. Cleaning Formulation 16 |
|---|---|---|---|
| Mean Percent Clean | 22.815 | 16.325 | 45.795 |
| Number of Samples | 2 | 2 | 2 |
| Standard Deviation | 0.728 | 3.995 | 8.747 |

Figure 9:
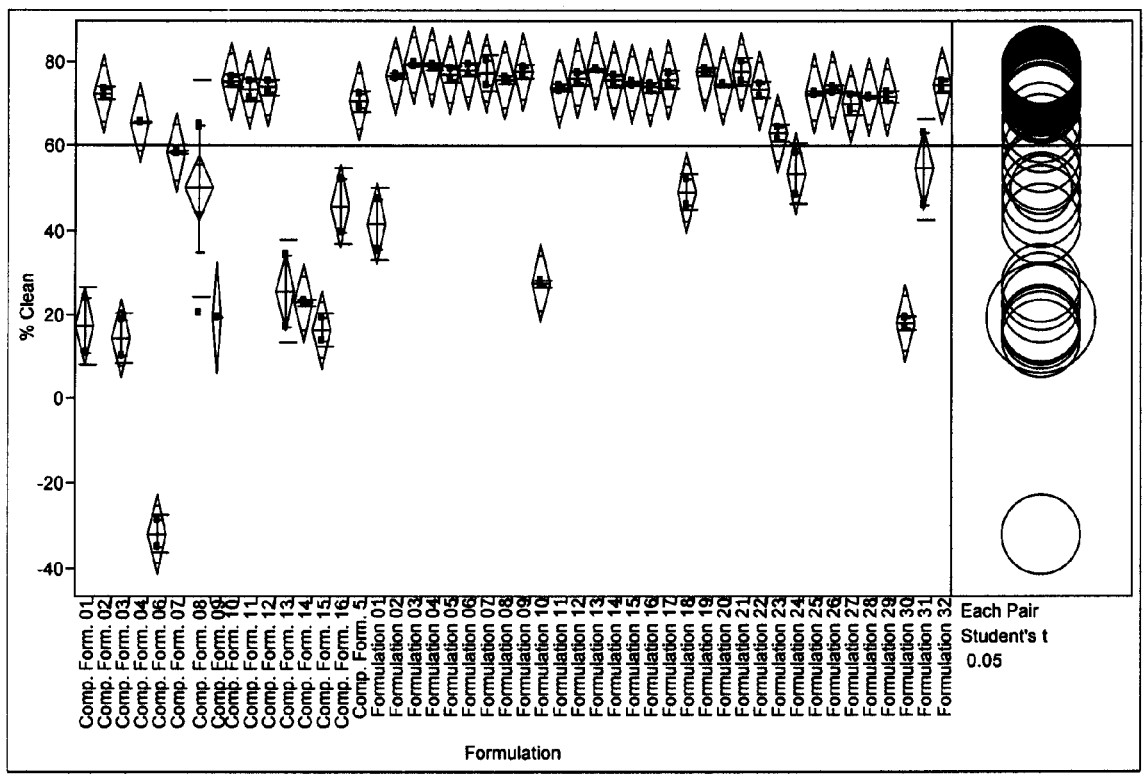
FIG. 9 is a diamond error graph of a one-way ANOVA of mean Percent Clean as a function of Cleaning Formulation. The Cleaning Formulations are diluted in a first cleaning solution and applied to polyester (65%)/cotton (35%) blend swatches stained with Sebum which are washed at 120° F.

As set forth in Table 6, and depicted in FIG. 9, the Formulations of the instant invention perform equally as well or better than many of the Comparative Formulations, as evidenced by the overlapping circles indicating that any differences between the Formulations and the Comparative Formulations are statistically insignificant at a confidence interval of 95%.

Table 7 includes mean percent clean data, and standard deviation, after washing a textile in the various Formulations at 150° F. This data represents the calculation of mean Percent Clean based on a number of sample measurements. The textile is a fabric including a blend of 35% cotton and 65% polyester that is stained with Sebum. The stained textile is commercially available from Scientific Services, Inc. of the United Kingdom.

TABLE 7

|  | Cleaning Formulation 1 | Cleaning Formulation 2 | Cleaning Formulation 3 | Cleaning Formulation 4 | Cleaning Formulation 5 |
| --- | --- | --- | --- | --- | --- |
| Mean Percent Clean | −3.180 | 75.425 | 81.530 | 81.065 | 79.375 |
| Number of Samples | 2 | 2 | 2 | 2 | 2 |
| Standard Deviation | 2.701 | 0.644 | 1.938 | 2.369 | 2.242 |

|  | Cleaning Formulation 6 | Cleaning Formulation 7 | Cleaning Formulation 8 | Cleaning Formulation 9 | Cleaning Formulation 10 |
| --- | --- | --- | --- | --- | --- |
| Mean Percent Clean | 77.010 | 82.250 | 81.210 | 75.305 | 7.505 |
| Number of Samples | 2 | 2 | 2 | 2 | 2 |
| Standard Deviation | 0.255 | 0.170 | 2.107 | 1.577 | 4.108 |

|  | Cleaning Formulation 11 | Cleaning Formulation 12 | Cleaning Formulation 13 | Cleaning Formulation 14 | Cleaning Formulation 15 |
| --- | --- | --- | --- | --- | --- |
| Mean Percent Clean | 80.975 | 60.970 | 83.170 | 81.235 | 80.475 |
| Number of Samples | 2 | 2 | 2 | 2 | 2 |
| Standard Deviation | 2.609 | 4.144 | 1.655 | 1.082 | 1.082 |

|  | Cleaning Formulation 16 | Cleaning Formulation 17 | Cleaning Formulation 18 | Cleaning Formulation 19 | Cleaning Formulation 20 |
| --- | --- | --- | --- | --- | --- |
| Mean Percent Clean | 81.015 | 73.425 | 32.775 | 79.580 | 60.715 |
| Number of Samples | 2 | 2 | 2 | 2 | 2 |
| Standard Deviation | 0.064 | 1.054 | 6.710 | 2.305 | 1.704 |

|  | Cleaning Formulation 21 | Cleaning Formulation 22 | Cleaning Formulation 23 | Cleaning Formulation 24 | Cleaning Formulation 25 |
| --- | --- | --- | --- | --- | --- |
| Mean Percent Clean | 79.415 | 62.845 | 34.740 | 38.425 | 83.610 |
| Number of Samples | 2 | 2 | 2 | 2 | 2 |
| Standard Deviation | 0.021 | 18.349 | 6.095 | 0.021 | 0.424 |

|  | Cleaning Formulation 26 | Cleaning Formulation 27 | Cleaning Formulation 28 | Cleaning Formulation 29 | Cleaning Formulation 30 |
| --- | --- | --- | --- | --- | --- |
| Mean Percent Clean | 73.695 | 80.560 | 57.470 | 75.200 | 7.493 |
| Number of Samples | 2 | 2 | 2 | 2 | 4 |
| Standard Deviation | 0.941 | 1.725 | 2.121 | 2.942 | 9.987 |

|  | Cleaning Formulation 31 | Cleaning Formulation 32 | Comp. Cleaning Formulation 1 | Comp. Cleaning Formulation 2 | Comp. Cleaning Formulation 3 |
| --- | --- | --- | --- | --- | --- |
| Mean Percent Clean | 34.295 | 79.320 | 5.105 | 74.920 | 9.020 |
| Number of Samples | 4 | 2 | 4 | 2 | 2 |

TABLE 7-continued

|  | | | | | |
|---|---|---|---|---|---|
| Standard Deviation | 19.723 | 1.315 | 7.367 | 0.311 | 16.207 |

|  | Comp. Cleaning Formulation 4 | Comp. Cleaning Formulation 5 | Comp. Cleaning Formulation 6 | Comp. Cleaning Formulation 7 | Comp. Cleaning Formulation 8 |
|---|---|---|---|---|---|
| Mean Percent Clean | 81.595 | 73.830 | −45.860 | 56.915 | 80.235 |
| Number of Samples | 2 | 2 | 2 | 2 | 2 |
| Standard Deviation | 0.488 | 0.127 | 1.117 | 7.106 | 0.743 |

|  | Comp. Cleaning Formulation 9 | Comp. Cleaning Formulation 10 | Comp. Cleaning Formulation 11 | Comp. Cleaning Formulation 12 | Comp. Cleaning Formulation 13 |
|---|---|---|---|---|---|
| Mean Percent Clean | −35.595 | 72.115 | 79.755 | 81.380 | −37.460 |
| Number of Samples | 2 | 2 | 2 | 2 | 2 |
| Standard Deviation | 27.231 | 0.163 | 0.021 | 0.764 | 7.891 |

|  | Comp. Cleaning Formulation 14 | Comp. Cleaning Formulation 15 | Comp. Cleaning Formulation 16 |
|---|---|---|---|
| Mean Percent Clean | −4.863 | 4.890 | 43.575 |
| Number of Samples | 4 | 4 | 4 |
| Standard Deviation | 14.923 | 12.999 | 9.800 |

Figure 10:
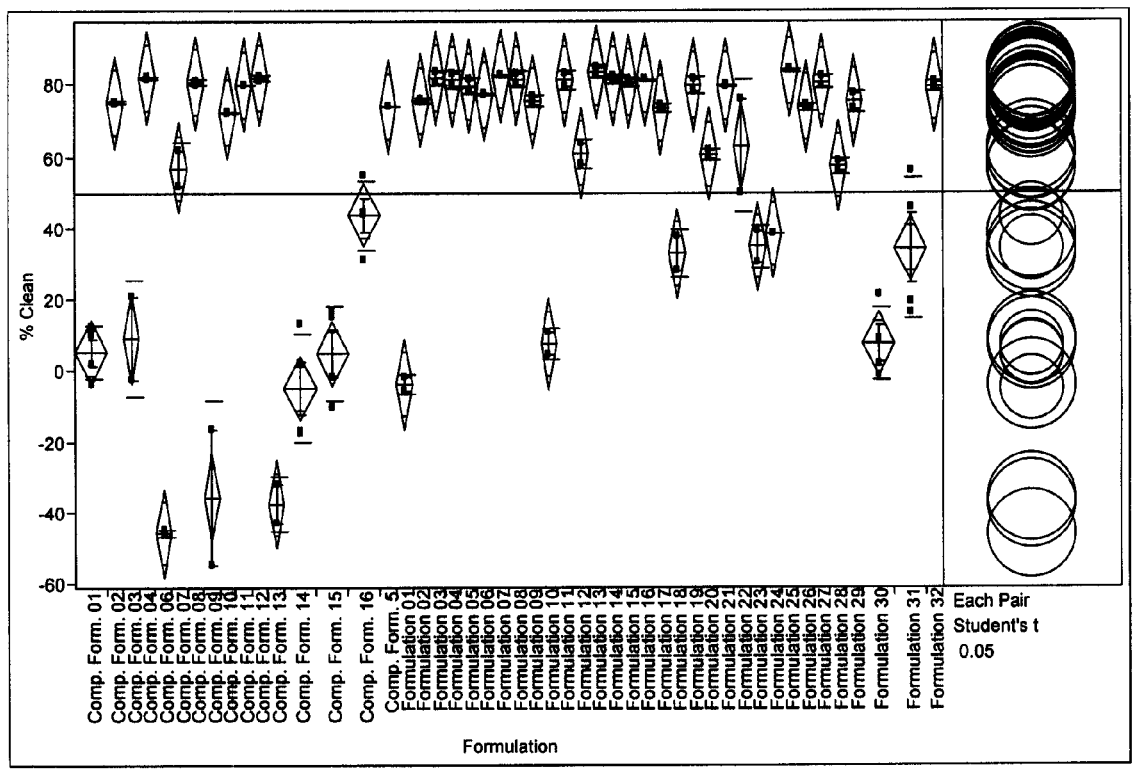
FIG. 10 is a diamond error graph of a one-way ANOVA of mean Percent Clean as a function of Cleaning Formulation. The Cleaning Formulations are diluted in a first cleaning solution and applied to polyester (65%)/cotton (35%) blend swatches stained with Sebum which are washed at 150° F.

As set forth in Table 7, and depicted in FIG. 10, the Formulations of the instant invention perform equally as well or better than many of the Comparative Formulations, as evidenced by the overlapping circles indicating that any differences between the Formulations and the Comparative Formulations are statistically insignificant at a confidence interval of 95%.

Table 8 includes mean percent clean data, and standard deviation, after washing a textile in the various Formulations at 120° F. This data represents the calculation of mean Percent Clean based on a number of sample measurements. The textile is a fabric including a blend of 35% cotton and 65% polyester that is stained with carbon black and olive oil (EMPA 104). The stained textile is commercially available from Scientific Services, Inc. of the United Kingdom.

TABLE 8

|  | Cleaning Formulation 1 | Cleaning Formulation 2 | Cleaning Formulation 3 | Cleaning Formulation 4 | Cleaning Formulation 5 |
|---|---|---|---|---|---|
| Mean Percent Clean | 7.555 | 27.220 | 28.275 | 29.350 | 27.250 |
| Number of Samples | 2 | 2 | 2 | 2 | 2 |
| Standard Deviation | 5.070 | 1.556 | 1.633 | 1.500 | 0.339 |

|  | Cleaning Formulation 6 | Cleaning Formulation 7 | Cleaning Formulation 8 | Cleaning Formulation 9 | Cleaning Formulation 10 |
|---|---|---|---|---|---|
| Mean Percent Clean | 24.405 | 24.540 | 30.045 | 28.010 | 9.140 |
| Number of Samples | 2 | 2 | 2 | 2 | 2 |
| Standard Deviation | 1.959 | 1.980 | 0.035 | 1.923 | 1.287 |

TABLE 8-continued

|  | Cleaning Formulation 11 | Cleaning Formulation 12 | Cleaning Formulation 13 | Cleaning Formulation 14 | Cleaning Formulation 15 |
|---|---|---|---|---|---|
| Mean Percent Clean | 29.420 | 26.190 | 28.245 | 26.905 | 24.940 |
| Number of Samples | 2 | 2 | 2 | 2 | 2 |
| Standard Deviation | 0.863 | 1.881 | 2.482 | 3.359 | 2.560 |
|  | Cleaning Formulation 16 | Cleaning Formulation 17 | Cleaning Formulation 18 | Cleaning Formulation 19 | Cleaning Formulation 20 |
| Mean Percent Clean | 26.985 | 28.220 | 13.880 | 26.035 | 22.875 |
| Number of Samples | 2 | 2 | 2 | 2 | 2 |
| Standard Deviation | 1.450 | 1.895 | 1.838 | 1.846 | 0.092 |
|  | Cleaning Formulation 21 | Cleaning Formulation 22 | Cleaning Formulation 23 | Cleaning Formulation 24 | Cleaning Formulation 25 |
| Mean Percent Clean | 28.595 | 23.565 | 18.225 | 11.560 | 25.930 |
| Number of Samples | 2 | 2 | 2 | 2 | 2 |
| Standard Deviation | 1.379 | 0.983 | 0.573 | 1.683 | 3.210 |
|  | Cleaning Formulation 26 | Cleaning Formulation 27 | Cleaning Formulation 28 | Cleaning Formulation 29 | Cleaning Formulation 30 |
| Mean Percent Clean | 27.510 | 28.355 | 24.810 | 27.065 | 6.525 |
| Number of Samples | 2 | 2 | 2 | 2 | 2 |
| Standard Deviation | 2.984 | 1.181 | 0.594 | 0.495 | 1.945 |
|  | Cleaning Formulation 31 | Cleaning Formulation 32 | Comp. Cleaning Formulation 1 | Comp. Cleaning Formulation 2 | Comp. Cleaning Formulation 3 |
| Mean Percent Clean | 18.360 | 29.470 | 9.165 | 25.995 | 7.610 |
| Number of Samples | 2 | 2 | 2 | 2 | 2 |
| Standard Deviation | 1.146 | 0.156 | 1.237 | 3.939 | 1.301 |
|  | Comp. Cleaning Formulation 4 | Comp. Cleaning Formulation 5 | Comp. Cleaning Formulation 6 | Comp. Cleaning Formulation 7 | Comp. Cleaning Formulation 8 |
| Mean Percent Clean | 29.545 | 28.105 | −1.610 | 25.660 | 30.760 |
| Number of Samples | 2 | 2 | 2 | 2 | 2 |
| Standard Deviation | 2.440 | 3.005 | 1.188 | 0.438 | 1.245 |
|  | Comp. Cleaning Formulation 9 | Comp. Cleaning Formulation 10 | Comp. Cleaning Formulation 11 | Comp. Cleaning Formulation 12 | Comp. Cleaning Formulation 13 |
| Mean Percent Clean | −0.115 | 28.285 | 32.580 | 29.365 | 9.985 |
| Number of Samples | 2 | 2 | 2 | 2 | 2 |
| Standard Deviation | 0.332 | 0.898 | 0.679 | 4.589 | 0.064 |

TABLE 8-continued

|  | Comp. Cleaning Formulation 14 | Comp. Cleaning Formulation 15 | Comp. Cleaning Formulation 16 |
|---|---|---|---|
| Mean Percent Clean | 9.935 | 10.450 | 16.305 |
| Number of Samples | 2 | 2 | 2 |
| Standard Deviation | 0.191 | 0.297 | 0.629 |

Figure 11:
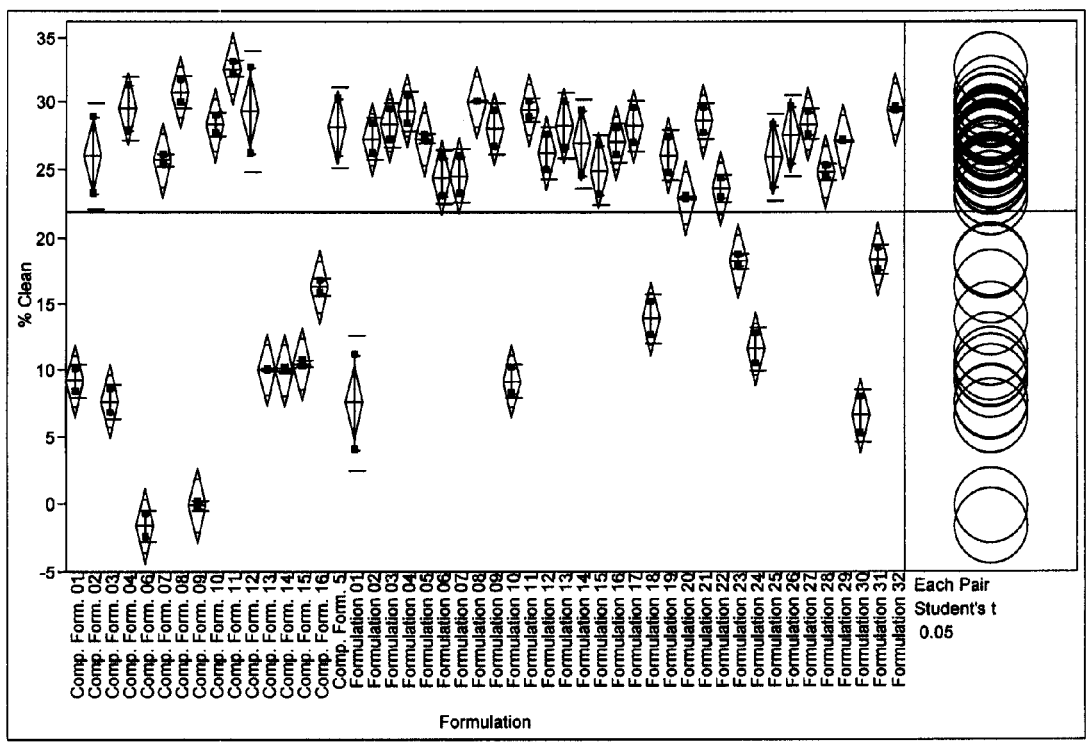
FIG. 11 is a diamond error graph of a one-way ANOVA of mean Percent Clean as a function of Cleaning Formulation.

As set forth in Table 8, and depicted in FIG. 11, the Formulations of the instant invention perform equally as well or better than many of the Comparative Formulations, as evidenced by the overlapping circles indicating that any differences between the Formulations and the Comparative Formulations are statistically insignificant at a confidence interval of 95%.

Table 9 includes mean percent clean data, and standard deviation, after washing a textile in the various Formulations at 150° F. This data represents the calculation of mean Percent Clean based on a number of sample measurements. The textile is a fabric including a blend of 35% cotton and 65% polyester that is stained with carbon black and olive oil (EMPA 104). The stained textile is commercially available from Scientific Services, Inc. of the United Kingdom.

TABLE 9

|  | Cleaning Formulation 1 | Cleaning Formulation 2 | Cleaning Formulation 3 | Cleaning Formulation 4 | Cleaning Formulation 5 |
|---|---|---|---|---|---|
| Mean Percent Clean | 1.995 | 26.105 | 29.245 | 31.045 | 27.295 |
| Number of Samples | 2 | 2 | 2 | 2 | 2 |
| Standard Deviation | 0.757 | 0.177 | 1.761 | 1.223 | 0.290 |
|  | Cleaning Formulation 6 | Cleaning Formulation 7 | Cleaning Formulation 8 | Cleaning Formulation 9 | Cleaning Formulation 10 |
| Mean Percent Clean | 25.775 | 30.020 | 31.715 | 23.725 | 5.730 |
| Number of Samples | 2 | 2 | 2 | 2 | 2 |
| Standard Deviation | 0.177 | 0.764 | 2.355 | 4.165 | 0.707 |
|  | Cleaning Formulation 11 | Cleaning Formulation 12 | Cleaning Formulation 13 | Cleaning Formulation 14 | Cleaning Formulation 15 |
| Mean Percent Clean | 31.110 | 23.645 | 31.980 | 28.705 | 32.390 |
| Number of Samples | 2 | 2 | 2 | 2 | 2 |
| Standard Deviation | 0.410 | 1.492 | 0.976 | 1.464 | 1.428 |
|  | Cleaning Formulation 16 | Cleaning Formulation 17 | Cleaning Formulation 18 | Cleaning Formulation 19 | Cleaning Formulation 20 |
| Mean Percent Clean | 30.275 | 26.265 | 9.425 | 28.280 | 19.025 |
| Number of Samples | 2 | 2 | 2 | 2 | 2 |
| Standard Deviation | 0.149 | 0.615 | 0.898 | 4.073 | 0.064 |
|  | Cleaning Formulation 21 | Cleaning Formulation 22 | Cleaning Formulation 23 | Cleaning Formulation 24 | Cleaning Formulation 25 |
| Mean Percent Clean | 29.410 | 24.760 | 13.520 | 10.550 | 28.045 |
| Number of Samples | 2 | 2 | 2 | 2 | 2 |
| Standard Deviation | 3.493 | 4.738 | 1.146 | 1.032 | 3.232 |

TABLE 9-continued

|  | Cleaning Formulation 26 | Cleaning Formulation 27 | Cleaning Formulation 28 | Cleaning Formulation 29 | Cleaning Formulation 30 |
|---|---|---|---|---|---|
| Mean Percent Clean | 29.490 | 28.910 | 25.575 | 24.230 | 5.958 |
| Number of Samples | 2 | 2 | 2 | 2 | 4 |
| Standard Deviation | 2.150 | 2.843 | 0.290 | 2.984 | 2.109 |

|  | Cleaning Formulation 31 | Cleaning Formulation 32 | Comp. Cleaning Formulation 1 | Comp. Cleaning Formulation 2 | Comp. Cleaning Formulation 3 |
|---|---|---|---|---|---|
| Mean Percent Clean | 15.905 | 29.595 | 6.235 | 29.775 | 2.055 |
| Number of Samples | 4 | 2 | 4 | 2 | 2 |
| Standard Deviation | 3.220 | 2.058 | 1.691 | 1.435 | 0.615 |

|  | Comp. Cleaning Formulation 4 | Comp. Cleaning Formulation 5 | Comp. Cleaning Formulation 6 | Comp. Cleaning Formulation 7 | Comp. Cleaning Formulation 8 |
|---|---|---|---|---|---|
| Mean Percent Clean | 30.925 | 29.890 | 0.385 | 19.590 | 32.170 |
| Number of Samples | 2 | 2 | 2 | 2 | 2 |
| Standard Deviation | 3.288 | 0.481 | 1.223 | 0.990 | 1.018 |

|  | Comp. Cleaning Formulation 9 | Comp. Cleaning Formulation 10 | Comp. Cleaning Formulation 11 | Comp. Cleaning Formulation 12 | Comp. Cleaning Formulation 13 |
|---|---|---|---|---|---|
| Mean Percent Clean | −0.415 | 26.405 | 31.470 | 34.005 | 4.835 |
| Number of Samples | 2 | 2 | 2 | 2 | 2 |
| Standard Deviation | 0.983 | 1.563 | 2.871 | 0.290 | 0.120 |

|  | Comp. Cleaning Formulation 14 | Comp. Cleaning Formulation 15 | Comp. Cleaning Formulation 16 |
|---|---|---|---|
| Mean Percent Clean | 5.645 | 9.228 | 14.373 |
| Number of Samples | 4 | 4 | 4 |
| Standard Deviation | 1.045 | 1.053 | 1.276 |

Figure 12:
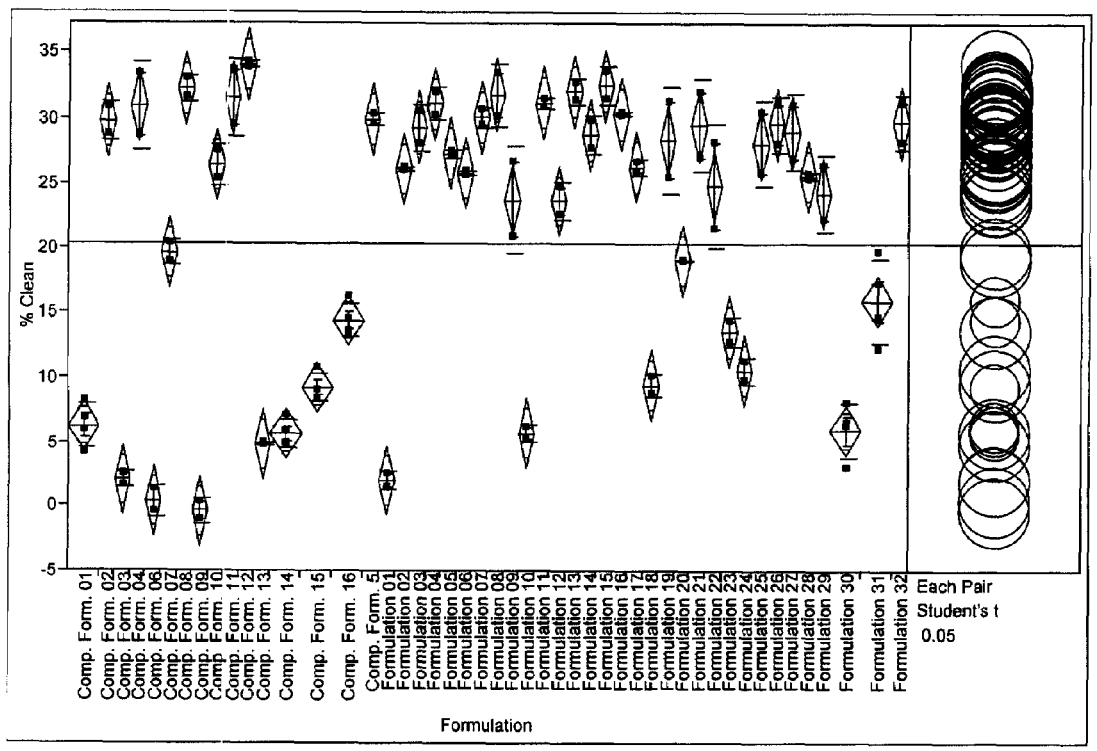
FIG. 12 is a diamond error graph of a one-way ANOVA of mean Percent Clean as a function of Cleaning Formulation. The Cleaning Formulations are diluted in a first cleaning solution and applied to polyester (65%)/cotton (35%) blend swatches stained with EMPA 104 (carbon black/olive oil) which are washed at 150° F.

As set forth in Table 9, and depicted in FIG. 12, the Formulations of the instant invention perform equally as well or better than many of the Comparative Formulations, as evidenced by the overlapping circles indicating that any differences between the Formulations and the Comparative Formulations are statistically insignificant at a confidence interval of 95%.

Table 10 includes mean percent clean data, and standard deviation, after washing a textile in the various Formulations at 120° F. This data represents the calculation of mean Percent Clean based on a number of sample measurements. The textile is a fabric including a blend of 35% cotton and 65% polyester that is stained with carbon black and mineral oil (EMPA 106). The stained textile is commercially available from Scientific Services, Inc. of the United Kingdom.

TABLE 10

|  | Cleaning Formulation 1 | Cleaning Formulation 2 | Cleaning Formulation 3 | Cleaning Formulation 4 | Cleaning Formulation 5 |
|---|---|---|---|---|---|
| Mean Percent Clean | 11.0350 | 21.1450 | 18.8400 | 17.8850 | 18.4450 |
| Number of Samples | 2 | 2 | 2 | 2 | 2 |
| Standard Deviation | 0.0778 | 1.0536 | 2.3900 | 0.4596 | 1.5486 |

TABLE 10-continued

|  | Cleaning Formulation 6 | Cleaning Formulation 7 | Cleaning Formulation 8 | Cleaning Formulation 9 | Cleaning Formulation 10 |
|---|---|---|---|---|---|
| Mean Percent Clean | 19.2950 | 17.5750 | 17.1700 | 20.8050 | 11.2250 |
| Number of Samples | 2 | 2 | 2 | 2 | 2 |
| Standard Deviation | 0.1909 | 2.9769 | 4.0022 | 0.9122 | 2.4678 |

|  | Cleaning Formulation 11 | Cleaning Formulation 12 | Cleaning Formulation 13 | Cleaning Formulation 14 | Cleaning Formulation 15 |
|---|---|---|---|---|---|
| Mean Percent Clean | 16.4350 | 18.5200 | 22.8600 | 16.2300 | 16.2600 |
| Number of Samples | 2 | 2 | 2 | 2 | 2 |
| Standard Deviation | 4.4477 | 1.6688 | 3.4790 | 3.1820 | 2.2769 |

|  | Cleaning Formulation 16 | Cleaning Formulation 17 | Cleaning Formulation 18 | Cleaning Formulation 19 | Cleaning Formulation 20 |
|---|---|---|---|---|---|
| Mean Percent Clean | 17.1450 | 23.0400 | 14.2950 | 20.7800 | 15.3900 |
| Number of Samples | 2 | 2 | 2 | 2 | 2 |
| Standard Deviation | 2.5244 | 3.1537 | 1.2516 | 3.7052 | 1.5556 |

|  | Cleaning Formulation 21 | Cleaning Formulation 22 | Cleaning Formulation 23 | Cleaning Formulation 24 | Cleaning Formulation 25 |
|---|---|---|---|---|---|
| Mean Percent Clean | 21.9600 | 18.0600 | 14.1350 | 11.6700 | 21.6750 |
| Number of Samples | 2 | 2 | 2 | 2 | 2 |
| Standard Deviation | 5.5861 | 6.2225 | 1.6617 | 2.3193 | 3.1042 |

|  | Cleaning Formulation 26 | Cleaning Formulation 27 | Cleaning Formulation 28 | Cleaning Formulation 29 | Cleaning Formulation 30 |
|---|---|---|---|---|---|
| Mean Percent Clean | 21.1150 | 19.2900 | 18.7800 | 25.1150 | 12.6750 |
| Number of Samples | 2 | 2 | 2 | 2 | 2 |
| Standard Deviation | 4.9427 | 0.4667 | 0.2828 | 2.0860 | 1.9163 |

|  | Cleaning Formulation 31 | Cleaning Formulation 32 | Comp. Cleaning Formulation 1 | Comp. Cleaning Formulation 2 | Comp. Cleaning Formulation 3 |
|---|---|---|---|---|---|
| Mean Percent Clean | 15.1700 | 20.3500 | 12.8500 | 19.8600 | 11.7150 |
| Number of Samples | 2 | 2 | 2 | 2 | 2 |
| Standard Deviation | 3.6204 | 1.7395 | 1.2869 | 1.9940 | 1.4779 |

|  | Comp. Cleaning Formulation 4 | Comp. Cleaning Formulation 5 | Comp. Cleaning Formulation 6 | Comp. Cleaning Formulation 7 | Comp. Cleaning Formulation 8 |
|---|---|---|---|---|---|
| Mean Percent Clean | 15.3200 | 22.6650 | 4.7950 | 18.6900 | 21.9950 |
| Number of Samples | 2 | 2 | 2 | 2 | 2 |
| Standard Deviation | 2.3759 | 3.8679 | 2.5102 | 0.7920 | 4.5891 |

|  | Comp. Cleaning Formulation 9 | Comp. Cleaning Formulation 10 | Comp. Cleaning Formulation 11 | Comp. Cleaning Formulation 12 | Comp. Cleaning Formulation 13 |
|---|---|---|---|---|---|
| Mean Percent Clean | 11.5850 | 24.6300 | 24.0450 | 25.3150 | 12.0900 |

TABLE 10-continued

|  | | | | | |
|---|---|---|---|---|---|
| Number of Samples | 2 | 2 | 2 | 2 | 2 |
| Standard Deviation | 0.1344 | 1.8385 | 0.0354 | 1.3789 | 0.0990 |

|  | Comp. Cleaning Formulation 14 | Comp. Cleaning Formulation 15 | Comp. Cleaning Formulation 16 |
|---|---|---|---|
| Mean Percent Clean | 24.7000 | 15.5050 | 19.2100 |
| Number of Samples | 2 | 2 | 2 |
| Standard Deviation | 4.6952 | 2.0435 | 0.4384 |

Figure 13:
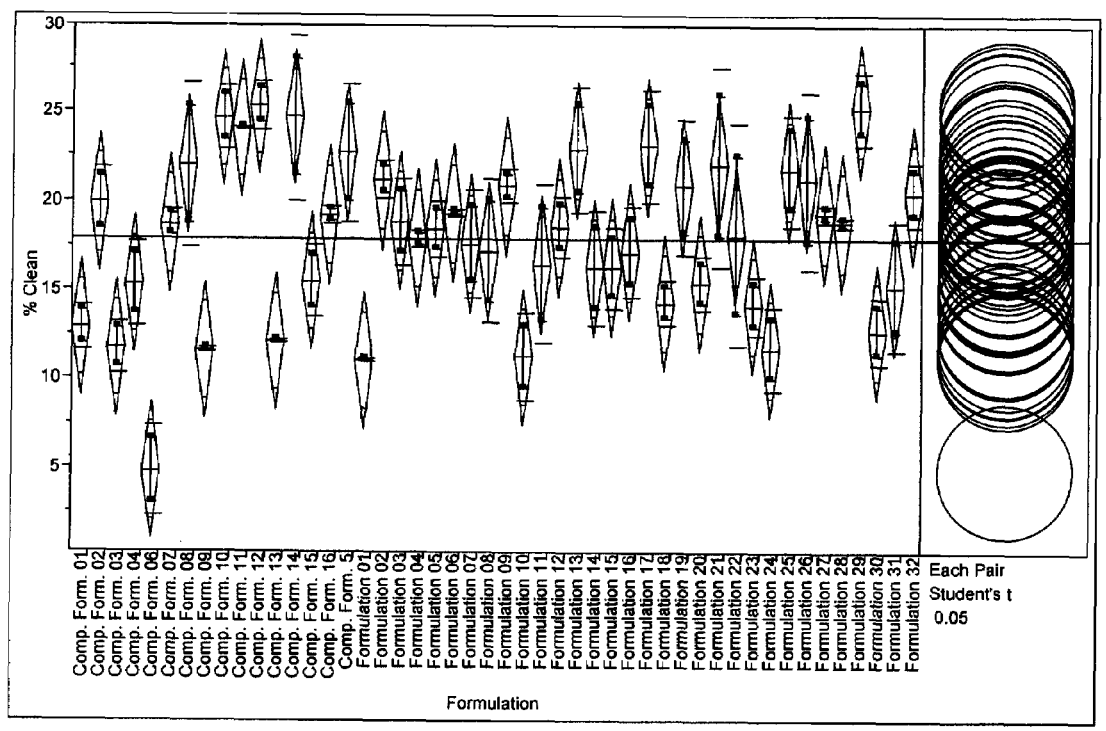
FIG. 13 is a diamond error graph of a one-way ANOVA of mean Percent Clean as a function of Cleaning Formulation. The Cleaning Formulations are diluted in a first cleaning solution and applied to 100% cotton swatches stained with EMPA 106 (carbon black/mineral oil) which are washed at 120° F.

As set forth in Table 10, and depicted in FIG. 13, the Formulations of the instant invention perform equally as well or better than many of the Comparative Formulations, as evidenced by the overlapping circles indicating that any differences between the Formulations and the Comparative Formulations are statistically insignificant at a confidence interval of 95%.

Table 11 includes mean percent clean data, and standard deviation, after washing a textile in the various Formulations at 150° F. This data represents the calculation of mean Percent Clean based on a number of sample measurements. The textile is a fabric including a blend of 35% cotton and 65% polyester that is stained with carbon black and mineral oil (EMPA 106). The stained textile is commercially available from Scientific Services, Inc. of the United Kingdom.

TABLE 11

|  | Cleaning Formulation 1 | Cleaning Formulation 2 | Cleaning Formulation 3 | Cleaning Formulation 4 | Cleaning Formulation 5 |
|---|---|---|---|---|---|
| Mean Percent Clean | 19.5750 | 23.3600 | 24.1050 | 24.6050 | 21.5650 |
| Number of Samples | 2 | 2 | 2 | 2 | 2 |
| Standard Deviation | 1.4637 | 3.9457 | 0.0778 | 1.1667 | 0.4031 |
|  | Cleaning Formulation 6 | Cleaning Formulation 7 | Cleaning Formulation 8 | Cleaning Formulation 9 | Cleaning Formulation 10 |
| Mean Percent Clean | 18.9750 | 24.6500 | 23.1000 | 21.5650 | 14.1950 |
| Number of Samples | 2 | 2 | 2 | 2 | 2 |
| Standard Deviation | 2.1001 | 2.3193 | 4.5679 | 4.5891 | 1.7466 |
|  | Cleaning Formulation 11 | Cleaning Formulation 12 | Cleaning Formulation 13 | Cleaning Formulation 14 | Cleaning Formulation 15 |
| Mean Percent Clean | 27.7950 | 22.7300 | 24.1900 | 20.9300 | 25.0850 |
| Number of Samples | 2 | 2 | 2 | 2 | 2 |
| Standard Deviation | 3.3588 | 1.3435 | 1.0607 | 3.4083 | 1.1809 |
|  | Cleaning Formulation 16 | Cleaning Formulation 17 | Cleaning Formulation 18 | Cleaning Formulation 19 | Cleaning Formulation 20 |
| Mean Percent Clean | 20.2950 | 50.7400 | 17.7900 | 25.1300 | 21.2500 |
| Number of Samples | 2 | 2 | 2 | 2 | 2 |
| Standard Deviation | 0.5869 | 2.3900 | 0.3818 | 0.3536 | 7.0852 |
|  | Cleaning Formulation 21 | Cleaning Formulation 22 | Cleaning Formulation 23 | Cleaning Formulation 24 | Cleaning Formulation 25 |
| Mean Percent Clean | 23.4100 | 20.2400 | 14.8450 | 11.9650 | 22.3300 |
| Number of Samples | 2 | 2 | 2 | 2 | 2 |

TABLE 11-continued

|  | | | | | |
|---|---|---|---|---|---|
| Standard Deviation | 1.7112 | 4.7800 | 0.8273 | 1.8880 | 0.3111 |

|  | Cleaning Formulation 26 | Cleaning Formulation 27 | Cleaning Formulation 28 | Cleaning Formulation 29 | Cleaning Formulation 30 |
|---|---|---|---|---|---|
| Mean Percent Clean | 24.1500 | 23.7750 | 15.4650 | 24.1450 | 14.9850 |
| Number of Samples | 2 | 2 | 2 | 2 | 4 |
| Standard Deviation | 5.2751 | 4.3770 | 0.3324 | 2.5103 | 3.2827 |

|  | Cleaning Formulation 31 | Cleaning Formulation 32 | Comp. Cleaning Formulation 1 | Comp. Cleaning Formulation 2 | Comp. Cleaning Formulation 3 |
|---|---|---|---|---|---|
| Mean Percent Clean | 17.6975 | 23.9150 | 12.8925 | 20.0350 | 16.1500 |
| Number of Samples | 4 | 2 | 4 | 2 | 2 |
| Standard Deviation | 2.7749 | 0.7849 | 3.7315 | 1.3789 | 2.8143 |

|  | Comp. Cleaning Formulation 4 | Comp. Cleaning Formulation 5 | Comp. Cleaning Formulation 6 | Comp. Cleaning Formulation 7 | Comp. Cleaning Formulation 8 |
|---|---|---|---|---|---|
| Mean Percent Clean | 22.5600 | 21.9600 | 15.2600 | 14.5650 | 19.8950 |
| Number of Samples | 2 | 2 | 2 | 2 | 2 |
| Standard Deviation | 2.5032 | 0.5940 | 0.1556 | 0.9829 | 0.7708 |

|  | Comp. Cleaning Formulation 9 | Comp. Cleaning Formulation 10 | Comp. Cleaning Formulation 11 | Comp. Cleaning Formulation 12 | Comp. Cleaning Formulation 13 |
|---|---|---|---|---|---|
| Mean Percent Clean | 19.3550 | 21.5050 | 28.8200 | 25.3000 | 15.0800 |
| Number of Samples | 2 | 2 | 2 | 2 | 2 |
| Standard Deviation | 0.3323 | 2.2132 | 3.2527 | 1.1597 | 5.1195 |

|  | Comp. Cleaning Formulation 14 | Comp. Cleaning Formulation 15 | Comp. Cleaning Formulation 16 |
|---|---|---|---|
| Mean Percent Clean | 23.1525 | 21.9425 | 23.0375 |
| Number of Samples | 4 | 4 | 4 |
| Standard Deviation | 2.1945 | 1.3115 | 4.3575 |

Figure 14:
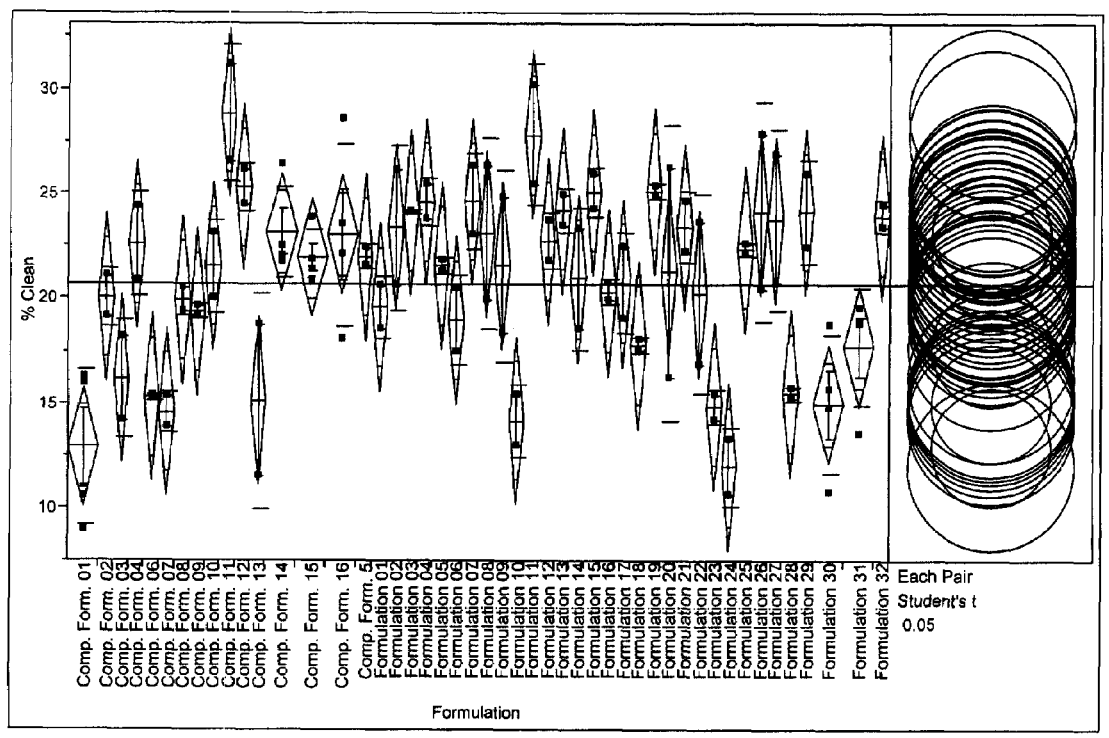
FIG. 14 is a diamond error graph of a one-way ANOVA of mean Percent Clean as a function of Cleaning Formulation. The Cleaning Formulations are diluted in a first cleaning solution and applied to 100% cotton swatches stained with EMPA 106 (carbon black/mineral oil) which are washed at 150° F.

As set forth in Table 11, and depicted in FIG. 14, the Formulations of the instant invention perform equally as well or better than many of the Comparative Formulations, as evidenced by the overlapping circles indicating that any differences between the Formulations and the Comparative Formulations are statistically insignificant at a confidence interval of 95%.

As shown in Tables 2-11, and as visually depicted in FIGS. 5-14, the Cleaning Formulations of the instant invention are used to clean the textiles in laundering applications with a similar or better efficacy than known surfactants. In addition to being able to effectively clean the textiles, the Cleaning Formulations of the instant invention are also biodegradable and therefore may reduce a possibility of pollution and formation of environmental hazards when used.

More specifically, the Cleaning Formulations of the instant invention provide greater cleaning efficacy than the Comparative Cleaning Formulations such as Comparative Cleaning Formulations 1-4, and 13-16. The Cleaning Formulations of the instant invention include combinations of similar, if not identical, surfactants as the Comparative Cleaning Formulations 1-4 and 13-16, yet provide higher mean percent clean values, i.e., greater cleaning efficacy.

In addition to Percent Clean calculations, the average Draves Wetting times of each of the Surfactant Compositions 1-13 and the Comparative Surfactant Compositions 1-16 are determined based on two measurements, via a method well known in the art. As is known in the art, the lesser the Draves Wetting times the faster the Formulations wet a surface. The Draves Wetting times are set forth in Table 12 below.

TABLE 12

| | Surfactant Comp. 1 | Surfactant Comp. 2 | Surfactant Comp. 3 | Surfactant Comp. 4 | Surfactant Comp. 5 | Surfactant Comp. 6 |
|---|---|---|---|---|---|---|
| Average Draves Wetting Time (s) | 12.5 | 9.5 | 20.5 | 16 | 7.5 | 31.5 |

| | Surfactant Comp. 7 | Surfactant Comp. 8 | Surfactant Comp. 9 | Surfactant Comp. 10 | Surfactant Comp. 11 | Surfactant Comp. 12 |
|---|---|---|---|---|---|---|
| Draves Wetting Time (s) | 7.5 | 12.8 | 7.3 | 6.3 | 4.4 | 4.7 |

| | Surfactant Comp. 13 | Compar. Surfactant Comp. 1 | Compar. Surfactant Comp. 2 | Compar. Surfactant Comp. 3 | Compar. Surfactant Comp. 4 | Compar. Surfactant Comp. 5 |
|---|---|---|---|---|---|---|
| Draves Wetting Time (s) | 5.6 | 94.5 | 15.5 | 55.3 | 16.5 | >3600 |

| | Compar. Surfactant Comp. 6 | Compar. Surfactant Comp. 7 | Compar. Surfactant Comp. 8 | Compar. Surfactant Comp. 9 | Compar. Surfactant Comp. 10 | Compar. Surfactant Comp. 11 |
|---|---|---|---|---|---|---|
| Draves Wetting Time (s) | 34 | 9 | 4.9 | 6 | 4.1 | 4.5 |

| | Compar. Surfactant Comp. 12 | Compar. Surfactant Comp. 13 | Compar. Surfactant Comp. 14 | Compar. Surfactant Comp. 15 | Compar. Surfactant Comp. 16 |
|---|---|---|---|---|---|
| Draves Wetting Time (s) | 45.2 | 7.6 | 3.6 | 5.6 | 22.7 |

As shown above in Table 12, the Surfactant Compositions of the instant invention generally exhibit increased speeds of Draves Wetting, as compared to the Comparative Surfactant Compositions. The increased speeds of Draves Wetting indicate that the Surfactant Compositions of the instant invention wet the textiles faster than the Comparative Surfactant Compositions and therefore interact more completely with the textiles, leading to increased cleaning ability. Specifically, it is believed that faster wetting contributes to increased cleaning effectiveness and increased Mean Percent Clean of the Cleaning Formulations of the instant invention.

The viscosities of the Surfactant Compositions 1-13 and Comparative Surfactant Compositions 1-16, as diluted in various amounts in water, are also measured and set forth in Table 13 below. All values set forth in Table 13 below are in centipoises (cPs) at room temperature (~22° C.).

TABLE 13

| | Surfactant Comp. 1* | Surfactant Comp. 2* | Surfactant Comp. 3* | Surfactant Comp. 4** | Surfactant Comp. 5** | Surfactant Comp. 6* |
|---|---|---|---|---|---|---|
| 10% dilution | N/A | N/A | N/A | 51.3 | 71.8 | N/A |
| 20% dilution | 10.3 | 20.5 | N/A | 87.2 | 221 | N/A |
| 30% dilution | 30.8 | 133 | 35.9 | 92.3 | 893 | N/A |
| 40% dilution | 66.7 | 313 | 354 | 205 | 1795 | 33.7 |
| 50% dilution | 76.9 | 256 | 410 | 185 | 2113 | 46.8 |
| 60% dilution | 87.2 | 190 | 215 | 4442 | 380 | 95 |
| 70% dilution | 87.2 | 113 | 144 | 3011 | 71.8 | 83.8 |
| 80% dilution | 92.3 | 113 | 103 | 97.5 | 61.6 | 56.8 |
| 90% dilution | 82.1 | 103 | 92.3 | 76.9 | 51.3 | N/A |

TABLE 13-continued

| | Surfactant Comp. 7* | Surfactant Comp. 8** | Surfactant Comp. 9* | Surfactant Comp. 10** | Surfactant Comp. 11** | Surfactant Comp. 12* |
|---|---|---|---|---|---|---|
| 10% dilution | N/A | N/A | N/A | N/A | N/A | N/A |
| 20% dilution | N/A | N/A | N/A | N/A | N/A | N/A |
| 30% dilution | N/A | N/A | N/A | N/A | N/A | N/A |
| 40% dilution | 39.4 | 983 | 80.8 | 445 | 71.8 | 67.1 |
| 50% dilution | 62.8 | 3072 | 110 | 8397 | 415 | 65.5 |
| 60% dilution | 62.8 | 1229 | 112 | 5775 | 1065 | 75.2 |
| 70% dilution | 52.4 | 1843 | 81.8 | 1475 | 1720 | 82.1** |
| 80% dilution | 49.4 | 2130 | 57.1 | N/A | N/A | N/A |
| 90% dilution | N/A | N/A | N/A | N/A | N/A | N/A |

| | Surfactant Comp. 13* | Compar. Surfactant Comp. 1** | Compar. Surfactant Comp. 2** | Compar. Surfactant Comp. 3** | Compar. Surfactant Comp. 4** | Compar. Surfactant Comp. 5** |
|---|---|---|---|---|---|---|
| 10% dilution | N/A | N/A | N/A | N/A | N/A | N/A |
| 20% dilution | N/A | N/A | 51.3 | N/A | N/A | N/A |
| 30% dilution | N/A | N/A | 1180 | N/A | N/A | N/A |
| 40% dilution | 86.8 | 2540 | 4970 | 108 | 1270 | 272 |
| 50% dilution | 105 | 4915 | 10699 | 1434 | 4506 | 18309 |
| 60% dilution | 96.2 | 5530 | 1472 | 4424 | 983 | 6267 |
| 70% dilution | 89.2 | 1925 | 1472 | ~10,000 | 1597 | 1966 |
| 80% dilution | 81.5 | 1188 | 2016 | 133 | 1966 | 451 |
| 90% dilution | N/A | N/A | 108 | N/A | N/A | N/A |

| | Compar. Surfactant Comp. 6** | Compar. Surfactant Comp. 7** | Compar. Surfactant Comp. 8* | Compar. Surfactant Comp. 9** | Compar. Surfactant Comp. 10** | Compar. Surfactant Comp. 11**d |
|---|---|---|---|---|---|---|
| 10% dilution | N/A | N/A | N/A | N/A | N/A | N/A |
| 20% dilution | N/A | N/A | N/A | N/A | N/A | N/A |
| 30% dilution | N/A | N/A | N/A | N/A | N/A | N/A |
| 40% dilution | 3564 | 6840 | 91.8 | 30.8 | 5120 | 71.8 |
| 50% dilution | 7414 | 7168 | 58.5 | 71.8 | 246 | 144 |
| 60% dilution | 1434 | 21709 | 81.8 | 59.1* | 256 | 819 |
| 70% dilution | 4055 | 3195 | 72.1 | 72.1* | 60.5* | 103 |
| 80% dilution | 3686 | 532 | 52.8 | 52.8* | 48.4* | 71.8 |
| 90% dilution | N/A | N/A | N/A | N/A | N/A | N/A |

| | Compar. Surfactant Comp. 12* | Compar. Surfactant Comp. 13** | Compar. Surfactant Comp. 14** | Compar. Surfactant Comp. 15** | Compar. Surfactant Comp. 16** |
|---|---|---|---|---|---|
| 10% dilution | N/A | N/A | N/A | N/A | N/A |

TABLE 13-continued

| | | | | | |
|---|---|---|---|---|---|
| 20% dilution | N/A | N/A | N/A | N/A | N/A |
| 30% dilution | N/A | N/A | N/A | N/A | N/A |
| 40% dilution | 134 | 123 | 500 | 492 | 482 |
| 50% dilution | 160 | 472 | 705 | 451 | 8806 |
| 60% dilution | 125 | 2007 | 2020 | 1229 | 10158 |
| 70% dilution | 96.5 | 2417 | 2500 | 1802 | 272 |
| 80% dilution | 71.1 | 128 | 231 | 123 | 190 |
| 90% dilution | N/A | N/A | N/A | N/A | N/A |

*Measured with a Brookfield LVT Viscometer with Spindle 18
**Measured with a Brookfield Cone/Plate Viscometer at 38.3 reciprocal seconds As shown above in Table 13, the Surfactants of the instant invention generally exhibit lower viscosities when diluted in water than the Comparative Surfactants. It is believed that the lower viscosities, i.e., reduced gelling, decrease a need for dilution of the instant Surfactant Compositions or Cleaning Compositions with additional solvents and/or water upon use. This reduces shipping costs and purchasing costs for the end user.

An additional series of surfactant compositions (Surfactant Compositions 14-33) are also formed according to the present invention. Specifically, amounts of the First Aliphatic Alcohol and the Second Aliphatic Alcohol are added to a vessel and mixed. Subsequently, potassium hydroxide (KOH) as the Metal Catalyst is added to the vessel and mixed with the First Aliphatic Alcohol and the Second Aliphatic Alcohol to form a mixture. The mixture is heated to 85° C. and agitated for 1 hour. Subsequently, the mixture is heated to 110° C. and adjusted to a pressure of approximately 90 psig. Then, Ethylene Oxide is added to the mixture to react with the First Aliphatic Alcohol and the Second Aliphatic Alcohol, thereby forming the First Surfactant and the Second Surfactant, forming the Polyethylene Glycol in situ, and forming the Compositions 14-33. The Ethylene Oxide is added to the mixture at a rate of approximately 1100-1200 gm/hr while the temperature of the mixture is allowed to increase to approximately 145° C. After formation of the First Surfactant, Second Surfactant, and Polyethylene Glycol, the temperature of the reaction vessel is lowered to approximately 80° C.

Amounts of each of the Metal Catalyst, the First Alcohol, the Second Alcohol, and the Ethylene Oxide, used to form the Surfactant Compositions 14-33, are set forth in Table 14 below, wherein all amounts are in grams unless otherwise indicated.

TABLE 14

| Components | Surfactant Comp. 14 | Surfactant Comp. 15 | Surfactant Comp. 16 | Surfactant Comp. 17 |
|---|---|---|---|---|
| First Aliphatic Alcohol | 345 | 345 | 345 | 345 |
| Second Aliphatic Alcohol | 1380 | 1380 | 1380 | 1380 |
| Metal Catalyst | 20 | 20 | 20 | 20 |
| Ethylene Oxide | 4044 | 4448 | 4853 | 2426 |
| Weight Percent of First Aliphatic Alcohol | 20 | 20 | 20 | 20 |
| Weight Percent of Second Aliphatic Alcohol | 80 | 80 | 80 | 80 |
| Moles of Ethylene Oxide Added to Reaction | 10 | 11 | 12 | 6 |

TABLE 14-continued

| Components | Surfactant Comp. 18 | Surfactant Comp. 19 | Surfactant Comp. 20 | Surfactant Comp. 21 |
|---|---|---|---|---|
| First Aliphatic Alcohol | 345 | 345 | 825 | 825 |
| Second Aliphatic Alcohol | 1380 | 1380 | 825 | 825 |
| Metal Catalyst | 20 | 20 | 18 | 18 |
| Ethylene Oxide | 2831 | 3640 | 4115 | 4526 |
| Weight Percent of First Aliphatic Alcohol | 20 | 20 | 50 | 50 |
| Weight Percent of Second Aliphatic Alcohol | 80 | 80 | 50 | 50 |
| Moles of Ethylene Oxide Added to Reaction | 7 | 9 | 10 | 11 |

| Components | Surfactant Comp. 22 | Surfactant Comp. 23 | Surfactant Comp. 24 | Surfactant Comp. 25 |
|---|---|---|---|---|
| First Aliphatic Alcohol | 825 | 825 | 825 | 825 |
| Second Aliphatic Alcohol | 825 | 825 | 825 | 825 |
| Metal Catalyst | 18 | 18 | 18 | 18 |
| Ethylene Oxide | 4937 | 2469 | 2880 | 3292 |
| Weight Percent of First Aliphatic Alcohol | 50 | 50 | 50 | 50 |
| Weight Percent of Second Aliphatic Alcohol | 50 | 50 | 50 | 50 |
| Moles of Ethylene Oxide Added to Reaction | 12 | 6 | 7 | 8 |

| Components | Surfactant Comp. 26 | Surfactant Comp. 27 | Surfactant Comp. 28 | Surfactant Comp. 29 |
|---|---|---|---|---|
| First Aliphatic Alcohol | 825 | 1260 | 1260 | 1260 |
| Second Aliphatic Alcohol | 825 | 315 | 315 | 315 |
| Metal Catalyst | 18 | 18 | 18 | 18 |
| Ethylene Oxide | 3703 | 4194 | 4613 | 5033 |
| Weight Percent of First Aliphatic Alcohol | 50 | 80 | 80 | 80 |
| Weight Percent of Second Aliphatic Alcohol | 50 | 20 | 20 | 20 |

TABLE 14-continued

| Components | Surfactant Comp. 30 | Surfactant Comp. 31 | Surfactant Comp. 32 | Surfactant Comp. 33 |
|---|---|---|---|---|
| First Aliphatic Alcohol | 1260 | 1260 | 1260 | 1260 |
| Second Aliphatic Alcohol | 315 | 315 | 315 | 315 |
| Metal Catalyst | 18 | 18 | 18 | 18 |
| Ethylene Oxide | 2516 | 2936 | 3355 | 3775 |
| Weight Percent of First Aliphatic Alcohol | 80 | 80 | 80 | 80 |
| Weight Percent of Second Aliphatic Alcohol | 20 | 20 | 20 | 20 |
| Moles of Ethylene Oxide Added to Reaction | 6 | 7 | 8 | 9 |

The First Aliphatic Alcohol, Second Aliphatic Alcohol, and Metal Catalyst are the same as above. Surfactant Composition 19 is the same as Surfactant Composition 3. Surfactant Composition 33 is the same as Surfactant Composition 1. Additionally, Surfactant Compositions 34-36 are also formed. Surfactant Composition 34 is the same as Surfactant Composition 2, described in detail above. Surfactant Composition 35 is formed via the same method described immediately above from 400 grams of the First Aliphatic Alcohol, 1600 grams of the Second Aliphatic Alcohol, 22 grams of the Metal Catalyst, and 3331 grams of the Ethylene Oxide such that the Weight Percent of the First Aliphatic Alcohol is 20%, the Weight Percent of the Second Aliphatic Alcohol is 80%, and 7.1 moles of Ethylene Oxide are added to the First and Second Aliphatic Alcohols. Surfactant Composition 36 is also is formed via the same method described immediately above from 1200 grams of the First Aliphatic Alcohol, 300 grams of the Second Aliphatic Alcohol, 17 grams of the Metal Catalyst, and 2949 grams of the Ethylene Oxide such that the Weight Percent of the First Aliphatic Alcohol is 80%, the Weight Percent of the Second Aliphatic Alcohol is 20%, and 7.4 moles of Ethylene Oxide are added to the First and Second Aliphatic Alcohols. For both Surfactants 35 and 36, the cloud point is 54° C. The Surfactant Compositions 35 and 36 are stripped under vacuum to remove any water of catalysis and exclude formation of polyethylene glycol in situ. Subsequently, approximately 9 weight percent of polyethylene glycol having a number average molecular weight of 600 g/mol is added to each, after stripping, to form the completed Surfactant Compositions 35 and 36.

After formation, differing amounts of each of the Surfactant Compositions 14-36, in addition to samples of Comparative Surfactant Compositions 17-24, are independently added to a second cleaning solution (cleaning solution 2). Further, differing amounts of each of the Surfactant Compositions 14-34, in addition to samples of Comparative Surfactant Compositions 17-24, are independently added to a third cleaning solution (cleaning solution 3). It is to be appreciated that before addition into the second and third cleaning solutions, each of the Surfactant Compositions 14-36 are neutralized to a pH of approximately from 5 to 7.

Comparative Surfactant Composition 17 is formed via the same method described immediately above from 400 grams of the First Aliphatic Alcohol, 1600 grams of the Second Aliphatic Alcohol, 22 grams of the Metal Catalyst, and 3331 grams of the Ethylene Oxide. However, in this case, the Comparative Surfactant Composition 17 is stripped under vacuum to remove water of catalysis and exclude formation of polyethylene glycol in situ. The Weight Percent of the First Aliphatic Alcohol is 20% and the Weight Percent of the Second Aliphatic Alcohol is 80% with a degree of ethoxylation of 7.1. No additional polyethylene glycol is added to Comparative Surfactant Composition 17.

Comparative Surfactant Composition 18 includes a blend of 7 mole ethylene oxide adducts of alcohols having from 12 to 14 carbon atoms and is commercially available from BASF Corporation.

Comparative Surfactant Composition 19 includes 20% by weight of includes a blend of 7 mole ethylene oxide adducts of alcohols having from 12 to 14 carbon atoms that is commercially available from BASF Corporation and 80% by weight of a 7 mole ethylene oxide adduct of 2-propylheptanol that is commercially available from BASF Corporation.

Comparative Surfactant Composition 20 includes 50% by weight of includes a blend of 7 mole ethylene oxide adducts of alcohols having from 12 to 14 carbon atoms that is commercially available from BASF Corporation and 50% by weight of a 7 mole ethylene oxide adduct of 2-propylheptanol that is commercially available from BASF Corporation.

Comparative Surfactant Composition 21 includes 80% by weight of includes a blend of 7 mole ethylene oxide adducts of alcohols having from 12 to 14 carbon atoms that is commercially available from BASF Corporation and 20% by weight of a 7 mole ethylene oxide adduct of 2-propylheptanol that is commercially available from BASF Corporation.

Comparative Surfactant Composition 22 is formed via the same method described immediately above from 1200 grams of the First Aliphatic Alcohol, 300 grams of the Second Aliphatic Alcohol, 17 grams of the Metal Catalyst, and 2949 grams of the Ethylene Oxide. In this case, the Comparative Surfactant Composition 22 is stripped under vacuum to remove water of catalysis and exclude formation of polyethylene glycol in situ. The Weight Percent of the First Aliphatic Alcohol is 80%, the Weight Percent of the Second Aliphatic Alcohol is 20%, and the degree ethoxylation equal is 7.4. No additional polyethylene glycol is added to Comparative Surfactant Composition 22.

Comparative Surfactant Composition 23 includes a 9 mole ethoxylate of nonylphenol that is commercially available from BASF Corporation.

Comparative Surfactant Composition 24 is commercially available from Tomah Products, Inc. of Milton, Wis. under the trade name of Tomadol® 900 Surfactant. The Tomadol® 900 Surfactant does not include an amount of polyethylene glycol in excess of three percent by weight.

The amounts of each of the Surfactant Compositions 14-36, in addition to samples of Comparative Surfactant Compositions 17-24, that are added to cleaning solution 2 form Cleaning Formulations 33-55 and Comparative Cleaning Formulations 17-24, respectively. The amounts of each of the Surfactant Compositions 14-34, in addition to samples of Comparative Surfactant Compositions 17-24, that are added to cleaning solution 3 form Cleaning Formulations 56-76 and Comparative Cleaning Formulations 25-32, respectively. Each of the Cleaning Formulations 33-76 and the Comparative Cleaning Formulations 17-32 are evaluated for Percent Clean when applied to 4×6 inch vinyl tiles. The Comparative Cleaning Formulations 17-32 are not formed according to the instant invention and do not include amounts of a polyalkylene glycol in excess of three percent by weight.

The cleaning solution 2, to which samples of each of the Surfactant Compositions 14-36 and the Comparative Surfactant Compositions 17-24 are added, includes:

1% by weight of one of the Surfactant Compositions 14-36 or the Comparative Surfactant Compositions 17-24;
6% by weight of dipropylene glycol methyl ether;
5% by weight of a 50% by weight aqueous solution of NaOH;
3% by weight of Trilon® M, commercially available from BASF Corporation of Wyandotte, Mich.;
3% by weight of a 40% by weight aqueous solution of sodium xylene sulfonate; and
a balance of water.

The cleaning solution 3, to which samples of each of the Surfactant Compositions 14-34 and the Comparative Surfactant Compositions 17-24 are added, includes:
2% by weight of one of Surfactant Compositions 14-34 or the Comparative Surfactant Compositions 17-24;
6% by weight of dipropylene glycol methyl ether;
5% by weight of a 50% by weight aqueous solution of NaOH;
3% by weight of Trilon® M;
3% by weight of a 40% by weight aqueous solution of sodium xylene sulfonate; and
a balance of water.

After the Cleaning Formulations 33-76 and the Comparative Cleaning Formulations 17-32 are formed, samples of each are used to clean 4×6 inch vinyl tiles, as introduced above. The efficacy of each of the Cleaning Formulations and Comparative Cleaning Formulations is evaluated based on a calculation of mean percent clean as defined above.

Initially, the reflectance of the clean tiles, i.e., the reflectance of the tiles "Before Soiling", is determined. Subsequently, the tiles are soiled with a soil composition. The soil composition includes a mixture of 50 grams of paint thinner, 4 grams of vegetable oil, 10 grams of mineral oil, 10 grams of clay, and 4.5 grams of graphite powder. After the tiles are soiled, the tiles are heated to 50° C. for 24 hours after which any excess of the soil composition is wiped from the tiles. After the excess soil composition is wiped from the tiles, the "After Soiling" reflectance of each of the tiles is determined.

To clean the tiles in these applications, a floor scrubbing pad, commercially available from 3M under the trade name of Scrubber Pad, is installed on a Gardner Scrubber. The tiles are then cleaned according to ASTM 4488. After cleaning using the Gardener Scrubber, the "After Cleaning" reflectance of each of the tiles is determined. Upon determination and averaging of each of the "Before Soiling", "After Soiling", and "After Cleaning" reflectance values for the tiles, the mean percent clean measurements are calculated and set forth in Table 15 below.

TABLE 15

|  | Cleaning Formulation 33 | Cleaning Formulation 34 | Cleaning Formulation 35 | Cleaning Formulation 36 | Cleaning Formulation 37 |
| --- | --- | --- | --- | --- | --- |
| Mean Percent Clean | 34.3350 | 19.4381 | 18.2356 | 35.7894 | 23.6513 |
| Number of Samples | 16 | 16 | 16 | 16 | 16 |
| Standard Deviation | 5.9230 | 8.8360 | 4.7868 | 4.9957 | 5.7312 |
|  | Cleaning Formulation 38 | Cleaning Formulation 39 | Cleaning Formulation 40 | Cleaning Formulation 41 | Cleaning Formulation 42 |
| Mean Percent Clean | 47.1981 | 22.9031 | 26.0881 | 31.7831 | 51.7531 |
| Number of Samples | 16 | 16 | 16 | 16 | 16 |
| Standard Deviation | 6.7931 | 7.3643 | 6.2801 | 6.4079 | 7.4297 |
|  | Cleaning Formulation 43 | Cleaning Formulation 44 | Cleaning Formulation 45 | Cleaning Formulation 46 | Cleaning Formulation 47 |
| Mean Percent Clean | 35.8365 | 31.8125 | 43.3144 | 28.4094 | 21.1806 |
| Number of Samples | 17 | 16 | 16 | 16 | 16 |
| Standard Deviation | 5.0684 | 2.9670 | 5.3350 | 5.2350 | 5.4807 |
|  | Cleaning Formulation 48 | Cleaning Formulation 49 | Cleaning Formulation 50 | Cleaning Formulation 51 | Cleaning Formulation 52 |
| Mean Percent Clean | 26.1888 | 48.3188 | 49.2794 | 45.2531 | 55.2431 |
| Number of Samples | 16 | 16 | 16 | 16 | 16 |
| Standard Deviation | 3.7477 | 7.6414 | 11.2973 | 3.33054 | 4.4311 |

TABLE 15-continued

|  | Cleaning Formulation 53 | Cleaning Formulation 54 | Cleaning Formulation 55 | Cleaning Formulation 56 | Cleaning Formulation 57 |
|---|---|---|---|---|---|
| Mean Percent Clean | 55.7628 | 56.5181 | 43.4833 | 69.4769 | 71.5175 |
| Number of Samples | 32 | 32 | 16 | 16 | 16 |
| Standard Deviation | 7.2661 | 7.1108 | 3.8735 | 5.0911 | 7.6215 |

|  | Cleaning Formulation 58 | Cleaning Formulation 59 | Cleaning Formulation 60 | Cleaning Formulation 61 | Cleaning Formulation 62 |
|---|---|---|---|---|---|
| Mean Percent Clean | 66.2938 | 75.3394 | 78.4569 | 68.3206 | 65.8288 |
| Number of Samples | 16 | 16 | 16 | 16 | 16 |
| Standard Deviation | 3.0513 | 2.5712 | 2.8722 | 5.5178 | 6.5472 |

|  | Cleaning Formulation 63 | Cleaning Formulation 64 | Cleaning Formulation 65 | Cleaning Formulation 66 | Cleaning Formulation 67 |
|---|---|---|---|---|---|
| Mean Percent Clean | 63.3019 | 63.0031 | 55.2169 | 76.0656 | 64.1269 |
| Number of Samples | 16 | 16 | 16 | 16 | 16 |
| Standard Deviation | 5.4748 | 7.4664 | 5.4442 | 2.6359 | 4.4160 |

|  | Cleaning Formulation 68 | Cleaning Formulation 69 | Cleaning Formulation 70 | Cleaning Formulation 71 | Cleaning Formulation 72 |
|---|---|---|---|---|---|
| Mean Percent Clean | 62.8738 | 67.5094 | 64.6044 | 62.5563 | 56.1456 |
| Number of Samples | 16 | 16 | 16 | 16 | 16 |
| Standard Deviation | 4.5894 | 6.3970 | 7.0962 | 5.5841 | 6.1877 |

|  | Cleaning Formulation 73 | Cleaning Formulation 74 | Cleaning Formulation 75 | Cleaning Formulation 76 | Comp. Cleaning Formulation 17 |
|---|---|---|---|---|---|
| Mean Percent Clean | 74.6675 | 78.7650 | 70.0181 | 74.0525 | 27.9530 |
| Number of Samples | 16 | 16 | 16 | 16 | 32 |
| Standard Deviation | 2.3835 | 1.5101 | 5.3884 | 2.9422 | 7.9217 |

|  | Comp. Cleaning Formulation 18 | Comp. Cleaning Formulation 19 | Comp. Cleaning Formulation 20 | Comp. Cleaning Formulation 21 | Comp. Cleaning Formulation 22 |
|---|---|---|---|---|---|
| Mean Percent Clean | 29.8944 | 49.3600 | 50.1431 | 47.5875 | 35.2547 |
| Number of Samples | 16 | 16 | 16 | 16 | 16 |
| Standard Deviation | 5.5370 | 4.3477 | 7.5318 | 6.0121 | 7.0158 |

|  | Comp. Cleaning Formulation 23 | Comp. Cleaning Formulation 24 | Comp. Cleaning Formulation 25 | Comp. Cleaning Formulation 26 | Comp. Cleaning Formulation 27 |
|---|---|---|---|---|---|
| Mean Percent Clean | 35.9613 | 54.5788 | 65.1038 | 63.0000 | 70.6869 |
| Number of Samples | 16 | 16 | 16 | 16 | 16 |

TABLE 15-continued

| Standard Deviation | 3.6525 | 1.7234 | 4.5176 | 5.2945 | 4.0543 |
|---|---|---|---|---|---|

| | Comp. Cleaning Formulation 28 | Comp. Cleaning Formulation 29 | Comp. Cleaning Formulation 30 | Comp. Cleaning Formulation 31 | Comp. Cleaning Formulation 32 |
|---|---|---|---|---|---|
| Mean Percent Clean | 72.6581 | 67.0144 | 64.2417 | 67.5575 | 70.4713 |
| Number of Samples | 16 | 16 | 16 | 16 | 16 |
| Standard Deviation | 3.0666 | 4.3981 | 5.6714 | 2.7616 | 5.3017 |

Figure 15:
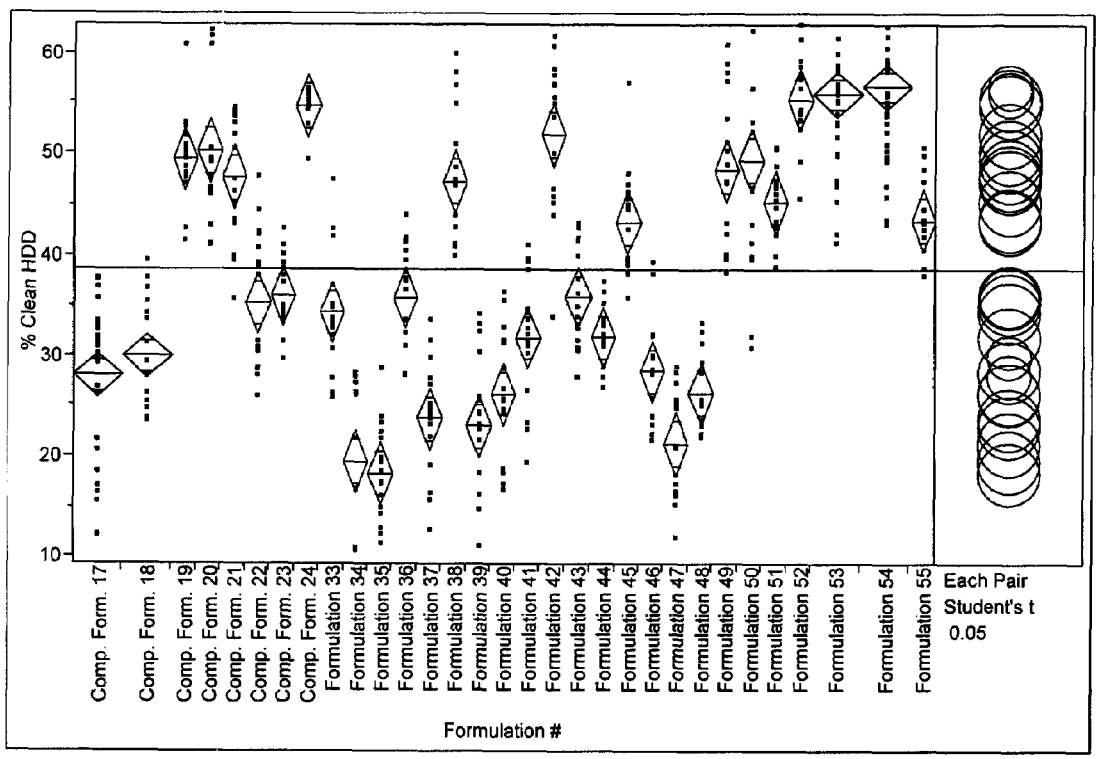
FIG. 15 is a diamond error graph of a one-way ANOVA of mean Percent Clean as a function of Cleaning Formulation diluted in a second cleaning solution and applied to 4×6 inch vinyl tiles stained with a soil composition and washed according to ASTM 4488.
Figure 16:
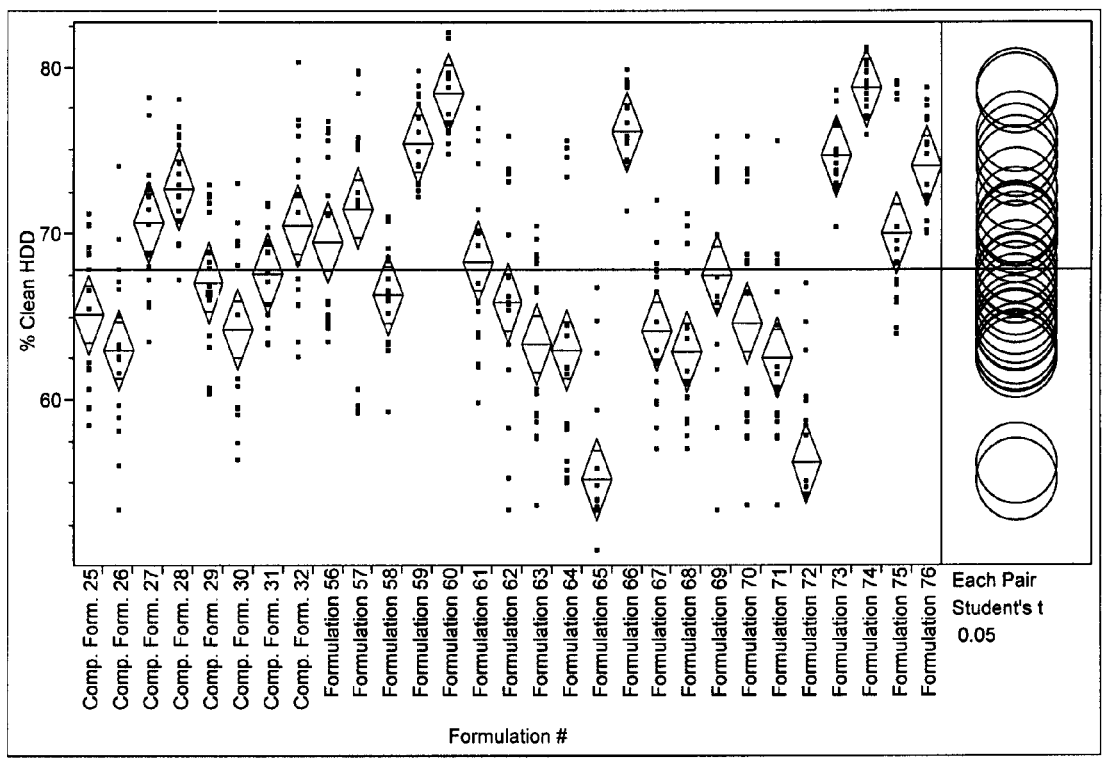
FIG. 16 is a diamond error graph of a one-way ANOVA of mean Percent Clean as a function of Cleaning Formulation. The Cleaning Formulations are diluted in a third cleaning solution and applied to 4×6 inch vinyl tiles stained with a soil composition and washed according to ASTM 4488.

As set forth in Table 15, and as depicted in FIGS. 15 and 16, the Cleaning Formulations of the instant invention perform equally as well or better than many of the Comparative Cleaning Formulations, as evidenced by the overlapping circles indicating that any differences between the Cleaning Formulations and the Comparative Cleaning Formulations are statistically insignificant at a confidence interval of 95%. In addition to being able to effectively clean the textiles, the Cleaning Formulations of the instant invention are also biodegradable and therefore may reduce a possibility of pollution and formation of environmental hazards when used.

Further, an additional Surfactant Compositions (Surfactant Composition 37) is also formed according to the instant invention and the method set forth above. Amounts of each of the Metal Catalyst, the First Alcohol, the Second Alcohol, and the Ethylene Oxide, used to form the Surfactant Compositions 37, are set forth in Table 16 below, wherein all amounts are in grams unless otherwise indicated.

TABLE 16

| Components | Surfactant Comp. 37 |
|---|---|
| First Aliphatic Alcohol | 400 |
| Second Aliphatic Alcohol | 1600 |
| Metal Catalyst | 22 |
| Ethylene Oxide | 3753 |
| Weight Percent of First Aliphatic Alcohol | 20 |
| Weight Percent of Second Aliphatic Alcohol | 80 |
| Moles of Ethylene Oxide Added to Reaction | 8 |

The First Aliphatic Alcohol, Second Aliphatic Alcohol, and Metal Catalyst are the same as above.

Differing amounts of each of the Surfactant Compositions 14-33 and 37, in addition to samples of Comparative Surfactant Compositions 17 and 22-27, are independently added to an additional cleaning solution (cleaning solution 4). The amounts of each of the Surfactant Compositions 14-33 and 37, in addition to samples of Comparative Surfactant Compositions 17 and 22-27, that are added to cleaning solution 4 form Cleaning Formulations 77-97 and Comparative Cleaning Formulations 33-39, respectively. It is to be appreciated that before addition into cleaning solution 4, each of the Surfactant Composition 14-33 and 37 are neutralized to a pH of approximately from 5 to 7.

Further, differing amounts of each of the Surfactant Compositions 14-33, 36 and 37 in addition to samples of Comparative Surfactant Compositions 17, 22, 23, and 25-27 are added to an additional cleaning solution (cleaning solution 5) form Cleaning Formulations 98-119 and Comparative Cleaning Formulations 40-45, respectively. It is to be appreciated that before addition into cleaning solution 5, each of the Surfactant Compositions 14-33, 36 and 37 are neutralized to a pH of approximately from 5 to 7.

Comparative Surfactant Compositions 17, 22 and 23 are as defined above.

Comparative Surfactant Composition 25 is formed via the same method described immediately above from 1260 grams of the First Aliphatic Alcohol, 315 grams of the Second Aliphatic Alcohol, 17 grams of the Metal Catalyst, and 3858 grams of the Ethylene Oxide. In this case, the Comparative Surfactant Composition 25 is stripped under vacuum to remove water of catalysis and exclude formation of polyethylene glycol in situ. The Weight Percent of the First Aliphatic Alcohol is 80%, the Weight Percent of the Second Aliphatic Alcohol is 20%, and the degree of ethoxylation is equal to 9.2. No additional polyethylene glycol is added to Comparative Surfactant Composition 25.

Comparative Surfactant Composition 26 is formed via the same method described immediately above from 325 grams of the First Aliphatic Alcohol, 1380 grams of the Second Aliphatic Alcohol, 19 grams of the Metal Catalyst, and 3227 grams of the Ethylene Oxide. In this case, the Comparative Surfactant Composition 26 is stripped under vacuum to remove water of catalysis and exclude formation of polyethylene glycol in situ. The Weight Percent of the First Aliphatic Alcohol is 20%, the Weight Percent of the Second Aliphatic Alcohol is 80%, and the degree of ethoxylation is equal to 8.1.

Comparative Surfactant Composition 27 includes a mixture of $C_9$-$C_{11}$ alcohols ethoxylated with approximately 6 moles of ethylene oxide and is commercially available from Shell Chemicals of Houston, Tex. under the trade name of Neodol® 91-6.

Cleaning solution 4 includes 1% by weight of one of Surfactant Compositions 14-33 and 37 or Comparative Surfactant Compositions 17 and 22-27, 1% by weight of a linear alkyl benzenesulfonate sodium salt (40%), 8% by weight of sodium meta silicate, 6% by weight of EDTA (Trilon® B Chelate 38%), 1% by weight of a 50% by weight solution of NaOH, 6.5% by weight of sodium xylene sulfonate (40%), and a balance of water.

Cleaning solution 5 includes 4% by weight of one of Surfactant Compositions 14-33, 36 and 37 or Comparative Surfactant Compositions 17, 22, 23, and 25-27, 1% by weight of a linear alkyl benzenesulfonate sodium salt, 8% by weight of sodium meta silicate, 6% by weight of EDTA, 1% by weight of a 50% by weight solution of NaOH, 6.5% by weight of sodium xylene sulfanate, and a balance of water.

Each of the Cleaning Formulations 77-119 and the Comparative Cleaning Formulations 33-45 are evaluated for Mean Percent Clean in spray applications through calculation of an average mass of soil removed from four aluminum coupons after soiling and cleaning. Specifically, the aluminum coupons are cleaned, weighed, and soiled with approximately one gram of a second soil composition. The second soil composition includes 50 grams of dirty motor oil, i.e., motor oil that has been previously used in an engine, combined with 50 grams of bandy black clay. After soiling with the second soil composition, the aluminum coupons are placed in an oven at 110° F. for 24 hours to remove excess water. Subsequently, single aluminum coupons are sprayed at 45 psi for 30 seconds with a sample of one of the various Cleaning Formulations while rotating at ½ revs/second speed in a spray box. After spraying, the aluminum coupons are rinsed with 100 ml of deionized water and heated for 2 hours at 110° F. to remove excess water. The aluminum coupons are then weighed to determine an amount of the second soil composition removed. The amounts of the second soil composition removed from the four individual coupons are then averaged and used to calculate the Mean Percent Clean in spray applications, as first introduced above and as set forth in Table 17 below. The mean percent clean measurements for spray applications are calculated as: [(average amount of soil removed (g)÷(average amount of soil added)]×100. Higher mean percent clean measurements indicate greater degrees of cleaning ability of the Cleaning Formulations.

TABLE 17

|  | Cleaning Formulation 77 | Cleaning Formulation 78 | Cleaning Formulation 79 | Cleaning Formulation 80 | Cleaning Formulation 81 |
| --- | --- | --- | --- | --- | --- |
| Mean Percent Clean | 38.4394 | 37.1079 | 39.1661 | 30.5716 | 35.8224 |
| Number of Samples | 3 | 3 | 3 | 4 | 3 |
| Standard Deviation | 2.6159 | 1.9758 | 3.5317 | 10.1691 | 3.6996 |
|  | Cleaning Formulation 82 | Cleaning Formulation 83 | Cleaning Formulation 84 | Cleaning Formulation 85 | Cleaning Formulation 86 |
| Mean Percent Clean | 35.6755 | 57.4205 | 60.0727 | 26.9379 | 35.6171 |
| Number of Samples | 3 | 6 | 3 | 2 | 3 |
| Standard Deviation | 1.8556 | 8.6266 | 0.8526 | 0.7094 | 1.0785 |
|  | Cleaning Formulation 87 | Cleaning Formulation 88 | Cleaning Formulation 89 | Cleaning Formulation 90 | Cleaning Formulation 91 |
| Mean Percent Clean | 42.5352 | 35.0603 | 60.6276 | 44.3061 | 37.5051 |
| Number of Samples | 3 | 3 | 3 | 6 | 3 |
| Standard Deviation | 13.7501 | 3.6055 | 1.4899 | 7.2179 | 3.6960 |
|  | Cleaning Formulation 92 | Cleaning Formulation 93 | Cleaning Formulation 94 | Cleaning Formulation 95 | Cleaning Formulation 96 |
| Mean Percent Clean | 25.8966 | 36.2921 | 32.5060 | 44.5551 | 38.1565 |
| Number of Samples | 3 | 3 | 3 | 3 | 3 |
| Standard Deviation | 3.2612 | 2.6684 | 3.7889 | 8.5330 | 3.5578 |
|  | Cleaning Formulation 97 | Cleaning Formulation 98 | Cleaning Formulation 99 | Cleaning Formulation 100 | Cleaning Formulation 101 |
| Mean Percent Clean | 37.5501 | 47.9010 | 44.1421 | 50.0135 | 50.5431 |
| Number of Samples | 3 | 3 | 3 | 3 | 4 |
| Standard Deviation | 2.6707 | 2.9863 | 6.8320 | 5.6578 | 7.9934 |

TABLE 17-continued

|  | Cleaning Formulation 102 | Cleaning Formulation 103 | Cleaning Formulation 104 | Cleaning Formulation 105 | Cleaning Formulation 106 |
| --- | --- | --- | --- | --- | --- |
| Mean Percent Clean | 59.5450 | 72.6087 | 52.7211 | 49.5324 | 56.8372 |
| Number of Samples | 3 | 3 | 6 | 3 | 2 |
| Standard Deviation | 1.7911 | 1.7868 | 7.7115 | 5.2743 | 3.5930 |

|  | Cleaning Formulation 107 | Cleaning Formulation 108 | Cleaning Formulation 109 | Cleaning Formulation 110 | Cleaning Formulation 111 |
| --- | --- | --- | --- | --- | --- |
| Mean Percent Clean | 71.1097 | 73.0299 | 69.4222 | 78.8424 | 63.6069 |
| Number of Samples | 3 | 3 | 3 | 3 | 5 |
| Standard Deviation | 1.8281 | 3.6792 | 3.7036 | 4.8810 | 3.5707 |

|  | Cleaning Formulation 112 | Cleaning Formulation 113 | Cleaning Formulation 114 | Cleaning Formulation 115 | Cleaning Formulation 116 |
| --- | --- | --- | --- | --- | --- |
| Mean Percent Clean | 65.2370 | 73.7043 | 99.5511 | 98.2790 | 98.5717 |
| Number of Samples | 3 | 3 | 3 | 3 | 3 |
| Standard Deviation | 14.4874 | 13.5652 | 0.0694 | 0.3569 | 0.1379 |

|  | Cleaning Formulation 117 | Cleaning Formulation 118 | Cleaning Formulation 119 | Comp. Cleaning Formulation 33 | Comp. Cleaning Formulation 34 |
| --- | --- | --- | --- | --- | --- |
| Mean Percent Clean | 77.3064 | 62.3160 | 52.3039 | 41.9163 | 42.6360 |
| Number of Samples | 3 | 3 | 3 | 3 | 3 |
| Standard Deviation | 2.2953 | 5.7559 | 3.4046 | 4.6153 | 3.5064 |

|  | Comp. Cleaning Formulation 35 | Comp. Cleaning Formulation 36 | Comp. Cleaning Formulation 37 | Comp. Cleaning Formulation 38 | Comp. Cleaning Formulation 39 |
| --- | --- | --- | --- | --- | --- |
| Mean Percent Clean | 61.0259 | 41.8554 | 39.0149 | 33.4054 | 48.1023 |
| Number of Samples | 7 | 3 | 3 | 4 | 3 |
| Standard Deviation | 7.9292 | 3.3071 | 2.9913 | 6.7778 | 1.4128 |

|  | Comp. Cleaning Formulation 40 | Comp. Cleaning Formulation 41 | Comp. Cleaning Formulation 42 | Comp. Cleaning Formulation 43 | Comp. Cleaning Formulation 44 | Comp. Cleaning Formulation 45 |
| --- | --- | --- | --- | --- | --- | --- |
| Mean Percent Clean | 68.5162 | 85.2849 | 84.7912 | 69.6810 | 65.8655 | 68.0426 |
| Number of Samples | 3 | 3 | 3 | 3 | 3 | 3 |
| Standard Deviation | 8.6694 | 0.9784 | 2.6916 | 2.8662 | 7.6249 | 1.4969 |

Figure 17:
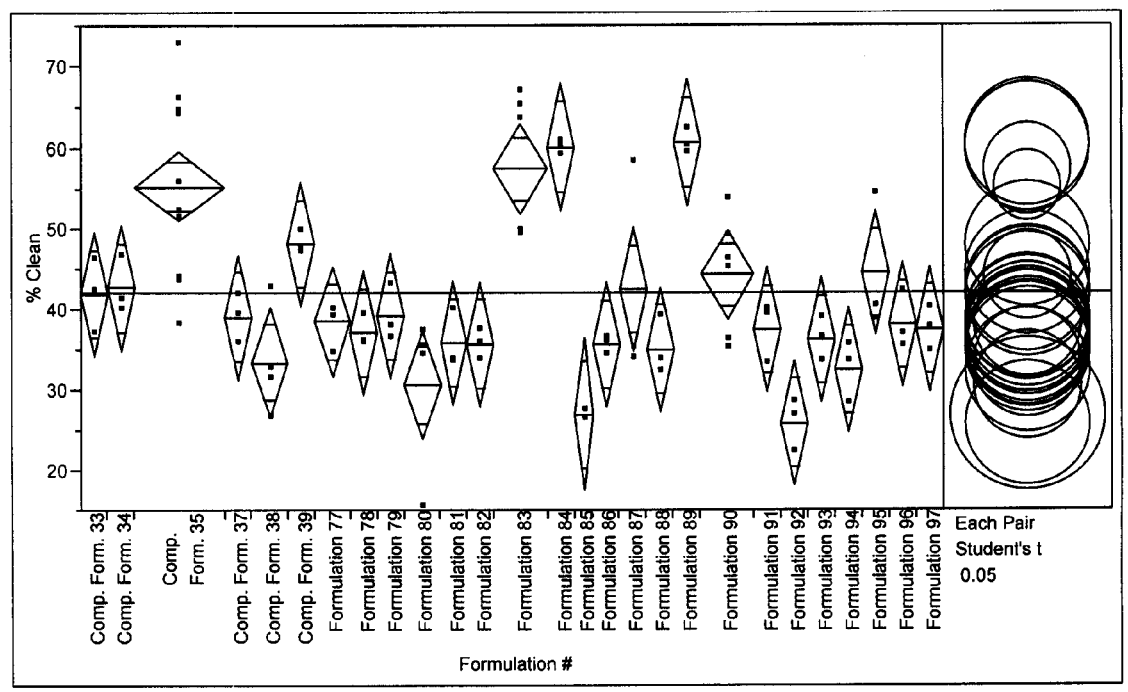
FIG. 17 is a diamond error graph of a one-way ANOVA of mean Percent Clean as a function of Cleaning Formulation. The Cleaning Formulations are diluted in a fourth cleaning solution and applied to aluminum coupons stained with a soil composition and washed via spraying.
Figure 18:
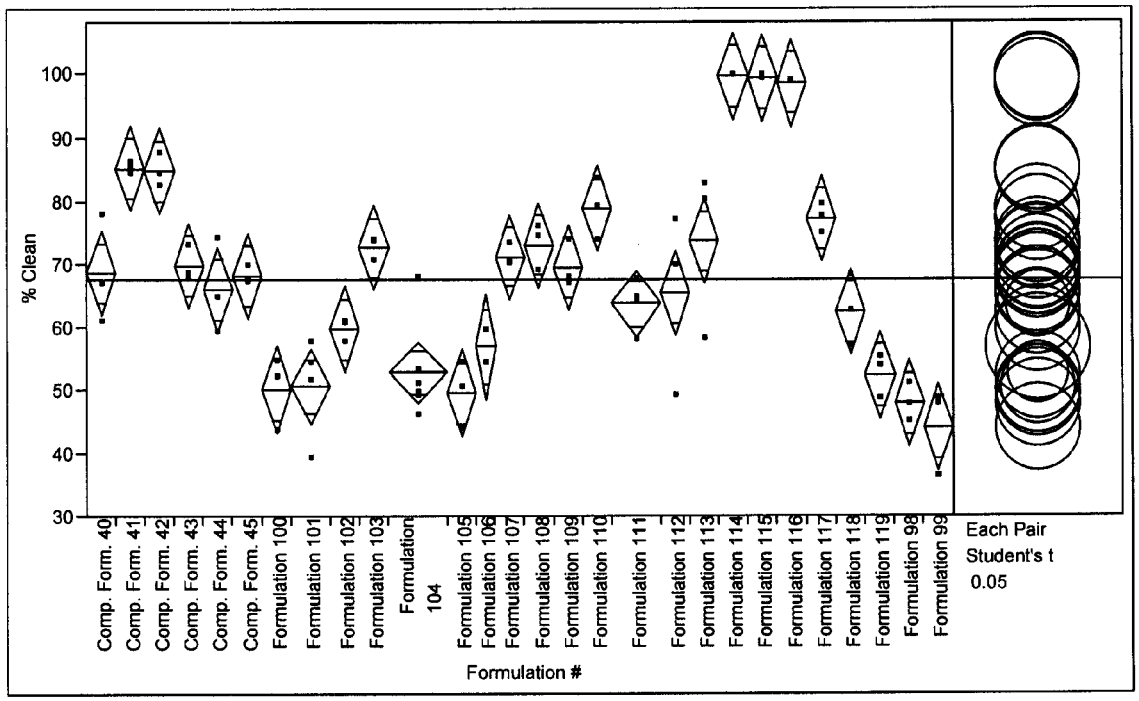
FIG. 18 is a diamond error graph of a one-way ANOVA of mean Percent Clean as a function of Cleaning Formulation. The Cleaning Formulations are diluted in a fifth cleaning solution and applied to aluminum coupons stained with a soil composition and washed via spraying.

As shown in Table 17 and as depicted in FIGS. 17 and 18, the Cleaning Compositions of the instant invention are used to effectively clean the aluminum coupons equally as well or better than many of the Comparative Formulations, as evidenced by the overlapping circles indicating that any differences between the Formulations and the Comparative Formulations are statistically insignificant at a confidence interval of 95%. In addition to being able to effectively clean the textiles, the Cleaning Formulations of the instant invention are also biodegradable and therefore may reduce a possibility of pollution and formation of environmental hazards when used.

The invention has been described in an illustrative manner, and it is to be understood that the terminology which has been used is intended to be in the nature of words of description rather than of limitation. Obviously, many modifications and variations of the present invention are possible in light of the above teachings, and the invention may be practiced otherwise than as specifically described.

What is claimed is:

1. A method of washing a surface, said method comprising the steps of:
   A. providing a cleaning formulation comprising a surfactant composition comprising;
      (i) a first surfactant having the general formula, $R^1\text{—O-}(A)_m H$ wherein $R^1$ is an aliphatic hydrocarbon having from 8 to 11 carbon atoms, A is an alkyleneoxy group having from 2 to 5 carbon atoms, and m is a positive number,
      (ii) a second surfactant having the general formula, $R^2\text{—O-}(B)_n H$ wherein $R^2$ is an aliphatic hydrocarbon having from 12 to 14 carbon atoms, B is an alkyleneoxy group having from 2 to 5 carbon atoms, and n is a positive number, and
      (iii) a polyalkylene glycol present in an amount of from 3 to 20 parts by weight per 100 parts by weight of the cleaning formulation;
   B. providing a rinse formulation;
   C. applying the cleaning formulation to the surface; and
   D. applying the rinse formulation to the surface.

2. A method as set forth in claim 1 wherein the cleaning formulation has a pH of greater than 10.

3. A method as set forth in claim 1 wherein the surface is further defined as a textile.

4. A method as set forth in claim 3 wherein the step of applying the cleaning composition to the textile is further defined as sudsing the cleaning formulation.

5. A method as set forth in claim 3 wherein the step of applying the rinse formulation is further defined as rinsing the textile with the rinse formulation.

6. A method as set forth in claim 1 wherein the step of applying the rinse formulation occurs more than once.

7. A method as set forth in claim 1 wherein the rinse formulation is the same as the cleaning formulation.

8. A method as set forth in claim 1 wherein the polyethylene glycol is present in the surfactant composition in an amount of from 8 to 10 parts by weight per 100 parts by weight of the surfactant composition.

9. A method as set forth in claim 1 wherein the polyalkylene glycol is further defined as a polyethylene glycol having a number average molecular weight of from 300 to 2000 g/mol.

10. A method as set forth in claim 9 wherein the polyalkylene glycol is further defined as a polyethylene glycol having a number average molecular weight of from 600 to 800 g/mol.

11. A method as set forth in claim 1 wherein the aliphatic hydrocarbon is further defined as a 2-propylheptane moiety.

12. A method as set forth in claim 1 wherein m is a number of from 3 to 12.

13. A method as set forth in claim 1 wherein the aliphatic hydrocarbon having from 8 to 11 carbon atoms has an average degree of branching of greater than zero.

14. A method as set forth in claim 1 wherein the aliphatic hydrocarbon having from 12 to 14 carbon atoms has an average degree of branching of zero.

15. A method as set forth in claim 1 wherein R1 is a 2-propylheptane moiety, A is an ethyleneoxy group, m is a number of from 3 to 12, B is an ethyleneoxy group, n is an number of from 3 to 12, and the polyalkylene glycol is further defined as a polyethylene glycol having a number average molecular weight of from 300 to 2000 g/mol.

16. A method as set forth in claim 1 wherein the surfactant composition consists essentially of the first surfactant, the second surfactant, and the polyalkylene glycol.

17. A method as set forth in claim 1 wherein the surfactant composition further comprises:
   a third surfactant different from the first surfactant and having the general formula, $R^1\text{—O-}(A)_m H$ wherein $R^1$ is an aliphatic hydrocarbon having from 8 to 11 carbon atoms, A is an alkyleneoxy group having from 2 to 5 carbon atoms, and m is a positive number; and
   a fourth surfactant different from the second surfactant and having the general formula, $R^2\text{—O-}(B)_n H$ wherein $R^2$ is an aliphatic hydrocarbon having from 12 to 14 carbon atoms, B is an alkyleneoxy group having from 2 to 5 carbon atoms, and n is a positive number.

18. A method as set forth in claim 17 wherein the surfactant composition consists essentially of the first, second, third, and fourth surfactants.

19. A method as set forth in claim 17 wherein the surfactant composition further comprises:
   a fifth surfactant different from the first and third surfactants and having the general formula, $R^1\text{—O-}(A)_m H$ wherein $R^1$ is an aliphatic hydrocarbon having from 8 to 11 carbon atoms, A is an alkyleneoxy group having from 2 to 5 carbon atoms, and m is a positive number; and
   a sixth surfactant different from the second and fourth surfactants and having the general formula, $R^2\text{—O-}(B)_n H$ wherein $R^2$ is an aliphatic hydrocarbon having from 12 to 14 carbon atoms, B is an alkyleneoxy group having from 2 to 5 carbon atoms, and n is a positive number.

20. A method as set forth in claim 1 wherein the surface is further defined as a textile, the cleaning formulation has a pH of greater than 10, the method further comprises the steps of sudsing the cleaning formulation, bleaching the textile, souring the textile, and the rinse formulation consists essentially of water.

21. A method of washing a surface, said method comprising the steps of:
   A. providing a cleaning formulation comprising a surfactant composition consisting essentially of;
      (i) a first surfactant having the general formula, $R^1\text{—O-}(A)_m H$ wherein R¹ is a 2-propylheptane moiety, A is an ethyleneoxy group, and m is a number of from 3 to 12,
(ii) a second surfactant having the general formula,

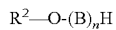

wherein R² is an aliphatic hydrocarbon having from 12 to 14 carbon atoms, B is an ethyleneoxy group, and n is an number of from 3 to 12, and
(iii) a polyalkylene glycol having a number average molecular weight of from 600 to 800 g/mol and present in an amount of from 8 to 10 parts by weight per 100 parts by weight of the cleaning formulation;
B. providing a rinse formulation;
C. applying the cleaning formulation to the surface; and
D. applying the rinse formulation to the surface.

22. A method as set forth in claim 21 wherein the surface is further defined as a textile.

23. A method as set forth in claim 22 wherein the cleaning composition has a pH of greater than 10.

24. A method as set forth in claim 21 wherein the rinse formulation consists essentially of water.

25. A method as set forth in claim 21 wherein the surfactant composition further consists essentially of:
a third surfactant different from the first surfactant and having the general formula,

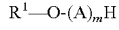

wherein R¹ is an aliphatic hydrocarbon having from 8 to 11 carbon atoms, A is an alkyleneoxy group having from 2 to 5 carbon atoms, and m is a positive number; and
a fourth surfactant different from the second surfactant and having the general formula,

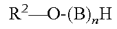

wherein R² is an aliphatic hydrocarbon having from 12 to 14 carbon atoms, B is an alkyleneoxy group having from 2 to 5 carbon atoms, and n is a positive number.

* * * * *